United States Patent
Hanks et al.

(10) Patent No.: US 12,121,565 B2
(45) Date of Patent: Oct. 22, 2024

(54) METHODS OF TREATMENT OF SPECIFIC CANCERS WITH NLRP3 INHIBITORS AND ANTI-PD1/PD-L1 ANTIBODIES

(71) Applicant: Duke University, Durham, NC (US)

(72) Inventors: Brent Hanks, Durham, NC (US); Balamayooran Theivanthiran, Durham, NC (US)

(73) Assignee: Duke University, Durham, NC (US)

( * ) Notice: Subject to any disclaimer, the term of this patent is extended or adjusted under 35 U.S.C. 154(b) by 361 days.

(21) Appl. No.: 17/020,164

(22) Filed: Sep. 14, 2020

(65) Prior Publication Data

US 2021/0077582 A1 Mar. 18, 2021

Related U.S. Application Data

(60) Provisional application No. 62/899,965, filed on Sep. 13, 2019.

(51) Int. Cl.

| | | |
|---|---|---|
| A61K 38/21 | (2006.01) | |
| A61K 39/00 | (2006.01) | |
| A61K 39/395 | (2006.01) | |
| A61K 45/06 | (2006.01) | |
| A61P 35/00 | (2006.01) | |
| C07K 16/28 | (2006.01) | |

(52) U.S. Cl.
CPC ...... *A61K 38/215* (2013.01); *A61K 39/39541* (2013.01); *A61K 45/06* (2013.01); *A61P 35/00* (2018.01); *C07K 16/2827* (2013.01); *A61K 2039/505* (2013.01)

(58) Field of Classification Search
CPC ............ A61K 38/215; A61K 39/39541; A61P 35/00; C07K 16/2827
See application file for complete search history.

(56) References Cited

U.S. PATENT DOCUMENTS

| | | |
|---|---|---|
| 7,595,048 B2 | 9/2009 | Honjo |
| 8,008,449 B2 | 8/2011 | Korman |
| 8,217,149 B2 | 7/2012 | Irving |
| 8,354,509 B2 | 1/2013 | Carven |
| 8,728,474 B2 | 5/2014 | Honjo |
| 8,735,553 B1 | 5/2014 | Li |
| 8,779,105 B2 | 7/2014 | Korman |
| 8,828,944 B2 * | 9/2014 | Zitvogel ................. A61P 35/00 514/19.3 |
| 8,900,587 B2 | 12/2014 | Carven |
| 8,952,136 B2 | 2/2015 | Carven |
| 9,067,999 B1 | 6/2015 | Honjo |
| 9,073,994 B2 | 7/2015 | Honjo |

FOREIGN PATENT DOCUMENTS

| | | | |
|---|---|---|---|
| EP | 2170959 B1 | 4/2010 | |
| WO | 2011066389 A1 | 6/2011 | |
| WO | 2017097407 A1 | 6/2017 | |
| WO | WO2019182981 | * 9/2019 | ............... A61P 1/00 |

OTHER PUBLICATIONS

Xu et al., Inflammasome inhibitors: promising therapeutic approaches against cancer. J. Hem. Onc. 12:64, 2019. (Year: 2019).*
Anastas JN, et al. WNT5A enhances resistance of melanoma cells to targeted BRAF inhibitors. J Clin Invest. 2014;124(7):2877-2890.
Asea A, et al. Novel signal transduction pathway utilized by extracellular HSP70: role of toll-like receptor (TLR) 2 and TLR4. J Biol Chem. 2002;277(17):15028-15034.
Bai H, et al. Downregulation of signal transduction and STAT3 expression exacerbates oxidative stress mediated by NLRP3 inflammasome. Neural Regen Res. 2018;13(12):2147-2155.
Benci JL, et al. Tumor interferon signaling regulates a multigenic resistance program to immune checkpoint blockade. Cell. 2016;167(6):1540-1554.e12.
Blumenthal A, et al. The wingless homolog WNT5A and its receptor Frizzled-5 regulate inflammatory responses of human mononuclear cells induced by microbial stimulation. Blood. 2006;108(3):965-973.
Booshehri LM, et al. CAPS and NLRP3. J Clin Immunol. 2019;39(3):277-286.
Chao T, et al. CXCR2-dependent accumulation of tumor-associated neutrophils regulates T-cell immunity in pancreatic ductal adenocarcinoma. Cancer Immunol Res. 2016;4(11):968-982.
Chen L, et al. CD38-mediated immunosuppression as a mechanism of tumor cell escape from PD-1/PD-L1 Blockade. Cancer Discov. 2018;8(9):1156-1175.
Clark, C. A., et al. "Tumor-intrinsic PD-L1 signals regulate cell growth, pathogenesis, and autophagy in ovarian cancer and melanoma." Cancer research 76.23 (2016): 6964-6974.
Coll RC, et al. A small-molecule inhibitor of the NLRP3 inflammasome for the treatment of inflammatory diseases. Nat Med. 2015;21(3):248-255.
Cordero MD, et al. Gain of function mutation and inflammasome driven diseases in human and mouse models. J Autoimmun. 2018;91:13-22.
Da Forno PD, et al. WNT5A expression increases during melanoma progression and correlates with outcome. Clin Cancer Res. 2008;14(18):5825-5832.
Dong P, et al. Tumor-intrinsic PD-L1 signaling in cancer initiation, development and treatment: beyond immune evasion. Front Oncol. 2018;8:386.
Eichelbaum K, et al. Selective enrichment of newly synthesized proteins for quantitative secretome analysis. Nat Biotechnol. 2012;30(10):984-990.
Escors D, et al. The intracellular signalosome of PD-L1 in cancer cells. Signal Transduct Target Ther. 2018;3:26.
Fang H, et al. Toll-like receptor 4 (TLR4) is essential for Hsp70-like protein 1 (HSP70L1) to activate dendritic cells and induce Th1 response. J Biol Chem. 2011;286(35):30393-30400.

(Continued)

*Primary Examiner* — Elly-Gerald Stoica
(74) *Attorney, Agent, or Firm* — Quarles & Brady, LLP

(57) ABSTRACT

The present disclosure provides, in part, compositions and methods of increasing the efficacy of anti-PD-1/PD-L1 antibody immunotherapy in a subject. The compositions and methods comprise an NLRP3 inhibitor used in combination with a PD-1 or PD-L1 inhibitor for the treatment of cancer.

17 Claims, 27 Drawing Sheets
(24 of 27 Drawing Sheet(s) Filed in Color)

Specification includes a Sequence Listing.

(56) References Cited

OTHER PUBLICATIONS

Gato-Cañas M, et al. PDL1 signals through conserved sequence motifs to overcome interferon-mediated cytotoxicity. Cell Rep. 2017;20(8):1818-1829.
He Y, et al. Mechanism and regulation of NLRP3 inflammasome activation. Trends Biochem Sci. 2016;41(12):1012-1021.
Highfill SL, et al. Disruption of CXCR2-mediated MDSC tumor trafficking enhances anti-PD1 efficacy. Sci Transl Med. 2014;6(237):237ra67.
Holtzhausen A, et al. Melanoma-derived Wnt5a promotes local dendritic-cell expression of IDO and Immunotolerance: opportunities for pharmacologic enhancement of immunotherapy. Cancer Immunol Res. 2015;3(9):1082-1095.
Hugo W, et al. Genomic and transcriptomic features of response to anti-PD-1 therapy in metastatic melanoma. Cell. 2016;165(1):35-44.
Johnson DB, et al. Tumor-specific MHC-II expression drives a unique pattern of resistance to immunotherapy via AG-3/FCRL6 engagement. JCI Insight. 2018;3(24):e120360.
Koyama, S., et al. "Adaptive resistance to therapeutic PD-1 blockade is associated with upregulation of alternative Immune checkpoints." Nature communications 7.1 (2016): 1-9.
Lecis D, et al. Immune checkpoint ligand reverse signaling: looking back to go forward in cancer therapy. Cancers (Basel). 2019;11(5):E624.
Li J, et al. Tumor cell-intrinsic factors underlie heterogeneity of immune cell infiltration and response to Immunotherapy. Immunity. 2018;49(1):178-193.e7.
Lu B, et al. Novel role of PKR in inflammasome activation and HMGB1 release. Nature. 2012;488(7413):670-674.
Mambula SS, et al. Heat shock protein 70 is secreted from tumor cells by a nonclassical pathway involving lysosomal endosomes. J Immunol. 2006;177(11):7849-7857.
Marigo I, et al. Tumor-induced tolerance and immune suppression by myeloid derived suppressor cells. Immunol Rev. 2008;222:162-179.
Marvel D, et al. Myeloid-derived suppressor cells in the tumor microenvironment: expect the unexpected. J Clin Invest. 2015;125(9):3356-3364.
Moossavi M, et al. Role of the NLRP3 inflammasome in cancer. Mol Cancer. 2018;17(1):158.
Munn DH, et al. Indoleamine 2,3-dioxygenase and tumor-induced tolerance. J Clin Invest. 2007;117(5):1147-1154.
Murphy ME. The HSP70 family and cancer. Carcinogenesis. 2013;34(6):1181-1188.
Ndoye A, et al. ATG5 mediates a positive feedback loop between Wnt signaling and autophagy in melanoma. Cancer Res. 2017;77(21):5873-5885.
Neubert NJ, et al. T cell-induced CSF1 promotes melanoma resistance to PD1 blockade. Sci Transl Med. 2018;10(436):eaan3311.
O'Donnell JS, et al. Resistance to PD1/PDL1 checkpoint inhibition. Cancer Treat Rev. 2017;52:71-81.
Oblak A, et al. Toll-like receptor 4 activation in cancer progression and therapy. Clin Dev Immunol. 2011;2011:609579.
Park HW, et al. Alternative Wnt signaling activates YAP/TAZ. Cell. 2015;162(4):780-794.
Pitt JM, et al. Resistance mechanisms to immune-checkpoint blockade in cancer: tumor-intrinsic and -extrinsic factors. Immunity. 2016;44(6):1255-1269.
Qu J, et al. Blocking ATP-sensitive potassium channel alleviates morphine tolerance by inhibiting HSP70-TLR4-NLRP3-mediated neuroinflammation. J Neuroinflammation. 2017;14(1):228.
Radons J. The human HSP70 family of chaperones: where do we stand? Cell Stress Chaperones. 2016;21(3):379-404.
Ribas, A., et al. "Association of pembrolizumab with tumor response and survival among patients with advanced melanoma." Jama 315.15 (2016): 1600-1609.
Sade-Feldman M, et al. Clinical significance of circulating CD33+ CD11b+HLA-DR-myeloid cells in patients with stage IV melanoma treated with ipilimumab. Clin Cancer Res. 2016;22(23):5661-5672.
Schaale, K., et al. "Wnt signaling in macrophages: augmenting and inhibiting mycobacteria-induced inflammatory responses." European journal of cell biology 90.6-7 (2011): 553-559.
Sharma P, et al. Primary, adaptive, and acquired resistance to cancer immunotherapy. Cell. 2017;168(4):707-723.
Shen S, et al. Cytoplasmic STAT3 represses autophagy by inhibiting PKR activity. Mol Cell. 2012;48(5):667-680.
Soler-Cardona A, et al. CXCL5 facilitates melanoma cell-neutrophil interaction and lymph node metastasis. J Invest Dermatol. 2018;138(7):1627-1635.
Spranger S, et al. Up-regulation of PD-L1, IDO, and T(regs) in the melanoma tumor microenvironment is driven by CD8(+) T cells. Sci Transl Med. 2013;5(200):200ra116.
Steele CW, et al. CXCR2 inhibition profoundly suppresses metastases and augments immunotherapy in pancreatic ductal adenocarcinoma. Cancer Cell. 2016;29(6):832-845.
Swanson KV, et al. The NLRP3 inflammasome: molecular activation and regulation to therapeutics. Nat Rev Immunol. 2019;19(8):477-489.
Tu S, et al. Overexpression of interleukin-1beta induces gastric inflammation and cancer and mobilizes myeloid-derived suppressor cells in mice. Cancer Cell. 2008;14(5):408-419.
Van Deventer HW, et al. The inflammasome component NLRP3 impairs antitumor vaccine by enhancing the accumulation of tumor-associated myeloid-derived suppressor cells. Cancer Res. 2010;70(24):10161-10169.
Wang G, et al. Targeting YAP-dependent MDSC infiltration impairs tumor progression. Cancer Discov. 2016;6(1):80-95.
Weber J, et al. Phase I/II study of metastatic melanoma patients treated with nivolumab who had progressed after ipilimumab. Cancer Immunol Res. 2016;4(4):345-353.
Zhao F, et al. Paracrine Wnt5a-ß-catenin signaling triggers a metabolic program that drives dendritic cell tolerization. Immunity. 2018;48(1):147-160.e7.
Zhao F, et al. Stromal fibroblasts mediate anti-PD-1 resistance via MMP-0 and dictate TGFß inhibitor sequencing in melanoma. Cancer Immunol Res. 2018;6(12):1459-1471.
Zhao X, et al. Intrinsic resistance of solid tumors to immune checkpoint blockade therapy. Cancer Res. 2017;77(4):817-822.

\* cited by examiner

B. *Lewis Lung Carcinoma*

*Orthotopic KPC4662 Pancreatic Cancer*

*Autologous Humanized Model of Renal Cell Carcinoma*

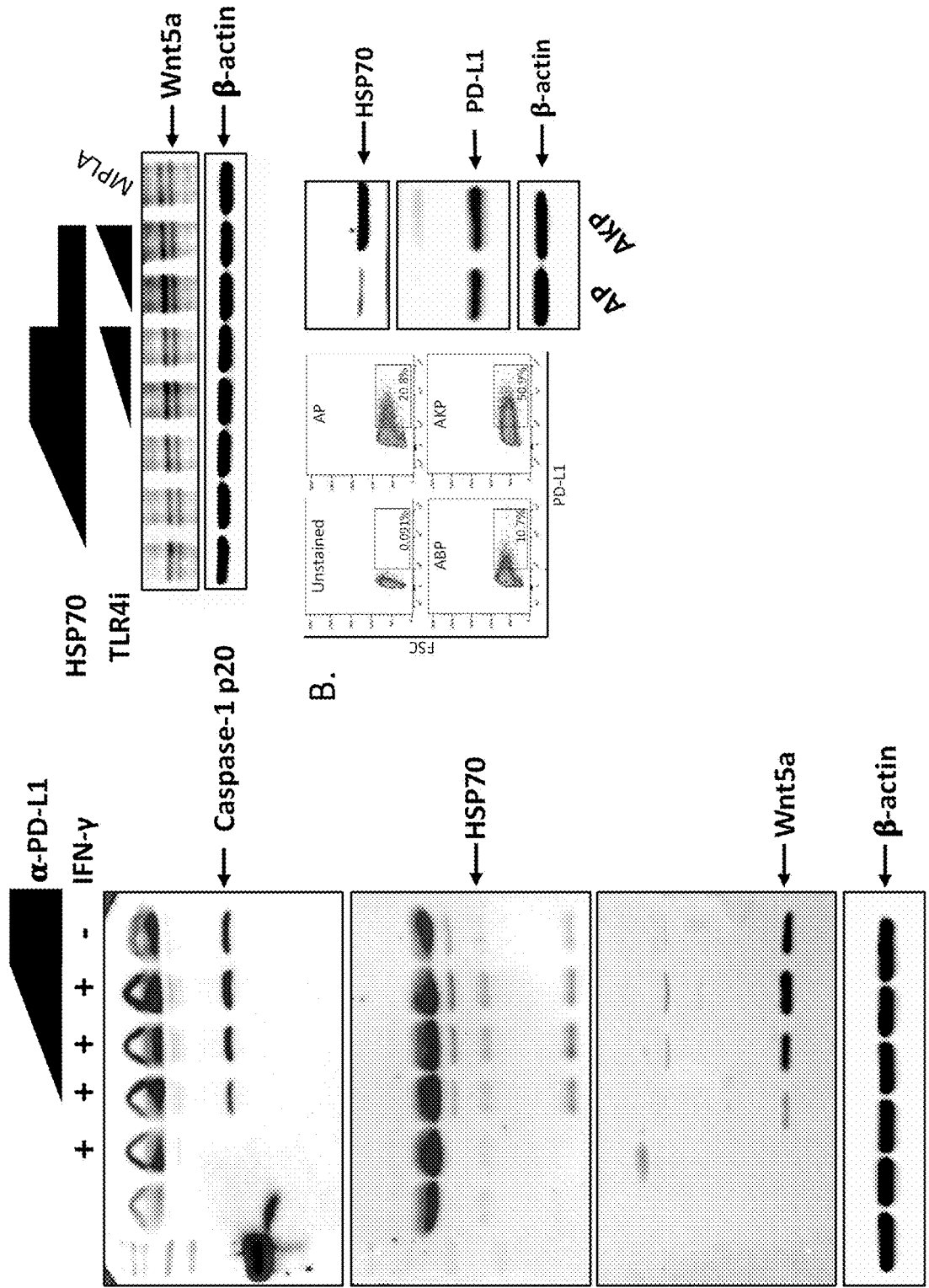
Figure 15A-B

SEQUENCE LISTING

<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: synthetic

<400> SEQUENCE: 1
ggctgtattc ccctccatcg                    20

<210> SEQ ID NO 2

<211> LENGTH: 22
<212> TYPE: DNA
<213> ORGANISM: Artificial Sequence
<220> FEATURE:
<223> OTHER INFORMATION: synthetic

<400> SEQUENCE: 2
ccagttggta acaatgccat gt                                              22

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
acaaagtgcg aggaaggaga                                                 20

<210> SEQ ID NO 4
<211> LENGTH: 20
<212> TYPE: DNA
<213> ORGANISM: Artificial Sequence
<220> FEATURE:
<223> OTHER INFORMATION: synthetic

<400> SEQUENCE: 4
tttggctttg cagccttaat                                                 20

<210> SEQ ID NO 5
<211> LENGTH: 20
<212> TYPE: DNA
<213> ORGANISM: Artificial Sequence
<220> FEATURE:
<223> OTHER INFORMATION: synthetic

<400> SEQUENCE: 5
aacactcccc tgacaaccag                                                 20

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
ccagcaggta gctgaaggtc                                                 20

<210> SEQ ID NO 7
<211> LENGTH: 22
<212> TYPE: DNA
<213> ORGANISM: Artificial Sequence
<220> FEATURE:
<223> OTHER INFORMATION: synthetic

<400> SEQUENCE: 7
tttgtttttg cagatgattc aa                                              22

<210> SEQ ID NO 8
<211> LENGTH: 19
<212> TYPE: DNA
<213> ORGANISM: Artificial Sequence
<220> FEATURE:
<223> OTHER INFORMATION: synthetic -continued

<400> SEQUENCE: 8
tgccatcata aaggagcca                                                    19

<210> SEQ ID NO 9
<211> LENGTH: 21
<212> TYPE: DNA
<213> ORGANISM: Artificial Sequence
<220> FEATURE:
<223> OTHER INFORMATION: synthetic

<400> SEQUENCE: 9
tgagctgcgc tgtcagtgcc t                                                 21

<210> SEQ ID NO 10
<211> LENGTH: 21
<212> TYPE: DNA
<213> ORGANISM: Artificial Sequence
<220> FEATURE:
<223> OTHER INFORMATION: synthetic

<400> SEQUENCE: 10
agaagccgac gttcacccag a                                                 21

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
gagcttgagt gtgacgcccc cagg                                              24

<210> SEQ ID NO 12
<211> LENGTH: 25
<212> TYPE: DNA
<213> ORGANISM: Artificial Sequence
<220> FEATURE:
<223> OTHER INFORMATION: synthetic

<400> SEQUENCE: 12
gttagccttg cctttgttca gtatc                                             25

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
gcatttctgt tgctgttcac gctg                                              24

<210> SEQ ID NO 14
<211> LENGTH: 25
<212> TYPE: DNA
<213> ORGANISM: Artificial Sequence
<220> FEATURE:
<223> OTHER INFORMATION: synthetic

<400> SEQUENCE: 14
cctccttctg gtttttcagt ttagc                                             25

<210> SEQ ID NO 15

```
<211> LENGTH: 24
<212> TYPE: DNA
<213> ORGANISM: Artificial Sequence
<220> FEATURE:
<223> OTHER INFORMATION: synthetic

<400> SEQUENCE: 15
agcaaacacc tctactaccc tcta                                              24

<210> SEQ ID NO 16
<211> LENGTH: 23
<212> TYPE: DNA
<213> ORGANISM: Artificial Sequence
<220> FEATURE:
<223> OTHER INFORMATION: synthetic

<400> SEQUENCE: 16
gggctgcatc aattcaaata cca                                               23

<210> SEQ ID NO 17
<211> LENGTH: 24
<212> TYPE: DNA
<213> ORGANISM: Artificial Sequence
<220> FEATURE:
<223> OTHER INFORMATION: synthetic

<400> SEQUENCE: 17
gtctacatgt tccagtatga ctcc                                              24

<210> SEQ ID NO 18
<211> LENGTH: 25
<212> TYPE: DNA
<213> ORGANISM: Artificial Sequence
<220> FEATURE:
<223> OTHER INFORMATION: synthetic

<400> SEQUENCE: 18
agtgagttgt catatttctc gtggt                                             25

<210> SEQ ID NO 19
<211> LENGTH: 25
<212> TYPE: DNA
<213> ORGANISM: Artificial Sequence
<220> FEATURE:
<223> OTHER INFORMATION: synthetic

<400> SEQUENCE: 19
agtgagttgt catatttctc gtggt                                             25

<210> SEQ ID NO 20
<211> LENGTH: 21
<212> TYPE: DNA
<213> ORGANISM: Artificial Sequence
<220> FEATURE:
<223> OTHER INFORMATION: synthetic

<400> SEQUENCE: 20
gccagcctcg tgttttattc c                                                 21

<210> SEQ ID NO 21
<211> LENGTH: 19
<212> TYPE: DNA
<213> ORGANISM: Artificial Sequence
<220> FEATURE:
<223> OTHER INFORMATION: synthetic
```

```
<400> SEQUENCE: 21
gaccagctgg acaacatac                                                   19

<210> SEQ ID NO 22
<211> LENGTH: 19
<212> TYPE: DNA
<213> ORGANISM: Artificial Sequence
<220> FEATURE:
<223> OTHER INFORMATION: synthetic

<400> SEQUENCE: 22
gaccagctgg acaacatac                                                   19

<210> SEQ ID NO 23
<211> LENGTH: 20
<212> TYPE: DNA
<213> ORGANISM: Artificial Sequence
<220> FEATURE:
<223> OTHER INFORMATION: synthetic

<400> SEQUENCE: 23
ctacattgat gctgccttgg                                                  20

<210> SEQ ID NO 24
<211> LENGTH: 20
<212> TYPE: DNA
<213> ORGANISM: Artificial Sequence
<220> FEATURE:
<223> OTHER INFORMATION: synthetic

<400> SEQUENCE: 24
atccgtcact gctcacacag                                                  20

<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
cactgcccaa gattgctaca                                                  20

<210> SEQ ID NO 26
<211> LENGTH: 20
<212> TYPE: DNA
<213> ORGANISM: Artificial Sequence
<220> FEATURE:
<223> OTHER INFORMATION: synthetic

<400> SEQUENCE: 26
cttcactcag caccagacca                                                  20

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
gtggtgaccc tctgtgaggt                                                  20

<210> SEQ ID NO 28
```

```
<211> LENGTH: 20
<212> TYPE: DNA
<213> ORGANISM: Artificial Sequence
<220> FEATURE:
<223> OTHER INFORMATION: synthetic

<400> SEQUENCE: 28
tcttcctgga gcgcttctaa                                                    20

<210> SEQ ID NO 29
<211> LENGTH: 23
<212> TYPE: DNA
<213> ORGANISM: Artificial Sequence
<220> FEATURE:
<223> OTHER INFORMATION: synthetic

<400> SEQUENCE: 29
atactctagg aaggaaggac acc                                                23

<210> SEQ ID NO 30
<211> LENGTH: 23
<212> TYPE: DNA
<213> ORGANISM: Artificial Sequence
<220> FEATURE:
<223> OTHER INFORMATION: synthetic

<400> SEQUENCE: 30
tccatgatgt catttatgag ggc                                                23

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
caatgtggaa acaacgtgga                                                    20

<210> SEQ ID NO 32
<211> LENGTH: 20
<212> TYPE: DNA
<213> ORGANISM: Artificial Sequence
<220> FEATURE:
<223> OTHER INFORMATION: synthetic

<400> SEQUENCE: 32
tgtaactttg ggggaagctg                                                    20

<210> SEQ ID NO 33
<211> LENGTH: 20
<212> TYPE: DNA
<213> ORGANISM: Artificial Sequence
<220> FEATURE:
<223> OTHER INFORMATION: synthetic

<400> SEQUENCE: 33
aagaggaagc ccaagaaagc                                                    20

<210> SEQ ID NO 34
<211> LENGTH: 20
<212> TYPE: DNA
<213> ORGANISM: Artificial Sequence
<220> FEATURE:
<223> OTHER INFORMATION: synthetic
```

```
<400> SEQUENCE: 34
cgatggaatc gatgatgttg                                            20

<210> SEQ ID NO 35
<211> LENGTH: 20
<212> TYPE: DNA
<213> ORGANISM: Artificial Sequence
<220> FEATURE:
<223> OTHER INFORMATION: synthetic

<400> SEQUENCE: 35
cacaggctga gcagtttgaa                                            20

<210> SEQ ID NO 36
<211> LENGTH: 20
<212> TYPE: DNA
<213> ORGANISM: Artificial Sequence
<220> FEATURE:
<223> OTHER INFORMATION: synthetic

<400> SEQUENCE: 36
tttcggcttc ttttgatgct                                            20

<210> SEQ ID NO 37
<211> LENGTH: 21
<212> TYPE: DNA
<213> ORGANISM: Artificial Sequence
<220> FEATURE:
<223> OTHER INFORMATION: synthetic

<400> SEQUENCE: 37
gcctcttctc attcctgctt g                                          21

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
ctgatgagag ggaggccatt                                            20

<210> SEQ ID NO 39
<211> LENGTH: 20
<212> TYPE: DNA
<213> ORGANISM: Artificial Sequence
<220> FEATURE:
<223> OTHER INFORMATION: synthetic

<400> SEQUENCE: 39
aagttccggg gaatctgttt                                            20

<210> SEQ ID NO 40
<211> LENGTH: 20
<212> TYPE: DNA
<213> ORGANISM: Artificial Sequence
<220> FEATURE:
<223> OTHER INFORMATION: synthetic

<400> SEQUENCE: 40
gcatagcctg agcctgtttc                                            20

<210> SEQ ID NO 41
```

```
<211> LENGTH: 20
<212> TYPE: DNA
<213> ORGANISM: Artificial Sequence
<220> FEATURE:
<223> OTHER INFORMATION: synthetic

<400> SEQUENCE: 41
ttcccaatac caccgttctc                                               20

<210> SEQ ID NO 42
<211> LENGTH: 20
<212> TYPE: DNA
<213> ORGANISM: Artificial Sequence
<220> FEATURE:
<223> OTHER INFORMATION: synthetic

<400> SEQUENCE: 42
ctatgtgctg gagggtcaca                                               20

<210> SEQ ID NO 43
<211> LENGTH: 20
<212> TYPE: DNA
<213> ORGANISM: Artificial Sequence
<220> FEATURE:
<223> OTHER INFORMATION: synthetic

<400> SEQUENCE: 43
aatccacagg ctcacccata                                               20

<210> SEQ ID NO 44
<211> LENGTH: 20
<212> TYPE: DNA
<213> ORGANISM: Artificial Sequence
<220> FEATURE:
<223> OTHER INFORMATION: synthetic

<400> SEQUENCE: 44
caggtaccaa gggatgtcct                                               20

<210> SEQ ID NO 45
<211> LENGTH: 20
<212> TYPE: DNA
<213> ORGANISM: Artificial Sequence
<220> FEATURE:
<223> OTHER INFORMATION: synthetic

<400> SEQUENCE: 45
gacatggccc ctaatttcct                                               20

<210> SEQ ID NO 46
<211> LENGTH: 20
<212> TYPE: DNA
<213> ORGANISM: Artificial Sequence
<220> FEATURE:
<223> OTHER INFORMATION: synthetic

<400> SEQUENCE: 46
gacccagaag tcctcatgga                                               20

<210> SEQ ID NO 47
<211> LENGTH: 20
<212> TYPE: DNA
<213> ORGANISM: Artificial Sequence
<220> FEATURE:
<223> OTHER INFORMATION: synthetic
```

```
<400> SEQUENCE: 47
actgagcacc cctgcttcta                                              20

<210> SEQ ID NO 48
<211> LENGTH: 20
<212> TYPE: DNA
<213> ORGANISM: Artificial Sequence
<220> FEATURE:
<223> OTHER INFORMATION: synthetic

<400> SEQUENCE: 48
agattagtca gcggcaggaa                                              20

<210> SEQ ID NO 49
<211> LENGTH: 25
<212> TYPE: DNA
<213> ORGANISM: Artificial Sequence
<220> FEATURE:
<223> OTHER INFORMATION: synthetic

<400> SEQUENCE: 49
atggcaactg ttcctgaact caact                                        25

<210> SEQ ID NO 50
<211> LENGTH: 26
<212> TYPE: DNA
<213> ORGANISM: Artificial Sequence
<220> FEATURE:
<223> OTHER INFORMATION: synthetic

<400> SEQUENCE: 50
caggacaggt atagattctt tccttt                                       26

<210> SEQ ID NO 51
<211> LENGTH: 22
<212> TYPE: DNA
<213> ORGANISM: Artificial Sequence
<220> FEATURE:
<223> OTHER INFORMATION: synthetic

<400> SEQUENCE: 51
gactcttgcg tcaacttcaa gg                                           22

<210> SEQ ID NO 52
<211> LENGTH: 21
<212> TYPE: DNA
<213> ORGANISM: Artificial Sequence
<220> FEATURE:
<223> OTHER INFORMATION: synthetic

<400> SEQUENCE: 52
caggctgtct tttgtcaacg a                                            21

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
gcctcttctc attcctgctt g                                            21

<210> SEQ ID NO 54
```

```
<211> LENGTH: 20
<212> TYPE: DNA
<213> ORGANISM: Artificial Sequence
<220> FEATURE:
<223> OTHER INFORMATION: synthetic

<400> SEQUENCE: 54
ctgatgagag ggaggccatt                                               20

<210> SEQ ID NO 55
<211> LENGTH: 20
<212> TYPE: DNA
<213> ORGANISM: Artificial Sequence
<220> FEATURE:
<223> OTHER INFORMATION: synthetic

<400> SEQUENCE: 55
gcaacaacgc catctatgag                                               20

<210> SEQ ID NO 56
<211> LENGTH: 20
<212> TYPE: DNA
<213> ORGANISM: Artificial Sequence
<220> FEATURE:
<223> OTHER INFORMATION: synthetic

<400> SEQUENCE: 56
atctttgctg tcacaagagc                                               20
```

METHODS OF TREATMENT OF SPECIFIC CANCERS WITH NLRP3 INHIBITORS AND ANTI-PD1/PD-L1 ANTIBODIES

CROSS-REFERENCE TO RELATED APPLICATIONS

This application claims priority to U.S. Provisional Application No. 62/899,965, filed Sep. 13, 2019, the contents of which are incorporated by reference.

STATEMENT REGARDING FEDERALLY SPONSORED RESEARCH

This invention was made with government support under CA249085 awarded by the National Institutes of Health. The government has certain rights in the invention.

BACKGROUND OF THE INVENTION

Despite the significant impact that checkpoint inhibitor immunotherapies have generated in clinical oncology, the majority of cancer patients still do not benefit from this treatment modality. It is widely believed that a more intimate understanding of the underlying mechanisms driving cancer immunotherapy resistance will lead to the discovery and development of innovative strategies to augment the efficacy of immunotherapy while expanding the patient population capable of benefitting from these agents. However, the understanding of the mechanisms driving both primary and secondary immunotherapy resistance remains incomplete.

There is an extensive body of literature describing the inhibitory role of myeloid-derived suppressor cells (MDSCs) in the generation of adaptive T cell immunity. These data are consistent with additional studies that have correlated elevated circulating MDSC levels with poor clinical responses to both anti-cytotoxic T lymphocyte antigen-4 (CTLA-4) and anti-program death-1 (PD-1) antibody immunotherapy in advanced melanoma patients. MDSCs have been shown to undergo chemotaxis toward tumor beds via chemokine gradients generated by the developing tumor. In particular, migration of the granulocytic subset of MDSCs (PMN-MDSCs) seems to rely primarily on the chemokine receptor, CXCR2, and several of its cognate ligands, including CXCL5. Additional work has shown that CXCR2 blockade enhances the efficacy of anti-PD-1 ab immunotherapy in models of both pancreatic cancer and sarcoma. These findings suggest that this immunosuppressive cell population plays a critical role in determining the outcome for those cancer patients undergoing anti-PD-1 ab therapy. However, the exact mechanism by which MDSCs interfere with the development of anti-tumor immunity in response to checkpoint inhibitor immunotherapy is unclear.

It is well known that the immune system is comprised of many negative feedback inhibitory pathways which serve to suppress the development of overzealous immune responses to avoid autoimmune pathology. Similar mechanisms are likely to serve as the molecular underpinnings for the development of adaptive resistance to anti-PD-1 antibody immunotherapy and represent key pathways of interest for the future development of novel combinatorial immunotherapy strategies. Indeed, recent studies have demonstrated both CD8+ T cell-dependent and interferon-dependent upregulation of colony-stimulating factor-1 in melanoma and CD38 in lung cancer promote adaptive resistance to anti-PD-1 checkpoint blockade. These observations are reminiscent of the interferon-dependent upregulation of the immunoregulatory enzyme, indoleamine 2,3-dioxygenase (IDO), which serves to re-establish immune tolerance in response to cytolytic T cell activity. While a recent study has implicated tumor expression of CXCL1 and the recruitment of PMN-MDSCs as key factors that mediate against tumor T cell infiltration, a role for CXCR2-dependent chemokines in the generation of adaptive resistance to anti-PD-1 antibody immunotherapy has not been described.

Previous work, including the work of the Inventors, has demonstrated the Wnt5a ligand to be associated with tumor progression, immune evasion, and immunotherapy resistance. Interestingly, toll-like receptor-4 (TLR4) signaling regulates Wnt5a expression in myeloid cells and has also been associated with tumor progression in a variety of cancer types.

Reports of tumor intrinsic signaling pathways induced by PD-L1 have emerged, linking PD-L1 with the promotion of epithelial-to-mesenchymal transition (EMT), the stimulation of the mTOR-Akt anti-apoptotic pathway, as well as with the inhibition of interferon-dependent apoptosis. While each of these pathways may be pro-tumorigenic, there are no known associations between PD-L1 and the induction of adaptive resistance to anti-PD-1 antibody immunotherapy via the stimulation of tumor intrinsic signaling pathways. While many groups have described the role of NOD-, LRR- and pyrin domain-containing protein-3 (NLRP3) as a sensor for pathogen-derived danger signals by antigen-presenting cells in the innate immune system, relatively little is known about the contribution of NLRP3 to tumorigenesis and its role in modulating tumor responses to immunotherapy has not been explored.

SUMMARY OF THE INVENTION

The present disclosure is based, in part on the discovery by the inventors that CD8+ T cell activation in response to PD-1 blockade induces a PD-L-NLRP3 inflammasome signaling cascade that ultimately leads to the recruitment of granulocytic myeloid-derived suppressor cells (PMN-MDSCs) into tumor tissues and that the genetic and pharmacologic inhibition of NLRP3 suppresses PMN-MDSC tumor infiltration and significantly augments the efficacy of anti-PD-1 antibody immunotherapy.

Accordingly, one aspect of the present disclosure provides a method of treating a cancer in a subject, the method comprising, consisting of, or consisting essentially of administering to the subject a therapeutically effective amount of an NLRP3 inhibitor and at least one checkpoint inhibitor such that the cancer is treated in the subject. In some aspects, the checkpoint inhibitor is PD-1 inhibitor, preferably an anti-PD-1 antibody.

In some embodiments, the cancer comprises a cancer resistant to immune checkpoint inhibitors. In certain embodiments, the cancer comprises a cancer that is resistant to anti-PD-1 immunotherapy. In some embodiments, the cancer is melanoma, and in some examples, the melanoma is refractory to anti-PD-1 immunotherapy.

In some embodiments, the NLRP3 inhibitor is selected from the group consisting of antibodies, small molecules, peptides, miRNAs, siRNAs, oligonucleotides, cytokines, agonists, and combinations thereof. In certain embodiments, the NLRP3 inhibitor is selected from the group consisting of Z-VAD-FMK, MCC950, BHB, Resveratrol, Arglabin, CB2R agonist, miRNA-223, beta-hydroxybutyrate, Type I interferon, IFN-beta, JC124, CY09, dapansutrile (OLT1177), and the like.

In another embodiment, the checkpoint inhibitor comprises a PD-1 inhibitor. In some cases, the PD-1 inhibitor comprises an antibody. In other embodiments, the PD-1 inhibitor is selected from the group consisting of Nivolumab (anti-PD-1), Pembrolizumab (anti-PD-1), and combinations thereof. In some embodiments the checkpoint inhibitor comprises a PD-L1 inhibitor. Suitable PD-L1 inhibitors include, for example, a PD-L1 inhibitor selected from the group consisting of atezolizumab, avelumab, durvalumab, and combinations thereof.

Another embodiment of the present disclosure provides a method of increasing the efficacy of anti-PD-1 or anti-PD-L1 antibody immunotherapy comprising, consisting of, or consisting essentially of administering to the subject a therapeutically effective amount of an NLRP3 inhibitor together with an anti-PD-1 therapy (e.g., anti-PD-1 antibody) or anti-PD-L1 therapy (e.g., anti-PD-L1 antibody) such that the cancer is treated in the subject.

In some embodiments, the checkpoint inhibitors are administered prior to the NLRP3 inhibitor. In other embodiments, the checkpoint inhibitors are administered concurrently with the NLRP3 inhibitor. In yet other embodiments, the checkpoint inhibitors are administered after the NLRP3 inhibitor.

In another embodiment, the method further comprises administering another anti-cancer therapy.

In another aspect, the present disclosure provides a method of treating a subject who is refractory or not responding to anti-PD-1 or anti-PD-L1 treatment, the method comprising administering to the subject a therapeutically effective amount of an NLRP3 inhibitor and an anti-PD-1 antibody or anti-PD-L1 antibody such that the cancer is treated in the subject. In some embodiments, the method comprises selecting a subject that was previously treated with PD-1 or PD-L1 inhibitor and was resistant to treatment.

Another aspect of the present disclosure provides all that is described and illustrated herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Figures 1A, 1B, 1C, 1D, 1E:
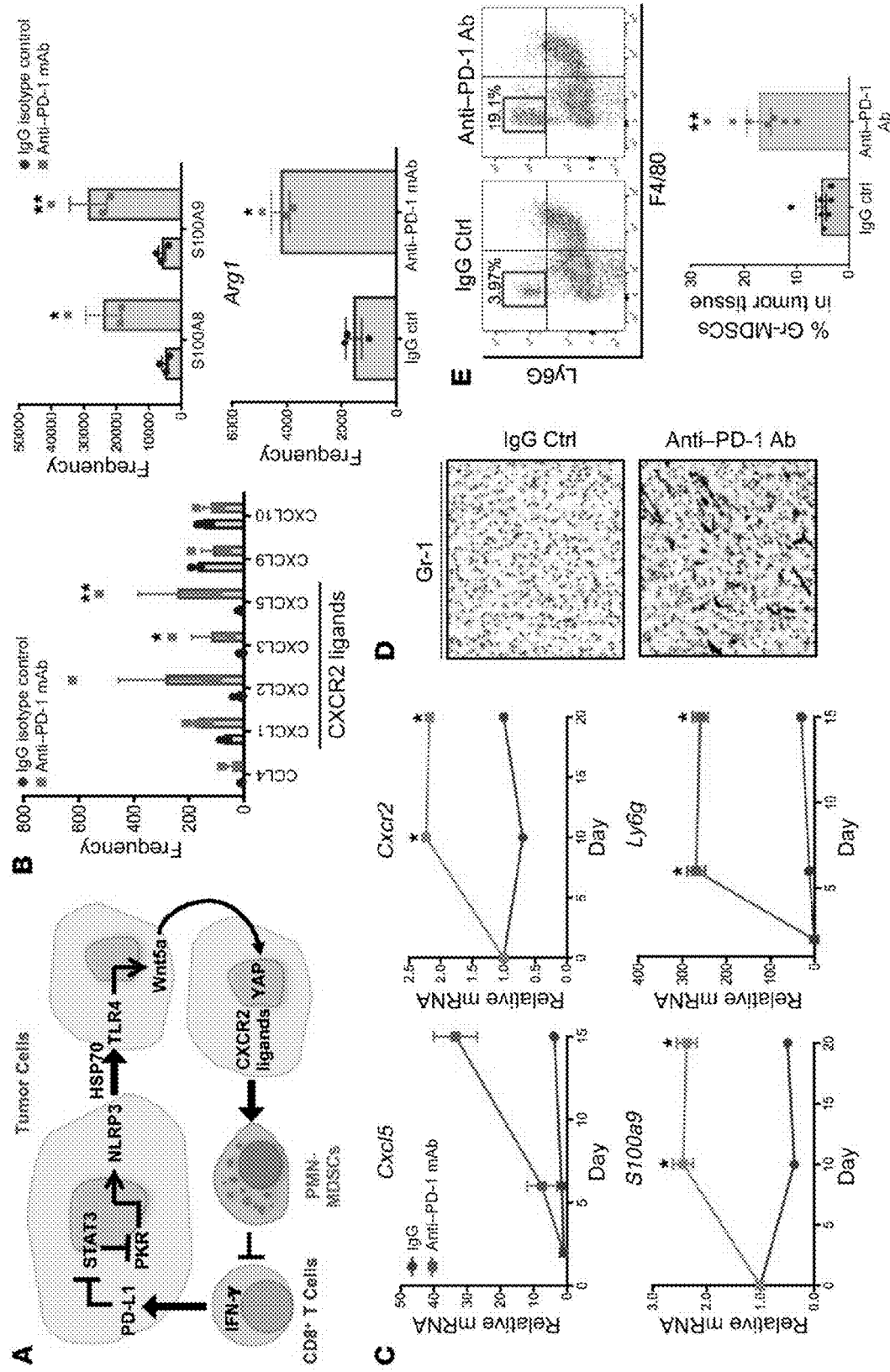
FIG. 1A-H. PMN-MDSC accumulation contributes to tumor progression following anti-PD-1 Ab immunotherapy. (A) Schematic overview of the adaptive resistance pathway. (B) RNA-Seq differential gene expression analysis of tumor tissues following treatment of the autochthonous BRAFV600E PTEN−/− melanoma model with anti-PD-1 Ab therapy versus IgG isotype control (Ctrl) (n=3). (C) qRT-PCR analysis of target genes of interest in serial tumor fine-needle aspiration (FNA) biopsy specimens harvested from the transgenic BRAFV600E PTEN−/− melanoma model treated with anti-PD-1 Ab versus IgG isotype control (n=5). (D) Gr-1 immunohistochemical analysis of transgenic BRAFV600E PTEN−/− melanoma tissues following treatment with anti-PD-1 Ab versus IgG isotype control. Original magnification, ×40. Gr-1 staining is shown in red. Images are representative of 3 tumors per group. (E) PMN-MDSC flow cytometric analysis of transgenic BRAFV600E PTEN−/− melanoma tissues following treatment with anti-PD-1 Ab versus IgG isotype control. PMN-MDSCs were defined as live+CD45+CD11b+Ly6G+Ly6CintF4/80− cells. Shown are a representative flow dot plot and quantification graph of PMN-MDSC flow cytometric data (n=5). (F) qRT-PCR analysis of CXCR2 ligands in BRAFV600E PTEN−/− melanoma tissues treated with anti-PD-1 Ab following CD8+ T cell ablation in vivo (n=3). (G) In vivo tumor study of BRAFV600E PTEN−/− melanoma genetically silenced for CXCL5. Quantitation of tumor-infiltrating PMN-MDSCs by flow cytometry is shown along with an in vivo tumor growth curve of CXCL5-silenced BRAFV600E PTEN−/− melanoma versus BRAFV600E PTEN−/− NTC melanoma control tumors treated with anti-PD-1 Ab. Data were normalized to tumors treated with IgG isotype control (n=5). (H) Combination treatment with anti-PD-1 Ab and CXCR2 inhibitor (CXCR2i) in an in vivo BRAFV600E PTEN−/− melanoma study (n=5). Graphs show flow cytometric analysis of tumor-infiltrating PMN-MDSCs and live+ CD45+CD3+CD8+ T cells. *$P<0.05$, $P<0.005$, and *$P<0.0005$, by Student's t test with Holm-Sidak post hoc correction for multiple comparisons (B, C, and F), Student's t test (E and G), or 1-way ANOVA with Sidak's post hoc multiple comparisons test (H). See also FIGS. 8, 9, and 12C.

Flow cytometric analysis of PMN-MDSCs in resected BRAFV600E PTEN−/− NTC and BRAFV600E PTEN−/− NLRP3KD melanomas (n=5). (D) Tumor growth curve of BRAFV600E PTEN−/− NTC and BRAFV600E PTEN−/− NLRP3KD melanomas (n=5). (E) Treatment of syngeneic BRAFV600E PTEN−/− melanomas with IgG isotype control Ab (200 μg i.p. every 3 days), NLRP3 inhibitor (10 g MCC950 i.p. every 3 days), anti-PD-1 Ab (200 μg i.p. every 3 days), or NLRP3 inhibitor and anti-PD-1 Ab combination therapy (n=8). (F) Representative flow cytometric dot plots of PMN-MDSCs and CD8+ T cells in resected BRAFV600E PTEN−/− melanomas following treatment with IgG isotype control Ab, NLRP3 inhibitor, anti-PD-1 Ab, or NLRP3 inhibitor and anti-PD-1 Ab combination therapy. Graphs show flow cytometric analysis of tumor-infiltrating PMN-MDSCs and CD44+CD8+ T cells. (G) Whole tumor tissue Western blot analysis for pro-caspase-1, caspase-1 p20, and Wnt5a following in vivo treatment with IgG isotype control, anti-PD-1 Ab, or combined anti-PD-1 Ab and NLRP3 inhibitor. Blots are representative of 2 independent experiments. (H) qRT-PCR analysis of Cxcl5 and granzyme B (Gzmb) expression in resected BRAFV600E PTEN−/− melanoma tissues (n=5). *$P<0.05$, $P<0.005$, and *$P<0.0005$, by Student's t test (A-D) and 1-way ANOVA with Sidak's post hoc multiple comparisons test (E, F, and H). See also FIG. 14.

FIG. 7A-G. The PD-L1/NLRP3/HSP70 PMN-MDSC adaptive recruitment pathway in human melanoma. (A) Supernatant HSP70 and caspase-1 p20 Western blot analysis following treatment of human WM266 melanoma cells with IFN-γ with or without anti-PD-L1 Ab. Blots are representative of 3 independent experiments. (B) Wnt5A Western blot analysis of HSP70-treated human WM266 melanoma cells with or without TLR4 inhibitor. Blots are representative of 3 independent experiments. (C) HSP70 and caspase-1 p20 Western blot analysis following treatment of human WM266 melanoma cells with ATP in the absence and presence of MCC950. Blots are representative of 2 independent experiments. (D) Cytolytic T cell markers correlated with ITGAM (CD11B), CD33, and NLRP3 gene expression in the melanoma TCGA-SKCM database. (E) RNA-Seq analysis of human melanoma tissue specimens collected before anti-PD-1 Ab therapy and at the time of disease progression on anti-PD-1 Ab therapy. TPM, transcripts per million. (F) Plasma HSP70 ELISA at week 0 and week 12 in patients with advanced melanoma undergoing anti-PD-1 Ab immunotherapy. (G) Change in HSP70 plasma levels following anti-PD-1 Ab immunotherapy in patients with advanced melanoma who were responders (R) or nonresponders (NR). The response was based on week-12 CT imaging. HSP70 changes were normalized to target tumor burden based on week-12 CT imaging. In the box-and-whisker plots, the central line represents the median, the box represents the first and third quartiles, and the error bars represent the data range. *$P<0.05$ and **$P<0.005$, by Student's t test (E and G).

FIG. 8A-D. PMN-MDSC Recruitment to Tumor Tissues in Response to Anti-PD-1 Antibody Immunotherapy. (A) top left, typical tumor growth curve of autochthonous BRAFV600EPTEN−/−melanoma model undergoing anti-PD-1 ab therapy. Box represents escape phase following initial treatment response. RNAseq differential gene expression analysis of resected tumor tissues following treatment of the autochthonous BRAFV600EPTEN−/− melanoma model with anti-PD-1 ab therapy (200 μg ip every 3 days) versus IgG isotype control (n=3/group). Cd8a, Prf1, Gzmb are genes associated with cytolytic T cells. (B) Top, PMN-MDSC flow cytometry analysis of resected LLC1 Lewis lung carcinoma tumors following progression through anti-PD-1 ab therapy or IgG isotype control (n=5). Middle, Ly6G IHC (red) of resected orthotopic KPC4662 pancreatic cancer model following treatment with either anti-PD-1 ab therapy or IgG isotype control. Representative of 3 tumors analyzed per group. Bottom, PMN-MDSC Flow cytometry analysis (HLA-DR-CD14−CD33+CD11b+CD15+) of resected human xenograft renal cell carcinoma tissue from autologous humanized mice following treatment with either anti-PD-1 ab therapy or IgG isotype control (n=3). (C) Ly6G IHC (pink) of resected autochthonous BRAFV600EPTEN−/− melanoma tissue following anti-CTLA-4 ab, anti-PD-1 ab, and IgG isotype control treatment. 20×. Representative of 3 tumors per group. (D) Qrt-PCR analysis of FACS sorted PMN-MDSCs (CD45+CDiib+Ly6C-Ly6G+F4/80−) and tumor associated macrophages (CD45+CDiib+Ly6CintLy6G-F4/80+) isolated from anti-PD-1 ab-treated autochthonous BRAFV600EPTEN−/− melanomas. Representative of 2 independent experiments. All data is mean±SEM. Significance assessed using Student's t test in panels A,B. *$P<0.05$. Related to FIG. 1.

FIG. 9A-D. Genetic Silencing of CXCL5 Promotes Tumor and Tumor-draining Lymph Node Infiltration of CD8+ T. Cells. (A) Top, Western blot analysis of control (NTC) and CXCL5-silenced (CXCL5KD) BRAFV600E-PTEN−/−melanoma cell lines. Bottom, Dot blot analysis of supernatant (SNT) isolated from control (NTC) and CXCL5-silenced (CXCL5KD) BRAFV600E-PTEN−/− melanoma cell lines. NTC, non-target control. KD, knockdown. (B) CD8+ T cell flow cytometry analysis (CD45+CD3+CD8+) of BRAFV600E-PTEN−/−-NTC and BRAFV600EPTEN−/−-CXCL5KD melanoma tissues and tumor-draining lymph node (TLDN) tissues. Left, representative flow dot plots. Right, quantitation of CD8+ T cell flow cytometry data. Representative of 2 mice per group. (C) PMN-MDSC flow cytometry analysis of BRAFV600E-PTEN−/−-NTC and BRAFV600EPTEN−/−-CXCL5KD melanoma tissues. Representative flow dot plots. (D) Tumor volume change rate during CXCR2i therapy described in FIG. 1F. Box represents escape phase in the autochthonous BRAFV600E-PTEN−/− melanoma model which occurs concurrently with PMN-MDSC infiltration (n=5/group). All data is mean±SEM. Significance assessed using Student's t test in panel B. *$P<0.05$. Related to FIG. 1.

Figures 10A, 10B:
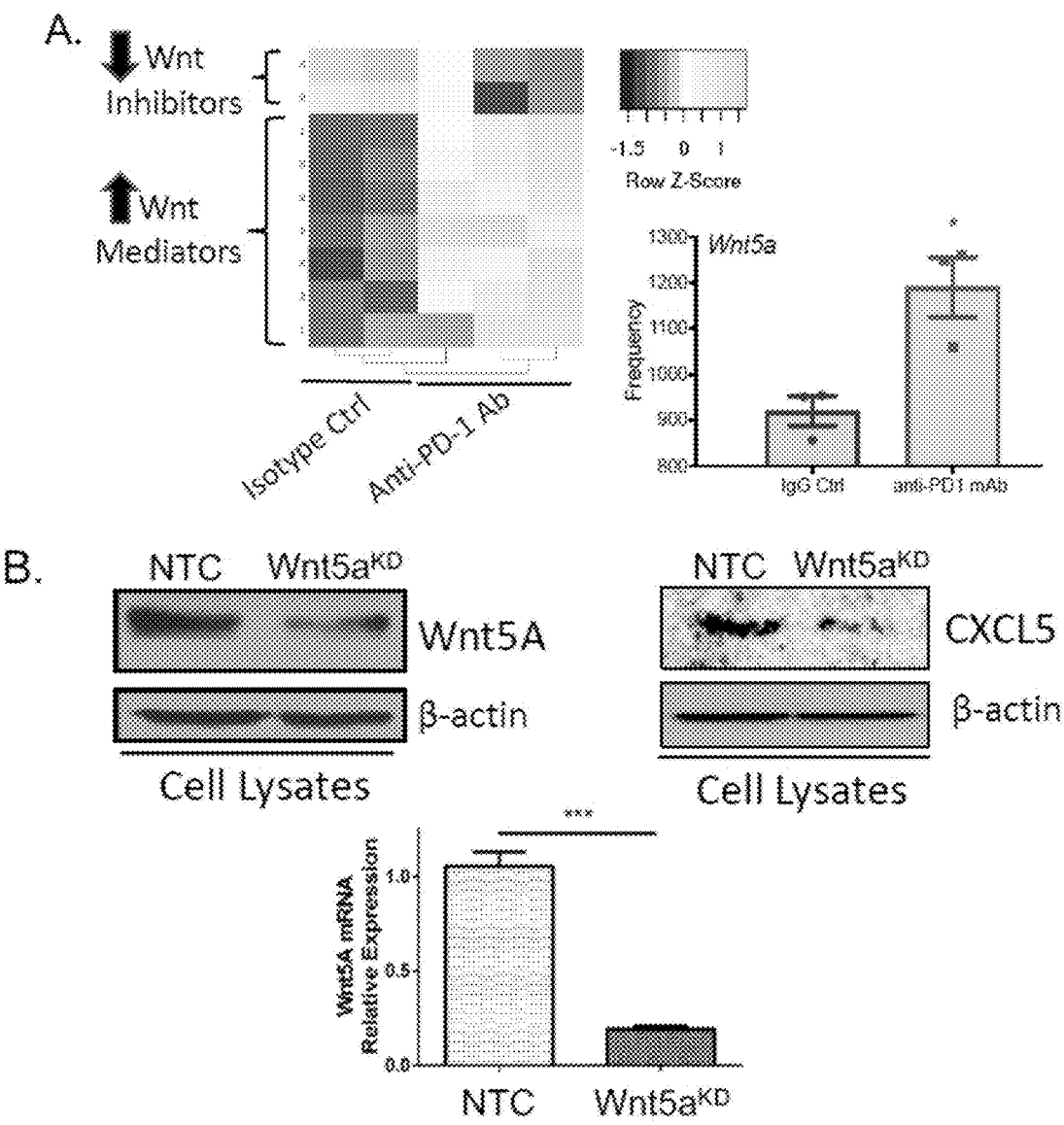
Figure 10C:
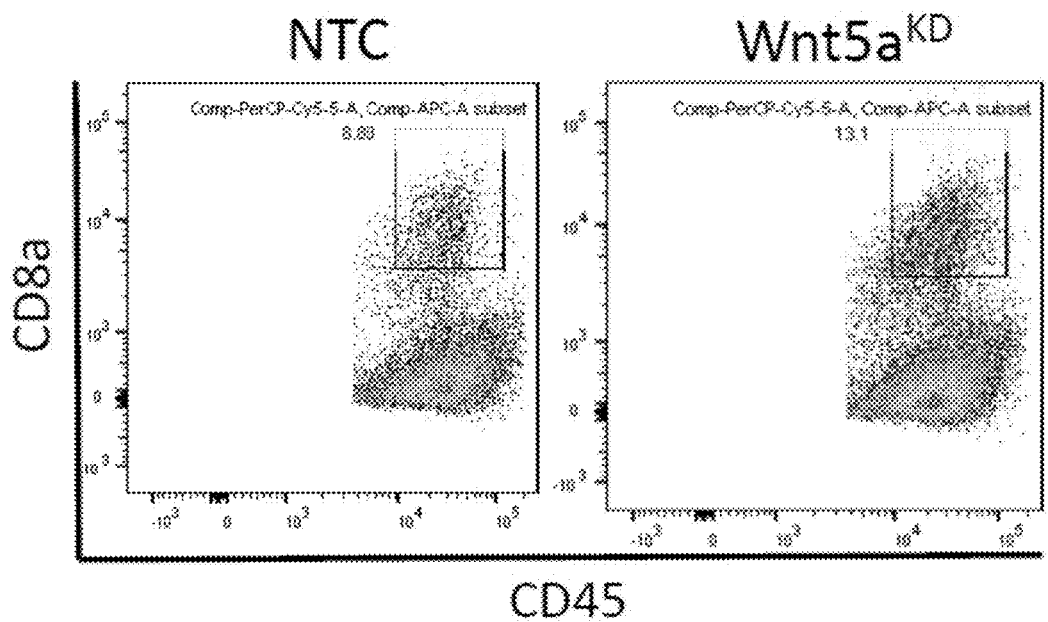
Figure 10C:
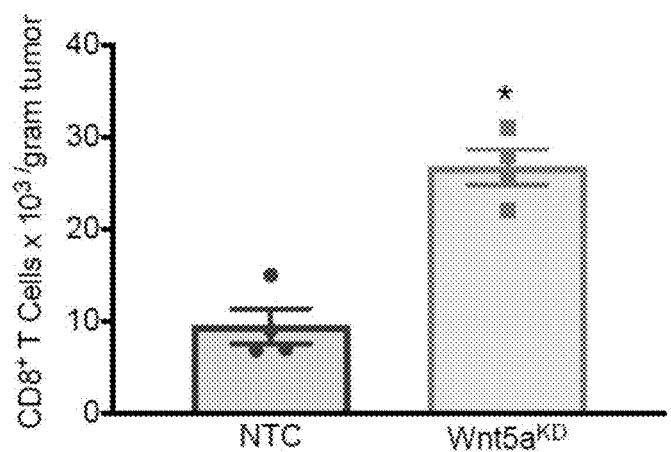

FIG. 10A-C. Escape from Anti-PD-1 Ab Therapy is Accompanied by Enhanced Wnt Signaling. (A) RNAseq differential gene expression analysis of resected autochthonous BRAFV600EPTEN−/−-melanoma tissues following treatment with either anti-PD-1 ab therapy (200 μg ip every 3 days) versus IgG isotype control (n=3/group). Yellow, upregulation. Blue, downregulation. (B) Genetic silencing of Wnt5a in the BRAFV600EPTEN−/−-melanoma cell line. Top left, Wnt5a Western blot analysis of NTC vs KD cell lines. Top right, CXCL5 Western blot analysis of NTC vs KD cell lines. Bottom, Wnt5a qrt-PCR analysis of NTC vs KD cell lines. (C) CD8+ T cell flow cytometry analysis (CD45+CD3+CD8+) of BRAFV600E-PTEN$^{-/-}$-NTC and BRAFV600EPTEN$^{-/-}$-Wnt5aKD melanoma tissues (n=4). Left, representative flow dot plots. NTC, non-targeted control. KD, knockdown. All data is mean±SEM. Significance assessed using Student's t test in panels A,C. *$P<0.05$. ***$P<0.0005$. Related to FIG. 2.

FIG. 11A-F. HSP70 Induces TLR4-dependent Wnt5a Upregulation in Melanoma. (A) TCGA SKCM melanoma database gene expression association analysis of TLR2 and TLR4 with WNT5A. (B) Wnt5a Western blot analysis of recombinant HSP70-treated BRAFV600EPTEN−/− melanoma cell line in the presence of increasing concentrations of TLR2 and TLR4 inhibitors. MPL4, TLR4 agonist. Representative of 2 independent experiments. (C) Left, TLR4 and Wnt5a Western blot analysis of NTC and TLR4KD BRAFV600EPTEN−/− melanoma cell lines. Right, TLR4 immunofluorescence (red) analysis of NTC and TLR4KD BRAFV600EPTEN−/− melanoma cell lines. Representative of 2 independent experiments. (D) TLR4 and Wnt5a qrt-PCR analysis of BRAFV600EPTEN−/− melanoma cells following TLR4-targeted siRNA transfection (n=3). (E) CD8+ T cell flow cytometry analysis of TLR4 siRNA-treated and Ctrl siRNA-treated BRAFV600EPTEN−/−-melanoma draining lymph node tissues (n=4). (F) Left, Wnt5a Western blot analysis of supernatant (SNT) and collected lysates from LPS and HSP70-treated MLE12 lung epithelial cells. Right, CXCL5 Western blot analysis of Wnt5a-treated MLE12 lung epithelial cell line. NTC, non-targeted control. KD, knockdown. Representative of 2 independent experiments. All data is mean±SEM. *P<0.05. Related to FIG. 3.

FIG. 12A-D. (A) Ovalbumin (OVA) Western blot of BRAFV600EPTEN−/− melanoma cell line (BP) and stable BRAFV600EPTEN−/−-OVA melanoma cell line (BP-OVA). Representative of 2 independent experiments. (B) Cleaved caspase-3 Western blot of BRAFV600EPTEN−/−-melanoma cell line following treatment with increasing concentrations of dacarbazine. Representative of 2 independent experiments. (C) Flow cytometry analysis of splenic CD45+CD3+CD8+ T cells following antibody-mediated CD8+ T cell ablation. Ctrl, IgG isotype control. Representative of 2 independent experiments. (D) Qrt-PCR analysis of inflammasome and TLR4 expression by the BRAFV600EPTEN−/−melanoma cell line (n=3). Data normalized to TLR9 expression. All data is mean±SEM. Related to FIG. 4.

FIG. 13A-F. (A) Supernatant (SNT) Caspase-1 p20 and total cell lysate pro-caspase-1 Western blot analysis following treatment of the Lewis lung carcinoma cell line with IFNγ (100 ng/mL) +/− increasing concentrations of anti-PD-L1 ab (0.5 μg/mL-2.0 μg/mL). Representative of 3 independent experiments. (B) ATP stimulation of non-targeted control and HSP70−/−BRAFV600EPTEN−/− melanoma cells. Left, pro-caspase-1 and caspase-1 p20 Western blots. Right, Wnt5a Western blot analysis of BRAFV600EPTEN−/− HSP70−/− cells (autocrine stimulation) and SNT-treated BRAFV600EPTEN−/−-NTC cells (paracrine stimulation). Representative of 2 independent experiments. (C) Caspase-1 p20 and pro-caspase-1 Western blot analysis following co-culture of either OT-1 CD8+ T cells or negative control (ctrl) MUT-specific CD8+ T cells with RAFV600EPTEN$^{-/-}$-OVA melanoma cells in the presence of increasing concentrations of anti-PD-1 ab or IFNγ receptor blocking ab. Representative of 2 independent experiments. (D) Caspase-1 p20 and SP70 Western blot analysis following OT-1 CD8+ T cell: BRAFV600EPTEN$^{-/-}$-OVA melanoma cell trans-well assay. Representative of 2 independent experiments (E) PD-L1 Western blot analysis of NTC and PD-LKD BRAFV600EPTEN$^{-/-}$ melanoma cells. (F) Caspase-1 p20 and pro-caspase-1 Western blot analysis following co-culture of OT-1 CD8+ T cells with BRAFV600EPTEN$^{-/-}$-OVA melanoma cells with IFNγ and anti-PD-L1 ab stimulation +/− PKR inhibitor (PKRi). Representative of 2 independent experiments. NTC, non-targeted control. KD, knockdown. Related to FIG. 5.

FIG. 14A-H. (A) NLRP3 Western blot analysis of NTC and NLRP3KD BRAFV600EPTEN−/− melanoma cells. (B) Representative dot plots of PMN-MDSC and CD8+ T cell flow cytometry analysis of resected BRAFV600EPTEN$^{-/-}$-NTC and BRAFV600EPTEN$^{-/-}$-NLRP3KD stable cell lines. Representative of 2 independent experiments. (C) Top, MTT cell proliferation assay of BRAFV600EPTEN$^{-/-}$-NTC, BRAFV600EPTEN−/−-NLRP3KD, BRAFV600EPTEN$^{-/-}$-PDL1KD stable cell lines in culture. ns, non-significant. Bottom, MTT cell proliferation assay of BRAFV600EPTEN−/−melanoma cells following treatment with NLRP3 inhibitor (MCC950) in culture. Each performed in triplicate. (D) Tumor growth curve of BRAFV600EPTEN$^{-/-}$-NLRP3KDmelanomas with CD8+ T cell ablation. Mice treated with anti-CD8 ab ip daily×3 days followed by anti-CD8 ab one week later (gray boxes). BRAFV600EPTEN$^{-/-}$-NTC control tumors also included (n=5). (E) Plasma HSP70 ELISA of BRAFV600EPTEN$^{-/-}$ melanoma-bearing mice following treatment with IgG isotype control ab, anti-PD-1 ab, or anti-PD-1 ab+MCC950 NLRP3 inhibitor (NLRP3i) (n=4/group). NTC, non-targeted control. KD, knockdown. (F) IL-1β qrt-PCR analysis of BRAFV600EPTEN−/− melanoma cells (n=3). Data normalized to TLR9 expression. (G) Above, IL-1β ELISA of BRAFV600EPTEN−/−-melanoma cell line supernatant after IFNγ/anti-PD-L1 ab treatment in vitro (n=3). Below, IL-1β ELISA of autochthonous BRAFV600EPTEN$^{-/-}$ tumor lysate and host plasma following treatment of mice with IgG isotype control ab and anti-PD-1 ab (200 μg ip q 3 days) in vivo (n=3/group). (H) Wnt5a Western blot analysis of BRAFV600EPTEN$^{-/-}$ melanoma cells after treatment with titrated concentrations of recombinant IL-1β and HSP70. Representative of 2 independent experiments. All data is mean±SEM. *P<0.05. Related to FIG. 6.

FIG. 15A-B. (A). Western blot analysis of Caspase-1 p20 (Caspase-1 cleavage product and indicator of NLRP3 inflammasome activation), HSP70, and Wnt5a in the supernatant. TLR4i, TLR4 inhibitor. MPLA, TLR4 agonist. (B) KRas mutant CRC Exhibits Elevated Levels of NLRP3 Inflammasome Activation based on HSP70 Release. Surface PD-L1 flow cytometry analysis of AP, ABP, and AKP organoid cell lines. HSP70 and PD-L1 Western blot analysis of the same lines. A, APC$^{-/-}$. P, p53$^{-/-}$. B, BRAF$^{V600E}$, K, KRas$^{G12D}$.

DETAILED DESCRIPTION OF THE INVENTION

The present invention has been described in terms of one or more preferred embodiments, and it should be appreciated that many equivalents, alternatives, variations, and modifications, aside from those expressly stated, are possible and within the scope of the invention.

The present invention is based on the surprising and unexpected findings of the inventors that treatment with a programmed cell death 1 (PD-1) blockade induced a programmed death ligand 1/NOD-, LRR-, and pyrin domain-containing protein 3 (PD-L1/NLRP3) inflammasome signaling cascade that ultimately led to the recruitment of granulocytic myeloid-derived suppressor cells (PMN-MDSCs) into tumor tissues, thereby dampening and reducing the resulting antitumor immune response, as seen by a reduction in the CD8+ T cell response to the tumor antigens. The inventors demonstrated that genetic and pharmacologic inhibition of NLRP3 suppressed PMN-MDSC tumor infiltration and significantly augmented the efficacy of anti-PD-1 antibody immunotherapy. This pathway represents a tumor-intrinsic mechanism of adaptive resistance to anti-PD-1 checkpoint inhibitor immunotherapy, and provides compositions and methods of treating cancers that may be refractory or resistant initially to checkpoint inhibitor therapy.

A. Methods

In one embodiment, the disclosure provides a method of treating a cancer in a subject in need there of the method comprising, consisting of, or consisting essentially of administering to the subject a therapeutically effective amount of an NLRP3 inhibitor and at least one checkpoint inhibitor such that the cancer is treated in the subject. The combination of NLRP3 inhibitor and at least one checkpoint inhibitor, preferably a PD-1 inhibitor, provides an increased CD8+ T cell response to the tumor increasing the anti-tumor immune response, and resulting in a reduction in tumor cell volume. As described in the examples, the administration of the NLRP3 inhibitor reduces or inhibits the recruitment of granulocytic myeloid-derived suppressor cells (PMN-MDSCs) from the tumor microenvironment, which in turn allows for an increase in the CD8+ T cell response to the tumor.

As used herein, the term "NLRP3 inhibitor" refers to any compound/molecule that is capable of inhibiting and/or reducing the expression and/or function of the NLRP3 inflammasome. NLRP3 inhibitors may include, but are not limited to, antibodies, small molecules, peptides, miRNAs, siRNAs, oligonucleotides, agonists, cytokines and the like. Suitable examples include, but are not limited to, carbobenzoxy-valyl-alanyl-aspartyl-[O-methyl]-fluoromethylketone (Z-VAD-FMK), N-[[(1,2,3,5,6,7-hexahydro-s-indacen-4-yl)amino]carbonyl]-4-(1-hydroxy-1-methylethyl)-2-furansulfonamide (MCC950), Beta-hydroxybutyrate (BHB), 3,5,4'-trihydroxy-trans-stilbene (Resveratrol), (3aR,4aS,6aS,9aS,9bR)-1,4a-Dimethyl-7-methylene-5,6,6a,7,9a,9b-hexahydro-3H-oxireno[8,8a]azuleno[4,5-b]furan-8(4aH)-one (Arglabin), cannabinoid receptor 2 (CB2R) agonist, miRNA-223, Type I interferons (IFN) such as IFN-beta, 5-chloro-2-methoxy-N-(4-(N-methylsulfamoyl)phenethyl) benzamide (JC124), 4-[[4-Oxo-2-thioxo-3-[[3-(trifluoromethyl)phenyl]methyl]-5-thiazolidinylidene]methyl]benzoic acid (CY09), 3-methylsulfonylpropanenitrile (dapansutrile; OLT1177), and the like.

As used herein, "treatment," "therapy" and/or "therapy regimen" refer to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition. As used herein, the terms "treat," "treatment," and "treating" refer to reducing the amount or severity of a particular condition, disease state (e.g., cancers), or symptoms thereof, in a subject presently experiencing or afflicted with the condition or disease state. The terms do not necessarily indicate complete treatment (e.g., total elimination of the condition, disease, or symptoms thereof). "Treatment," encompasses any administration or application of a therapeutic or technique for a disease (e.g., in a mammal, including a human), and includes inhibiting the disease, arresting its development, relieving the disease, causing regression, or restoring or repairing a lost, missing, or defective function; or stimulating an inefficient process. Specifically, treatment results in the reduction in tumor load or volume in the patient, and in some instances, leads to regression and elimination of the tumor or tumor cells. As used herein, the term "treatment" is not necessarily meant to imply cure or complete abolition of the tumor. Treatment may refer to the inhibiting or slowing of the progression of the tumor, reducing the incidence of tumor, reducing metastasis of the tumor, or preventing additional tumor growth. In some embodiments, treatment results in complete regression of the tumor.

The term "disease" or "disorder" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like. Preferably, the disease being treated by the methods described herein are cancers or any disease or cancer that can be treated by activating a CD8+ T cell response against an associated antigen, for example, an associated tumor antigen.

As is known in the art, a cancer is generally considered as uncontrolled cell growth. The methods of the present invention can be used to treat any cancer, and any metastases thereof, including, but not limited to, carcinoma, lymphoma, blastoma, sarcoma, and leukemia. More particular examples of such cancers include breast cancer, prostate cancer, colon cancer, squamous cell cancer, basal cell carcinoma, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, mesothelioma, kidney cancer, vulval cancer, pancreatic cancer, thyroid cancer, hepatic carcinoma, skin cancer, melanoma, brain cancer, neuroblastoma, myeloma, various types of head and neck cancer, acute lymphoblastic leukemia, acute myeloid leukemia, Ewing sarcoma and peripheral neuroepithelioma. In some embodiments, the cancer comprises a cancer resistant to checkpoint inhibitor therapies.

In other embodiments, the cancer comprises a cancer resistant or refractory to anti-PD-1 immunotherapy. In other embodiments, the cancer is melanoma, lung cancer, pancreatic cancer, renal cancer. In other embodiments, the cancer is a PD-1 resistant cancer such as PD-1 therapy resistant melanoma.

The term "refractory" or "resistant" to checkpoint inhibitors or PD-1/PD-L1 inhibitors refers to subjects that have been treated with the checkpoint inhibitors and/or PD-1/PD-L1 inhibitors and the cancer has either developed resistance to the therapy or has responded poorly or not responded to the treatment with the inhibitors even at the beginning of treatment.

As used herein, the term "Checkpoint inhibitor(s)" refers to any compound capable of inhibiting and/or disrupting the function and/or expression of checkpoint molecules (e.g., CTLA-4, PD-1, PD-L1, etc.) involved in cell division. For the present invention, the preferred checkpoint inhibitors contemplated for use in the present invention are inhibitors of PD-1 or PD-L1, which act through the pathway described herein. Inhibitors may include, but are not limited to, antibodies, peptides, small molecules, antisense RNAs, cDNAs, miRNAs, siRNAs, aptamers, oligonucleotides, and the like. Preferably, the checkpoint inhibitors include PD-1 or PD-L1 inhibitors. Examples include, but are not limited to, nivolumab, an anti-PD-1 antibody, available from Bristol-Myers Squibb Co and described in U.S. Pat. Nos. 7,595,048, 8,728,474, 9,073,994, 9,067,999, 8,008,449 and 8,779,105; pembrolizumab, and anti-PD-1 antibody, available from Merck and Co and described in U.S. Pat. Nos. 8,952,136, 83,545,509, 8,900,587 and EP2170959; atezolizumab is an anti-PD-L1 available from Genentech, Inc. (Roche) and described in U.S. Pat. No. 8,217,149; avelumab (Bavencio, Pfizer, formulation described in PCT Publ. WO2017097407), durvalumab (Imfinzi, Medimmune/Astra- Zeneca, WO2011066389), cemiplimab (Libtayo, Regeneron Pharmaceuticals Inc., Sanofi), spartalizumab (PDR001, Novartis), camrelizumav (AiRuiKa, Hengrui Medicine Co.), sintillimab (Tyvyt, Innovent Biologics/Eli Lilly), KN035 (Envafolimab, Tracon Pharmaceuticals); tislelizumab available from BeiGene and described in U.S. Pat. No. 8,735,553; among others and the like. Other PD-1 and PD-L1 that are in development may also be used in the practice of the present invention, including, for example, PD-1 inhibitors including toripalimab (JS-001, Shanghai Junshi Biosciences), dostarlimab (GlaxoSmithKline), INCMGA00012 (Incyte, MarcoGenics), AMP-224 (AstraZeneca/MedImmune and GlaxoSmithKline), AMP-514 (AstraZeneca), and PD-L1 inhibitors including AUNP12 (Aurigene and Laboratoires), CA-170 (Aurigen/Curis), and BMS-986189 (Bristol-Myers Squibb), among others. The term "checkpoint inhibitor therapy" refers to the form of cancer immunotherapy that block inhibitory checkpoints and thereby restore immune system function. Such therapies are known by those skilled in the art. In some embodiments, the PD-1 inhibitor is selected from the group consisting of Nivolumab (anti-PD-1), Pembrolizumab (anti-PD-1), and combinations thereof. In some embodiments, the PD-L1 inhibitor is selected from atezolizumab, avelumab, and durvalumab, among others. CTLA-4 inhibitors are not contemplated for use in the present invention, as described in the examples, CTLA-4 inhibitors do not act through the same pathway as the PD-1/PD-L1 inhibitors with respect to NLRP3 inhibitors, and as such, the combination of such does not produce the desired outcome as described herein, demonstrating the combination is unpredictable without knowledge of the underlying signaling mechanism, as described herein.

The term "effective amount" or "therapeutically effective amount" refers to an amount sufficient to effect beneficial or desirable biological and/or clinical results.

As used herein, the term "subject" and "patient" are used interchangeably herein and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. In some embodiments, the subject comprises a human. In other embodiments, the subject comprises a human suffering from a cancer. Preferably the human has cancer that is refractory or resistant to checkpoint inhibitor therapy, for example, anti-PD-1 therapy. For example, the human may have refractory melanoma.

Unless otherwise defined, all technical terms used herein have the same meaning as commonly understood by one of ordinary skill in the art to which this disclosure belongs.

In some embodiments, the checkpoint inhibitors are administered prior to the NLRP3 inhibitor. In other embodiments, the checkpoint inhibitors are administered concurrently with the NLRP3 inhibitor. In yet other embodiments, the checkpoint inhibitors are administered after the NLRP3 inhibitor.

Another embodiment of the present disclosure provides a method of increasing the efficacy of anti-PD-1 antibody immunotherapy comprising, consisting of, or consisting essentially of administering to the subject a therapeutically effective amount of an NLRP3 inhibitor together with an anti-PD-1 therapy, e.g., an anti-PD-1 antibody, such that the cancer is treated in the subject. In some examples, the subject is refractory or resistant to treatment with the anti-PD-1/PD-L1 therapy, and the treatment with the NLRP3 inhibitor restores the efficacy and effectiveness of the anti-PD-1/PD-L1 therapy, leading to a reduction in tumor growth and increased reduction in tumor cells within the patient. Suitable NLRP3 inhibitors are described herein, and can be used in combination with the anti-PD-1/PD-L1 therapies described herein and demonstrated in the examples. Surprisingly, it was found that anti-CTL-4 therapies did not work by the same mechanism of action as the anti-PD-1/PD-L1, and as such, the unexpected results described herein related to the combination of NLRP3 and an anti-PD-1/PD-L1 therapies specifically not other checkpoint inhibitors.

In another embodiment, the method further comprises administering another anti-cancer therapy. Suitable anti-cancer therapies may include, but are not limited to, surgery, chemotherapy, radiation, immunotherapy, targeted drug therapy, cryoablation, hormone therapy, bone marrow transplants, and the like.

In another embodiment, the disclosure provides a method of treating a subject who is refractory or not responding to anti-PD-1/PD-L1 treatment, the method comprising administering to the subject a therapeutically effective amount of an NLRP3 inhibitor and an anti-PD-1/PD-L1 antibody such that the cancer is treated in the subject. In some embodiment, the method further comprises selecting a subject that was previously been treated with anti-PD-1/PD-L1 inhibitor and was resistant to treatment. In some embodiments, the refractory subject is administered the NLRP3 inhibitor prior to administering the PD-1/PD-L1 inhibitor.

In some embodiments, the present disclosure provides methods of reducing the recruitment of myeloid-derived suppressor cells (MDSCs) to tumor microenvironment, in turn allowing for the effective treatment of a tumor with a checkpoint inhibitor therapy, for example, an anti-PD-1 therapy, specifically an anti-PD1 or an anti-PD-L1 antibody. Administration of at least one NLRP3 inhibitor leads to the inhibition of the signaling pathway which in turn reduces the signaling cascade that results in MDSCs recruitment to the microenvironment. This reduction in MDSCs recruitment in turn results in an increase in the ability to mount a CD8+ T cell response to the tumor, especially when a subject is treated with a checkpoint inhibitor such as a PD-1/PD-L1 inhibitor. As such, the methods described herein are able to treat cancers that may have been resistant or refractory to PD-1/PD-L1 inhibitory therapy as it alters the adaptive immune response within the subject.

B. Pharmaceutical Compositions

In another aspect, the present disclosure provides pharmaceutical compositions comprising one or more of compounds as described herein and an appropriate carrier, excipient or diluent. As used herein, the term "compounds" include those checkpoint inhibitors and/or NLRP3 inhibitors as provided herein. The compounds may be either alone (e.g., formulated individually) or in combination (e.g., formulated as a cocktail). The exact nature of the carrier, excipient or diluent will depend upon the desired use for the composition, and may range from being suitable or acceptable for veterinary uses to being suitable or acceptable for human use. The composition may optionally include one or more additional compounds.

When used to treat or prevent diseases/disorder as provided herein (e.g., cancer), the compounds described herein may be administered singly, as mixtures of one or more compounds or in mixture or combination with other agents useful for treating such diseases and/or the symptoms associated with such diseases. The compounds may also be administered in mixture or in combination with one or more additional agents useful to treat the disorder/disease, such as chemotherapeutic agents (e.g., alkylating agents, topoisomerase inhibitors, mitotic inhibitors, antimetabolites, and the like), radiation, other checkpoint inhibitors (e.g., PD-L1, CTLA-4, PD-1, etc.), to name a few. The compounds may be administered in the form of compounds per se, or as pharmaceutical compositions comprising a compound.

Pharmaceutical compositions comprising the compound(s) may be manufactured by means of conventional mixing, dissolving, granulating, dragee-making levigating, emulsifying, encapsulating, entrapping or lyophilization processes. The compositions may be formulated in conventional manner using one or more physiologically acceptable carriers, diluents, excipients or auxiliaries which facilitate processing of the compounds into preparations which can be used pharmaceutically.

The compounds may be formulated in the pharmaceutical composition per se, or in the form of a hydrate, solvate, N-oxide or pharmaceutically acceptable salt, as previously described. Typically, such salts are more soluble in aqueous solutions than the corresponding free acids and bases, but salts having lower solubility than the corresponding free acids and bases may also be formed.

Pharmaceutical compositions may take a form suitable for virtually any mode of administration, including, for example, topical, ocular, oral, buccal, systemic, nasal, injection, transdermal, rectal, vaginal, etc., or a form suitable for administration by inhalation or insufflation.

For topical administration, the compound(s) may be formulated as solutions, gels, ointments, creams, suspensions, etc. as are well-known in the art. Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives. Alternatively, the injectable formulation may be provided in powder form for reconstitution with a suitable vehicle, including but not limited to sterile pyrogen free water, buffer, dextrose solution, etc., before use. To this end, the active compound(s) may be dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the compound, as is well known. For buccal administration, the compositions may take the form of tablets or lozenges formulated in conventional manner. For rectal and vaginal routes of administration, the compound(s) may be formulated as solutions (for retention enemas) suppositories or ointments containing conventional suppository bases such as cocoa butter or other glycerides.

For nasal administration or administration by inhalation or insufflation, the compound(s) can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

For ocular administration, the compound(s) may be formulated as a solution, emulsion, suspension, etc. suitable for administration to the eye. A variety of vehicles suitable for administering compounds to the eye are known in the art.

For prolonged delivery, the compound(s) can be formulated as a depot preparation for administration by implantation or intramuscular injection. The compound(s) may be formulated with suitable polymeric or hydrophobic materials (e.g., as an emulsion in an acceptable oil) or ion exchange resins, or as sparingly soluble derivatives, e.g., as a sparingly soluble salt.

Alternatively, transdermal delivery systems manufactured as an adhesive disc or patch which slowly releases the compound(s) for percutaneous absorption may be used. To this end, permeation enhancers may be used to facilitate transdermal penetration of the compound(s).

Alternatively, other pharmaceutical delivery systems may be employed. Liposomes and emulsions are well-known examples of delivery vehicles that may be used to deliver compound(s). Certain organic solvents such as dimethyl sulfoxide (DMSO) may also be employed, although usually at the cost of greater toxicity.

The pharmaceutical compositions may, if desired, be presented in a pack or dispenser device which may contain one or more unit dosage forms containing the compound(s). The pack may, for example, comprise metal or plastic foil, such as a blister pack. The pack or dispenser device may be accompanied by instructions for administration.

The compound(s) described herein, or compositions thereof, will generally be used in an amount effective to achieve the intended result, for example in an amount effective to treat or prevent the particular disease being treated. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. Therapeutic benefit also generally includes halting or slowing the progression of the disease, regardless of whether improvement is realized.

The amount of compound(s) administered will depend upon a variety of factors, including, for example, the particular indication being treated, the mode of administration, whether the desired benefit is prophylactic or therapeutic, the severity of the indication being treated and the age and weight of the patient, the bioavailability of the particular compound(s) the conversation rate and efficiency into active drug compound under the selected route of administration, etc.

Determination of an effective dosage of compound(s) for a particular use and mode of administration is well within the capabilities of those skilled in the art. Effective dosages may be estimated initially from in vitro activity and metabolism assays. For example, an initial dosage of compound for use in animals may be formulated to achieve a circulating blood or serum concentration of the metabolite active compound that is at or above an IC50 of the particular compound as measured in as in vitro assay. Calculating dosages to achieve such circulating blood or serum concentrations taking into account the bioavailability of the particular compound via the desired route of administration is well within the capabilities of skilled artisans. Initial dosages of compound can also be estimated from in vivo data, such as animal models. Animal models useful for testing the efficacy of the active metabolites to treat or prevent the various diseases described above are well-known in the art. Animal models suitable for testing the bioavailability and/or metabolism of compounds into active metabolites are also well-known. Ordinarily skilled artisans can routinely adapt such information to determine dosages of particular compounds suitable for human administration.

Dosage amounts will typically be in the range of from about 0.0001 mg/kg/day, 0.001 mg/kg/day or 0.01 mg/kg/day to about 100 mg/kg/day, but may be higher or lower, depending upon, among other factors, the activity of the active compound, the bioavailability of the compound, its metabolism kinetics and other pharmacokinetic properties, the mode of administration and various other factors, discussed above. Dosage amount and interval may be adjusted individually to provide plasma levels of the compound(s) and/or active metabolite compound(s) which are sufficient to maintain therapeutic or prophylactic effect. For example, the compounds may be administered once per week, several times per week (e.g., every other day), once per day or multiple times per day, depending upon, among other things, the mode of administration, the specific indication being treated and the judgment of the prescribing physician. In cases of local administration or selective uptake, such as local topical administration, the effective local concentration of compound(s) and/or active metabolite compound(s) may not be related to plasma concentration. Skilled artisans will be able to optimize effective dosages without undue experimentation.

Yet another aspect of the present disclosure provides all that is disclosed and illustrated herein.

The use herein of the terms "including," "comprising," or "having," and variations thereof, is meant to encompass the elements listed thereafter and equivalents thereof as well as additional elements. Embodiments recited as "including," "comprising" or "having" certain elements are also contemplated as "consisting essentially of" and "consisting of" those certain elements.

As used herein, "about" means within 5-10% of a stated concentration range or within 5-10% of a stated number.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The present invention has been described in terms of one or more preferred embodiments, and it should be appreciated that many equivalents, alternatives, variations, and modifications, aside from those expressly stated, are possible and within the scope of the invention.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1

An Intrinsic Tumor PD-L1-NLRP3 Inflammasome Signaling Pathway Drives Adaptive Resistance to Anti-PD-1 Immunotherapy An in-depth understanding of immune escape mechanisms in cancer is likely to lead to innovative advances in immunotherapeutic strategies. However, much remains unknown regarding these mechanisms and how they impact immunotherapy resistance. Using several preclinical tumor models as well as clinical specimens, we identified a mechanism whereby CD8+ T cell activation in response to programmed cell death 1 (PD-1) blockade induced a programmed death ligand 1/NOD-, LRR-, and pyrin domain-containing protein 3 (PD-L1/NLRP3) inflammasome signaling cascade that ultimately led to the recruitment of granulocytic myeloid-derived suppressor cells (PMN-MDSCs) into tumor tissues, thereby dampening the resulting antitumor immune response. The genetic and pharmacologic inhibition of NLRP3 suppressed PMN-MDSC tumor infiltration and significantly augmented the efficacy of anti-PD-1 antibody immunotherapy. This pathway therefore represents a tumor-intrinsic mechanism of adaptive resistance to anti-PD-1 checkpoint inhibitor immunotherapy and is a promising target for future translational research.

Here, the inventors describe a pathway that mechanistically links the upregulation of PD-L1 with the promotion of PMN-MDSC recruitment to the tumor bed in response to anti-PD-1 blockade and demonstrate that the inhibition of this process substantially enhances responses to checkpoint inhibitor immunotherapy (FIG. 1A). The inventors provide further evidence to support the existence of this pathway in patients with cancer, and that the combination of an NLRP3 inhibitor with a checkpoint inhibitor, specifically anti-PD-1 therapies, results in increased efficacy of the PD-1 inhibitor and reduction in tumor load.

Results

Anti-PD-1 Antibody Immunotherapy Induces the Recruitment of PMN-MDSCs.

Figures 1F, 1G, 1H:
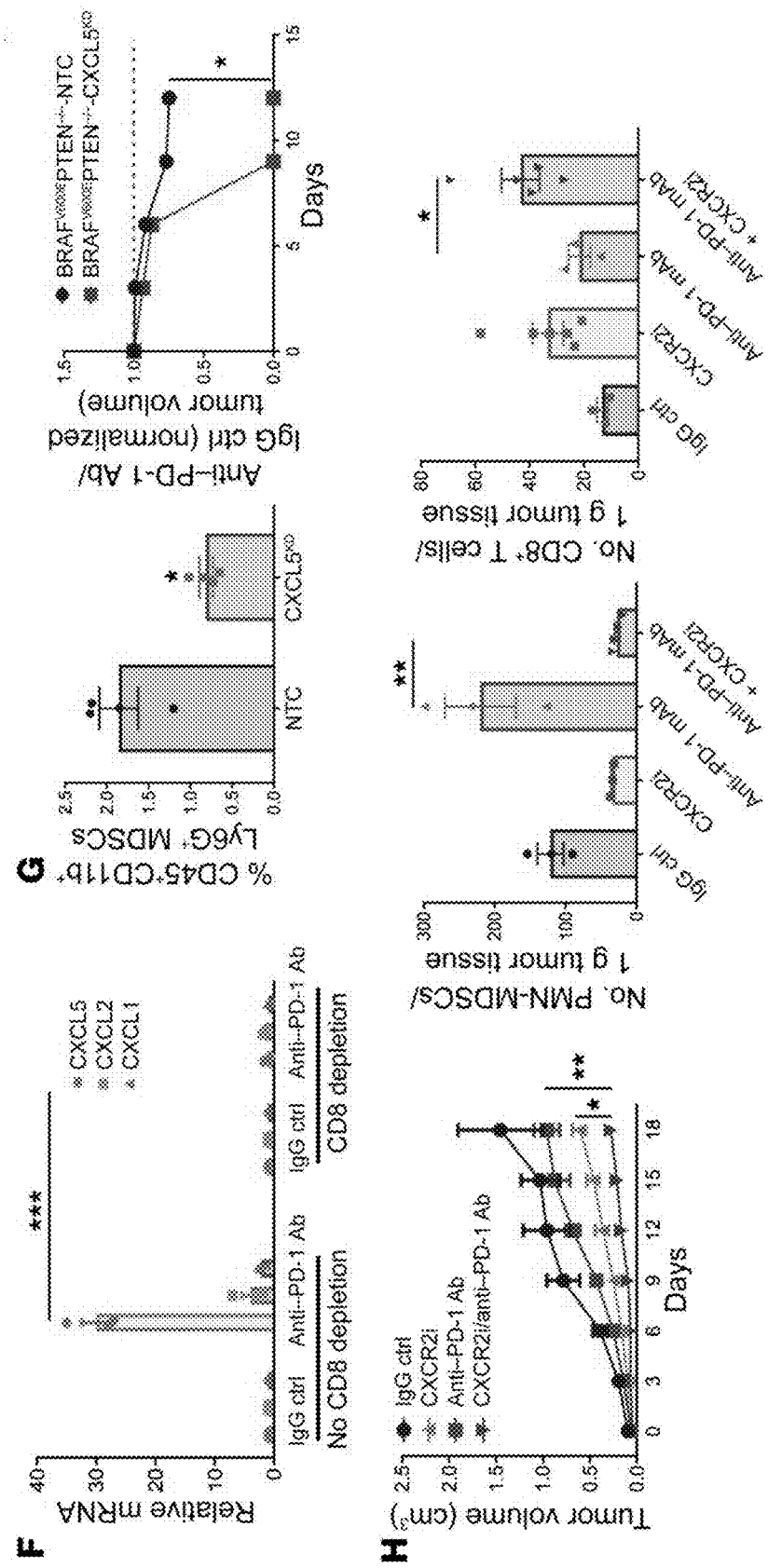
Figure 8A:
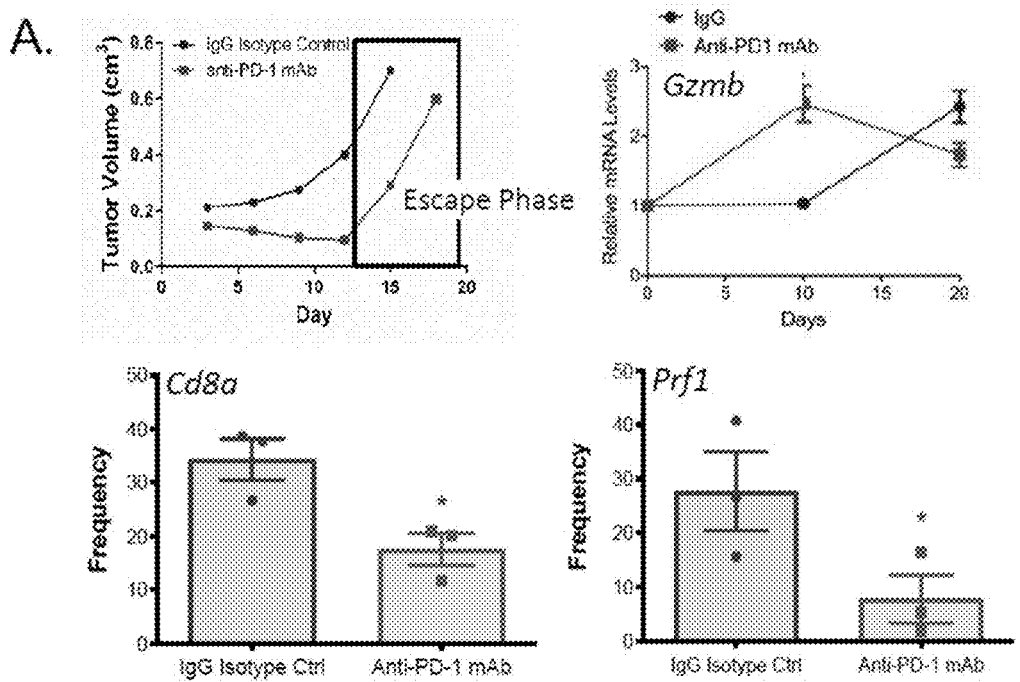
Figure 8B:
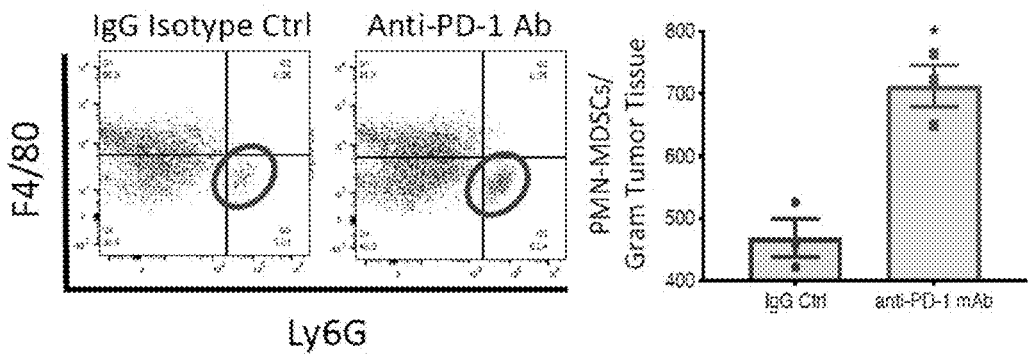
Figure 8B:
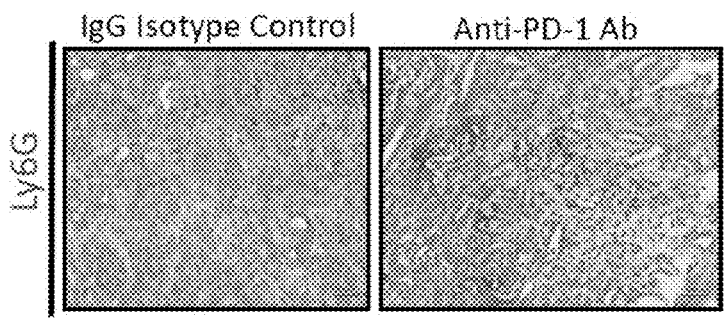
Figure 8B:
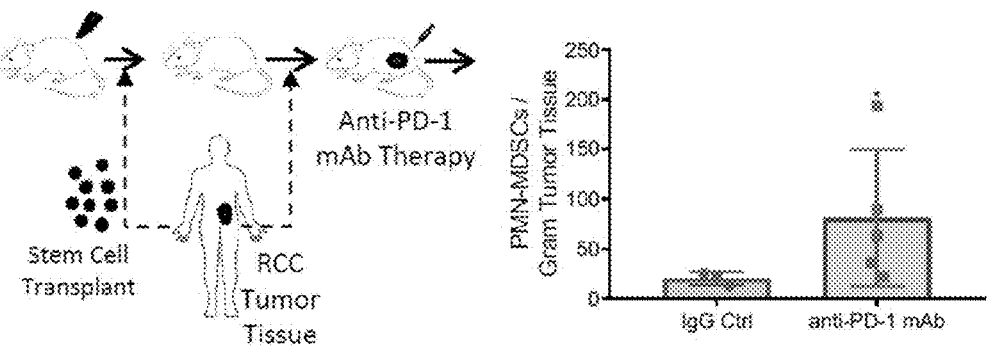
Figures 8C, 8D:
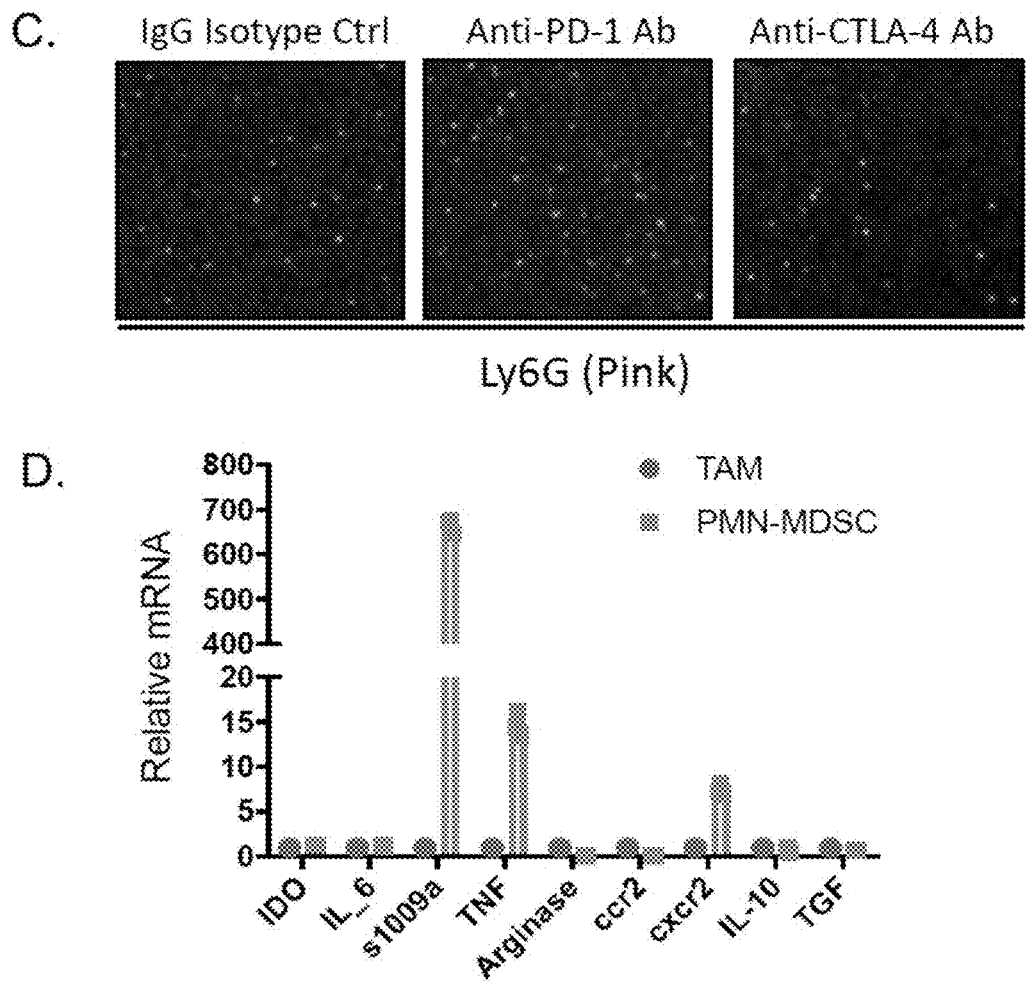
Figures 9A, 9B:
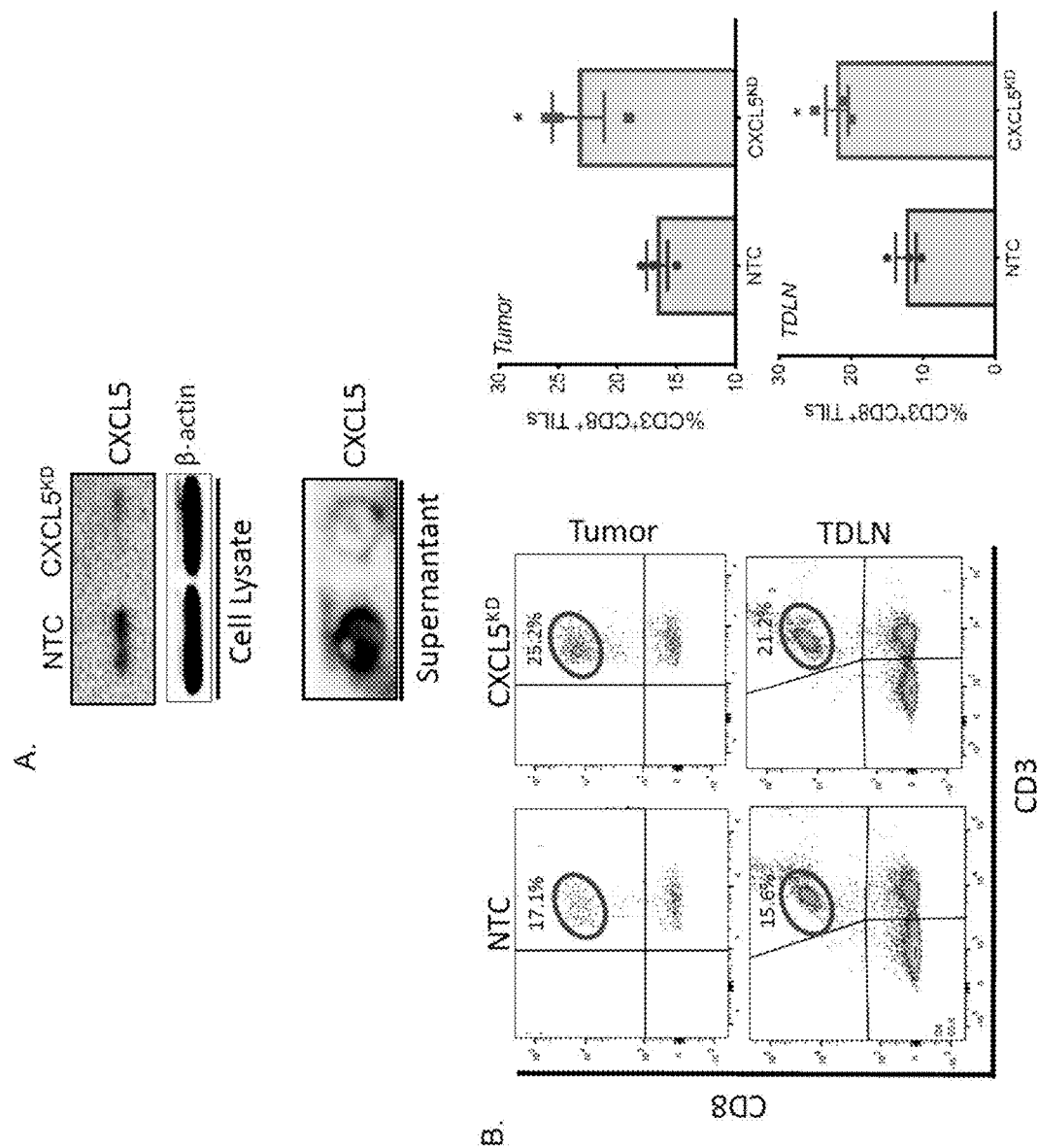
Figure 9C:
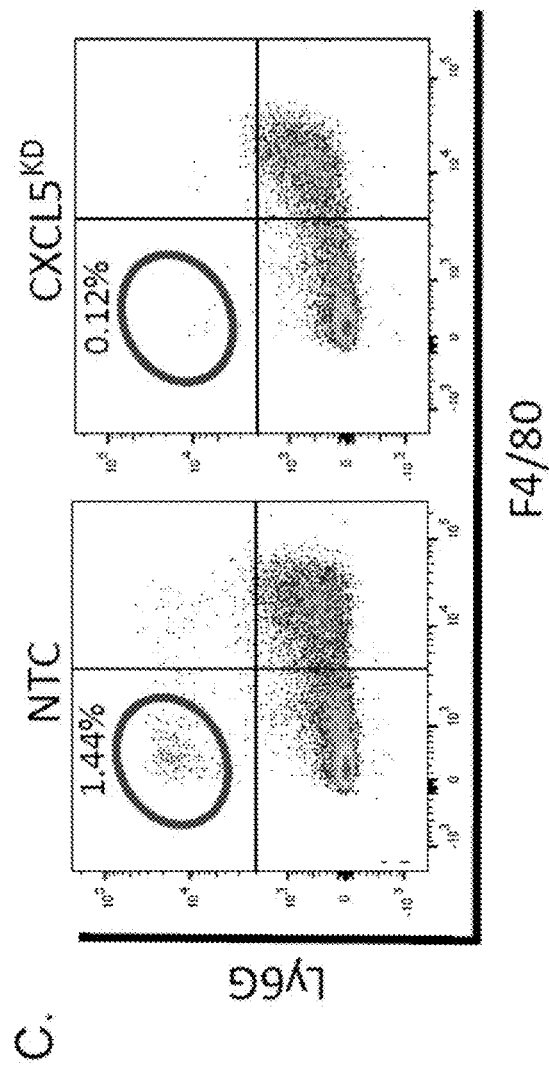
Figure 9D:
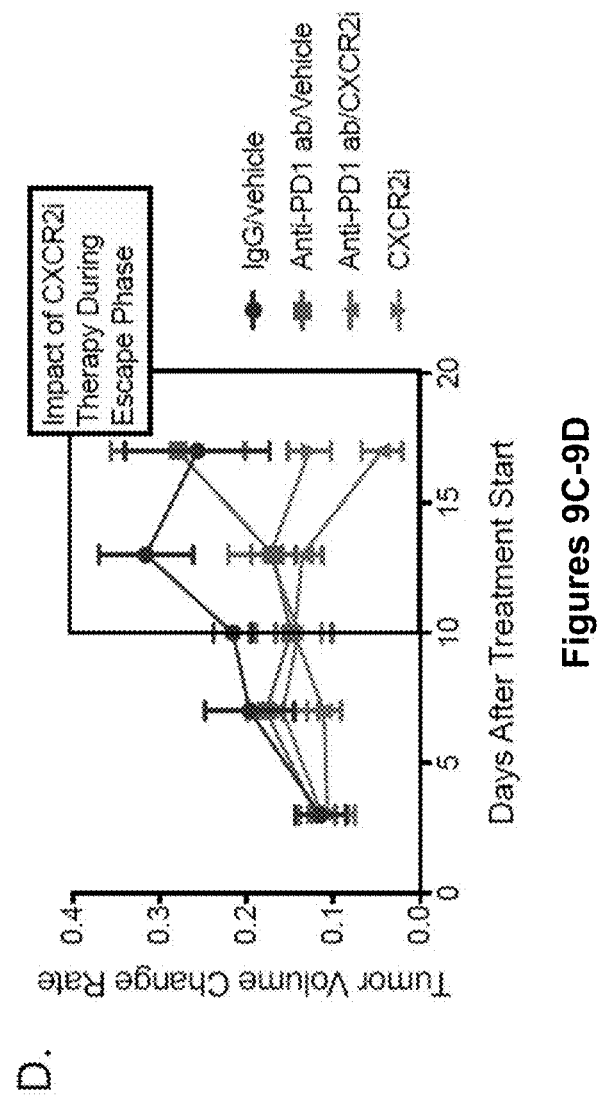

We have found that the autochthonous BRAFV600E PTEN-/-melanoma model exhibits a transient response to anti-PD-1 Ab immunotherapy followed by eventual escape and progression. We harvested these melanoma tissues following anti-PD-1 Ab escape as well as after IgG isotype control Ab therapy and performed differential whole transcriptomic sequencing analysis. This study revealed the upregulation of 51 genes in anti-PD-1 Ab-treated tumor tissues using a fold-change cutoff of 2.0 ($P<0.05$). Of these genes, two CXCR2 ligands, Cxcl5 (3.75-fold, $P=8.88\times10-6$) and Cxcl3 (3.49-fold, $P=0.002$), were found in the top 7 upregulated genes, whereas Cxcl2 was also noted to be upregulated by 3.63-fold ($P=0.146$). These gene expression changes occurred concurrently with enhanced expression of the proinflammatory proteins S100a8 (2.27-fold, $P=1.61\times10-10$) and S100a9 (2.27-fold, $P=3.37\times10-11$) as well as Arg (1.45-fold, $P=1.95\times10-6$) (FIG. 1B). We repeated the above experiment using a serial tissue biopsy approach coupled with quantitative real-time PCR (qRT-PCR) gene expression analysis, which confirmed a time-dependent increase in the expression of Cxcl2, Cxcl5, Cxcr2, Ly6g and the myeloid marker S100a9 during the course of anti-PD-1 Ab therapy relative to those tumors treated with an IgG isotype Ab (FIG. 1C and FIG. 8A). Together, these data suggest that immunosuppressive PMNMDSC recruitment may correlate with suppression of cytolytic T cell activity along with anti-PD-1 Ab escape (FIG. 8A). To investigate this hypothesis, we evaluated resected melanoma tissue based on Gr-1 IHC as well as multiparameter flow cytometry, both of which confirmed a significant increase in infiltrating Gr-1+ and CD45+ CDiib+Ly6G+Ly6CintF4/80- cell populations (PMN-MDSCs), respectively, with progression through anti-PD-1 Ab therapy (FIGS. 1, D and E). These findings were recapitulated in the Lewis lung carcinoma (LLC) lung cancer model, an orthotopic p53 Kras pancreatic cancer model, as well as in a humanized autologous patient-derived xenograft model of renal cell carcinoma (FIG. 8B). However, we did not observe any evidence of this effect following anti-CTLA-4 Ab therapy (FIG. 8C). qRT-PCR analysis of FACS-sorted PMNMDSCs from anti-PD-1 Ab-treated BRAFV600E PTEN-/- melanoma tissue confirmed that these cells expressed high levels of Cxcr2, Tnfa, S100a8, and S00a9 (FIG. 8D). Although we observed an increase in the expression of several CXCR2-dependent ligands following escape from anti-PD-1 Ab therapy, CD8+ T cell ablation studies demonstrated the CXCL5 chemokine to be particularly responsive to the induction of CD8+ T cell activation (FIG. 1F). In addition, CXCL5 has previously been implicated in melanoma pathogenesis (26). Thus, we genetically silenced CXCL5 expression in a BRAFV600E PTEN-/- melanoma cell line, which effectively eliminated PMN-MDSC recruitment, enhanced tumor CD8+ T cell infiltration, and significantly increased the sensitivity of BRAFV600E PTEN-/- melanomas to anti-PD-1 Ab immunotherapy (FIG. 1G and FIG. 9). Further in vivo tumor studies using a pharmacological CXCR2 inhibitor (AZD5069) also significantly suppressed PMN-MDSC recruitment in response to anti-PD-1 Ab therapy, enhanced CD8+ T cell tumor infiltration, and suppressed tumor progression in the autochthonous BRAFV600E PTEN-/- melanoma model (FIG. 1H). Notably, we found the impact of AZD5069 to be more significant at later time points correlating with the period of PMN-MDSC influx into the tumor (FIG. 9D). Together, these data indicate that tumors exhibit an increase in CXCR2 ligand-mediated PMN-MDSC recruitment to the tumor bed during their progression through anti-PD-1 Ab immunotherapy.

Wnt5a Promotes CXCR2 Ligand Expression in Response to Anti-PD-1 Immunotherapy.

Figures 2A, 2B, 2C, 2D, 2E, 2F, 2G:
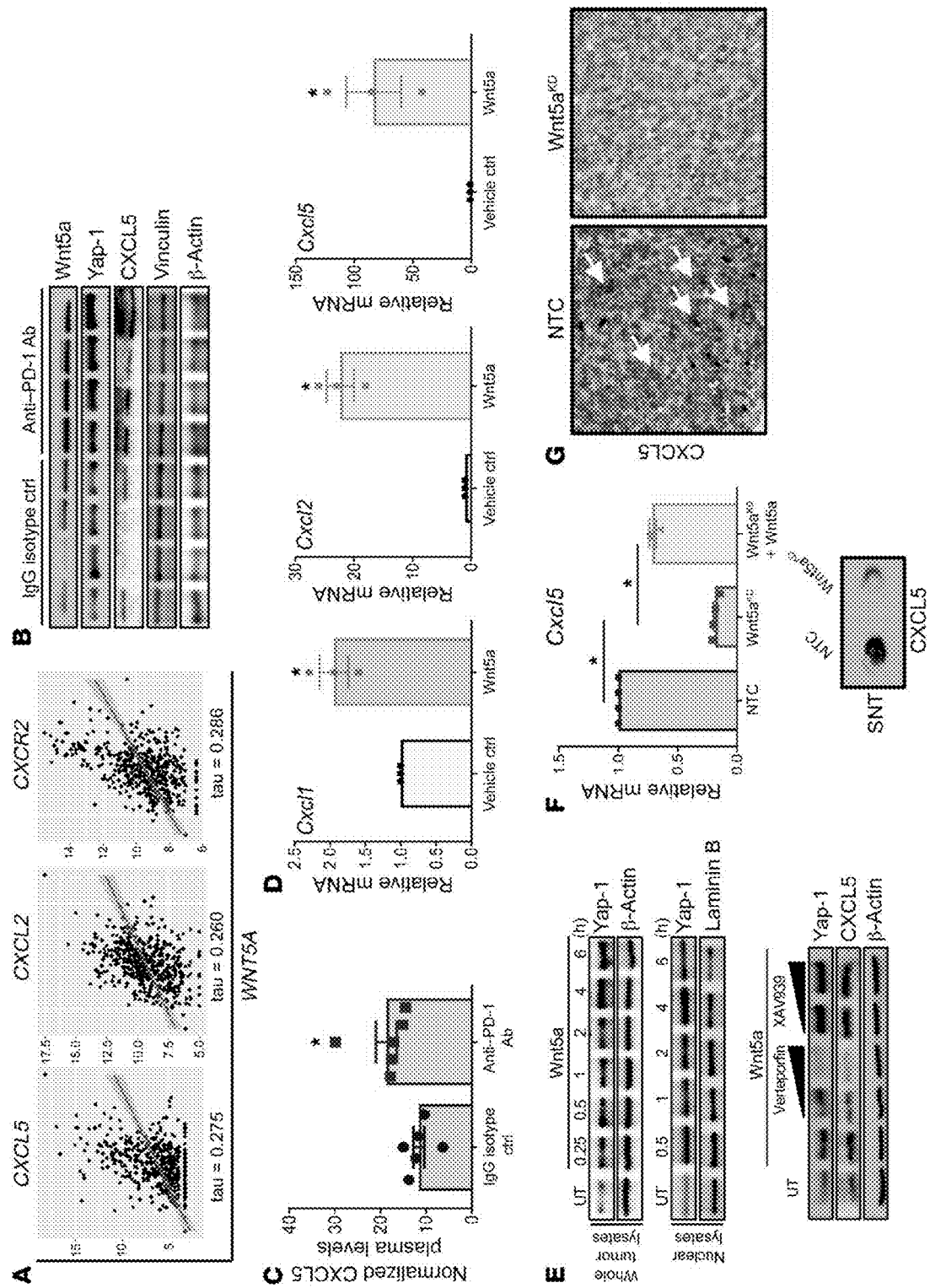
FIG. 2A-H. Wnt5a induces CXCR2-dependent chemokine expression in response to anti-PD-1 Ab immunotherapy. (A) TCGA human melanoma database gene expression analysis of CXCL5, CXCL2, and CXCR2 association with WNT5A. (B) Whole tumor tissue Western blot analysis of Wnt5a, YAP1, CXCL5, and vinculin and β-actin (used as loading controls). Blot is representative of 3 independent experiments. (C) Plasma CXCL5 ELISA following anti-PD-1 Ab therapy versus IgG isotype control therapy in the transgenic BRAFV600E PTEN−/− melanoma model (n=6). Data are representative of 3 independent experiments. (D) qRT-PCR analysis of Cxcl1, Cxcl2, and Cxcl5 in the BRAFV600E PTEN−/− melanoma cell line following treatment with rWnt5a versus vehicle control (n=3). (E) Western blot analysis of YAP1 expression in total cellular lysates (top) and nuclear lysates (middle) following treatment of BRAFV600E PTEN−/− melanoma cells with rWnt5a at various time points. Bottom blot shows Wnt5a induction of CXCL5 with or without verteporfin (YAP inhibitor) or XAV939 (0-catenin inhibitor). Blots shown are representative of 3 independent experiments. UT, untreated or vehicle control. (F) qRT-PCR analysis of Cxcl5 in BRAFV600E PTEN−/− NTC and Wnt5a-silenced BRAFV600E PTEN−/− melanoma cells (BRAFV600E PTEN−/− Wnt5aKD). Blot shows secreted CXCL5 in BRAFV600E PTEN−/− NTC and BRAFV600E PTEN−/− Wnt5aKD cells (n=3). (G) IHC for CXCL5 (red) in BRAFV600E PTEN−/− NTC and BRAFV600E PTEN−/− Wnt5aKD tumor cells. Images are representative of 3 tumors. White arrows indicate CXCL5+ tumor cells. Original magnification, ×20. (H) IHC for Gr-1 in BRAFV600E PTEN−/− NTC and BRAFV600E PTEN−/− Wnt5aKD tumor cells. Original magnification, ×20. Plots show PMN-MDSC flow cytometric analysis of BRAFV600E PTEN−/− NTC and BRAFV600E PTEN−/− Wnt5aKD tumors (n=3). (I) PMN-MDSC flow cytometric analysis of BRAFV600E PTEN−/− NTC and BRAFV600E PTEN−/− Wnt5aKD tumors following treatment with anti-PD-1 Ab versus IgG isotype control (n=5). (J) Tumor volume change based on anti-PD-1 Ab/IgG control ratios for BRAFV600E PTEN−/− NTC and BRAFV600E PTEN−/− Wnt5aKD tumors (n=5). α, anti. UT, untreated control. Kendall's tau correlation coefficient was calculated for A. *$P<0.05$ and ***$P<0.0005$, by Student's t test (C, D, and I) and 1-way ANOVA with Sidak's post hoc multiple comparisons test (F). See also FIG. 10.
Figures 2H, 2I, 2J:
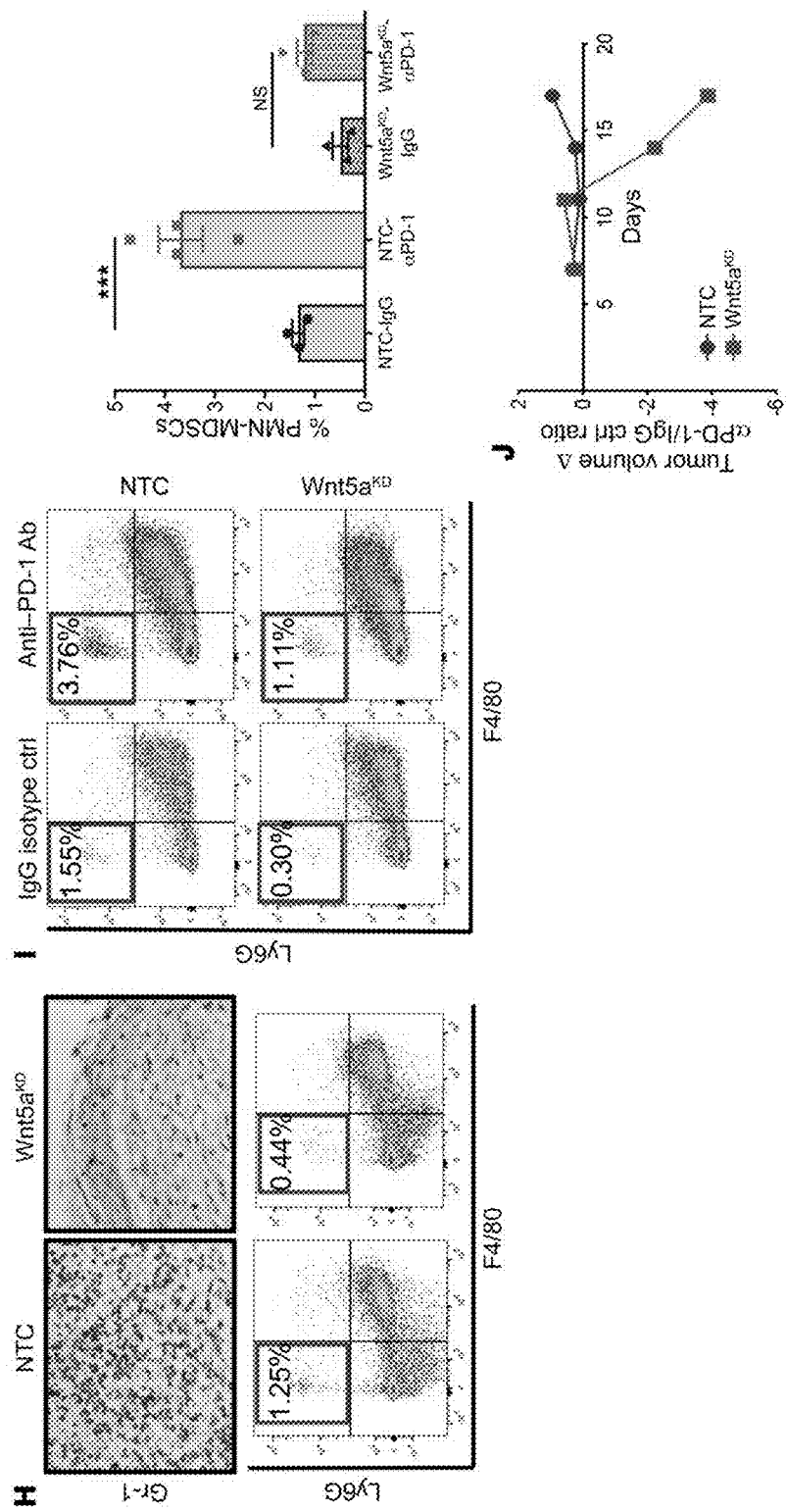

The differential whole transcriptomic analysis of the autochthonous $BRAF^{V600E}PTEN^{-/-}$ melanoma model subjected to anti-PD-1 ab versus IgG isotype control ab therapy also demonstrated several genetic changes suggestive of enhanced Wnt ligand signaling during anti-PD-1 ab escape (FIG. 10A). Additional analysis of transcriptomic data for patients with metastatic melanoma in the The Cancer Genome Atlas-SKCM (TCGA-SKCM) database also revealed a statistically significant association between WNT5A and CXCL2, CXCL5, and CXCR2 gene expression (FIG. 2A). Previous studies have shown that noncanonical Wnt ligands activate Yes-associated protein-dependent (YAP-dependent) signaling pathways, whereas YAP signaling has also been implicated in the migration of PMN-MDSCs into tumor tissues (27, 28). Consistent with these data, we performed whole-tissue Western blot analysis and found that resected melanoma tissues derived from the autochthonous BRAFV600E PTEN-/- model had enhanced Wnt5a expression, YAP stabilization, and increased CXCL5 expression in response to anti-PD-1 Ab therapy (FIG. 2B). This enhanced level of CXCL5 expression by the tumor was also reflected by increased circulating plasma CXCL5 levels as determined by ELISA (FIG. 2C). We performed further in vitro studies using qRT-PCR, which confirmed that recombinant Wnt5a (rWnt5A) induced Cxcl2, Cxcl5, and Cxcl1 gene expression in the BRAFV600E PTEN−/− melanoma cell line (FIG. 2D). Given these findings, we hypothesized that upregulation of Wnt5a results in enhanced CXCR2-dependent chemokine expression by triggering the YAP signaling pathway. Further experiments using the BRAFV600E PTEN−/− melanoma cell line indeed showed that rWnt5a induced YAP stabilization, while also stimulating CXCL5 expression in a YAP-dependent manner (FIG. 2E). To confirm the role of Wnt5a in the upregulation of CXCL5 in the BRAFV600E PTEN−/− melanoma cell line, qRT-PCR further revealed diminished CXCL5 expression in a Wnt5a-knockdown (Wnt5aKD) BRAFV600E PTEN−/− melanoma cell line (BRAFV600E PTEN−/− Wnt5aKD), an effect that could be rescued with the addition of rWnt5a (FIG. 2F and FIG. 10B). Additional studies using flow cytometry and IC showed that BRAFV600E PTEN−/− Wnt5aKD tumors had reduced CXCL5 expression and an associated decrease in intratumoral PMN-MDSCs, respectively (FIGS. 2, G and H). On the basis of these data, we hypothesized that the previously observed recruitment of PMN-MDSCs to the tumor bed in response to anti-PD-1 Ab therapy would be eliminated in tumors silenced for Wnt5a expression. Indeed, PMN-MDSC recruitment to BRAFV600E PTEN−/− Wnt5aKD tumors was significantly diminished relative to control BRAFV600E PTEN−/− tumors in response to anti-PD-1 Ab therapy (FIG. 2I). Consistent with an important role for PMN-MDSCs in driving immunotherapy resistance, we also found BRAFV600E PTEN−/− Wnt5aKD tumors to be associated with increased CD8+ T cell infiltration and to respond more favorably to anti-PD-1 Ab therapy relative to control BRAFV600E PTEN−/− tumors (FIG. 2J and FIG. 10C). Altogether, these findings support a role for tumor-derived Wnt5a as an important mediator of CXCL5-dependent PMNMDSC recruitment to the tumor bed in response to anti-PD-1 Ab checkpoint inhibitor immunotherapy.

An Autocrine HSP70-TLR4 Signaling Pathway Stimulates Tumor Wnt5a Release in Response to Anti-PD-1 Immunotherapy.

Figures 3A, 3B, 3C, 3D, 3E, 3F, 3G:
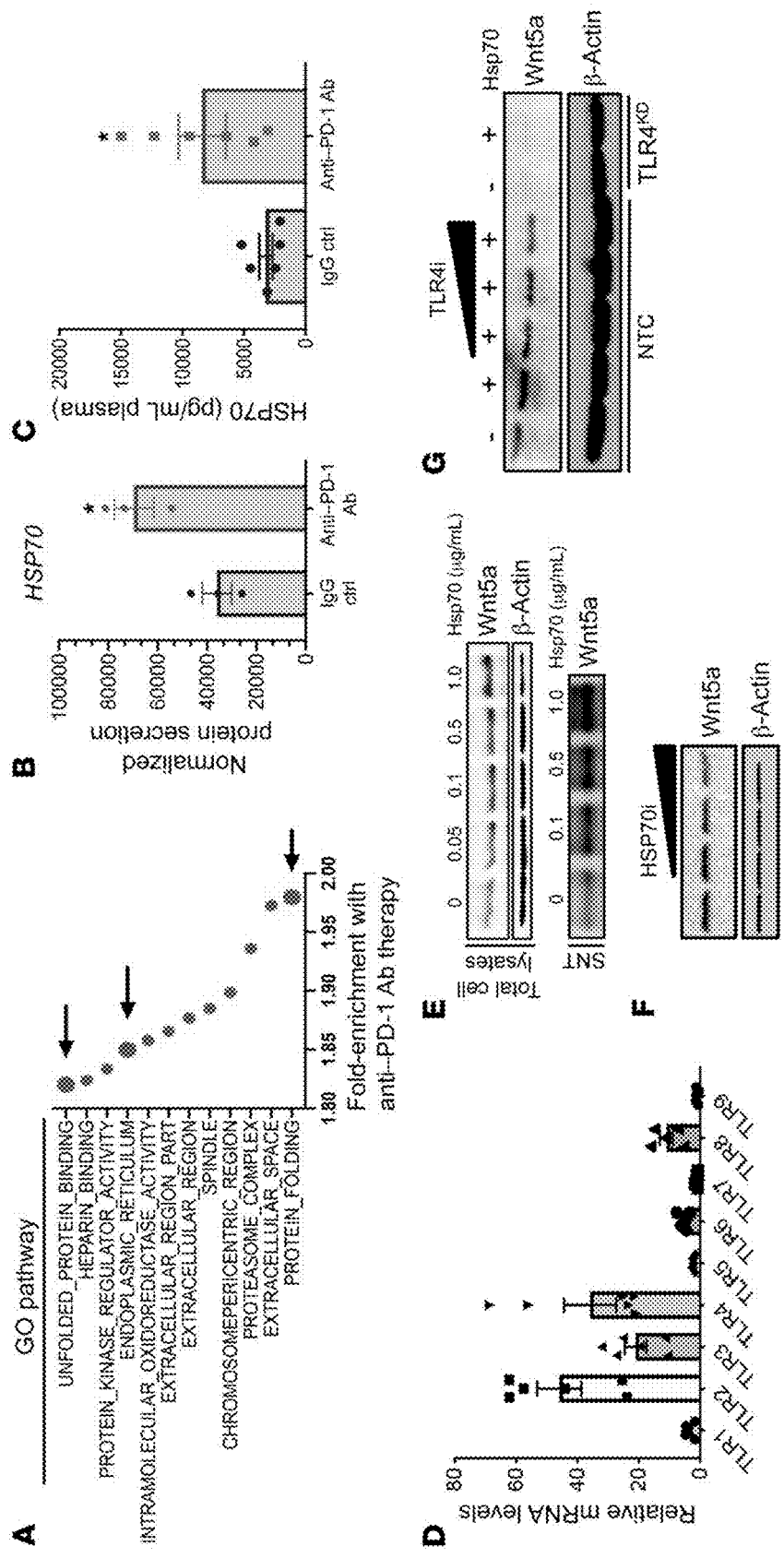
FIG. 3A-J. HSP70-TLR4 induces Wnt5a expression in response to anti-PD-1 Ab immunotherapy. (A) RNA-Seq GSEA showing top 12 pathways enriched in autochthonous BRAFV600E PTEN−/− melanomas following escape from anti-PD-1 Ab therapy. Arrows indicate pathways associated with cellular stress (n=3/group). (B) SILAC-AHA LC-MS/MS secretome analysis of resected autochthonous BRAFV600E PTEN−/− melanoma tissues following anti-PD-1 Ab therapy versus IgG isotype control. Secreted protein levels were normalized to the number of cells (n=3/group). (C) Plasma HSP70 ELISA analysis following anti-PD-1 versus IgG isotype control treatment of autochthonous BRAFV600E PTEN$^{-/-}$ melanoma-bearing mice (n=6). (D) qRT-PCR analysis of TLR expression in BRAFV600E PTEN−/− melanoma cells. Data were normalized to Tlr9 expression levels (n=3). (E) Treatment of BRAFV600E PTEN−/− melanoma cells with titrated concentrations of recombinant HSP70 (rHSP70) followed by Wnt5a Western blot analysis of total cell lysates and supernatant (SNT). Blots are representative of 2 independent experiments. (F) Treatment of BRAFV600E PTEN−/− melanoma cells with titrated concentrations of the HSP70 inhibitor VER155008 (HSP70i). Blots are representative of 2 independent experiments. (G) Treatment of BRAFV600E PTEN−/− NTC cells with rHSP70 with or without the TLR4 inhibitor CLI-095 (TLR4i) and treatment of Tlr4-silenced BRAFV600E PTEN−/− melanoma cells (TLR4KD) with HSP70 followed by Western blotting for Wnt5a. Blots are representative of 3 independent experiments. (H) BRAFV600E PTEN−/− melanoma growth curve following treatment with TLR4 siRNA versus control siRNA (n=5). (I) Whole-tissue Western blot analysis of Wnt5a, CXCL5, and β-actin in TLR4 siRNA-treated and control siRNA-treated BRAFV600E PTEN−/− melanomas. Data are representative of 2 independent experiments. (J) Top: PMN-MDSC flow cytometric analysis of TLR4 siRNA- and control siRNA-treated BRAFV600E PTEN−/− melanomas (n=4). Bottom: CD8+ T cell flow cytometric analysis of TLR4 siRNA- and control siRNA-treated BRAFV600E PTEN−/− melanomas (n=4). *P<0.05, by Student's t test for comparison of treatment groups. See also FIG. 11.
Figures 3H, 3I, 3J:
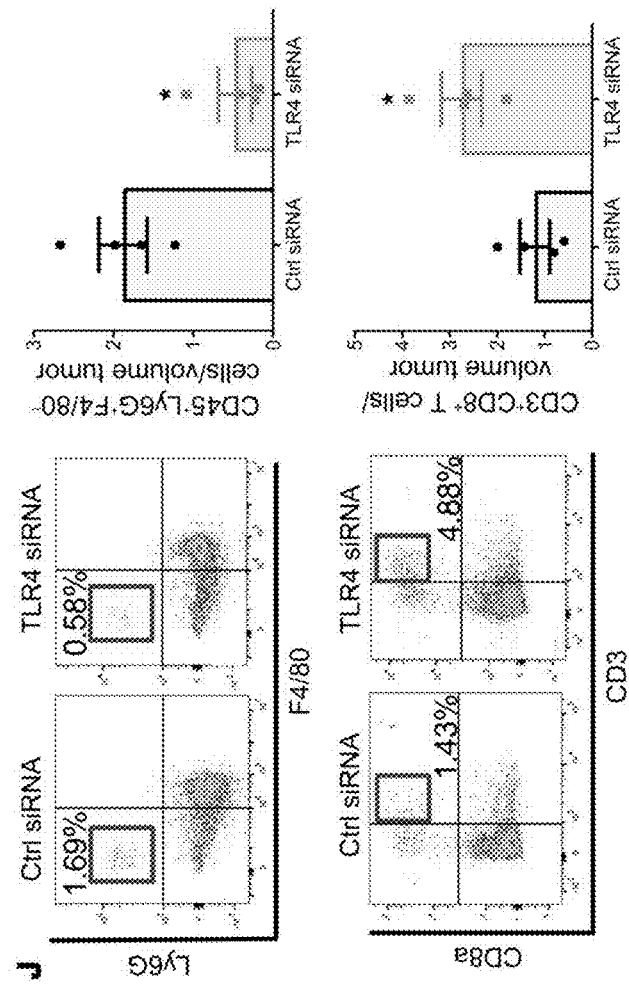
Figures 11A, 11B, 11C, 11D, 11E, 11F:
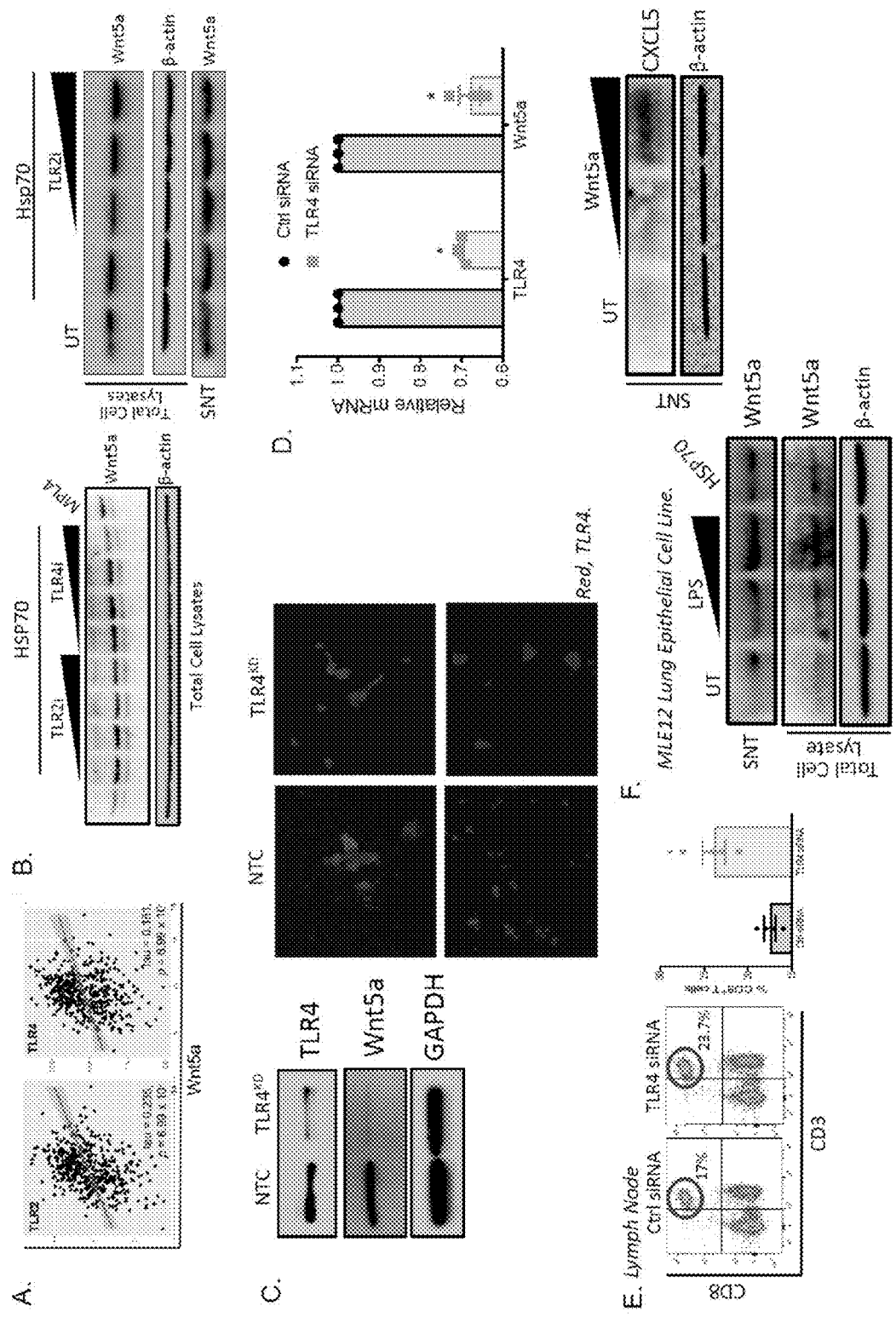

Given our previous data, we then investigated the underlying mechanism for Wnt5a upregulation in response to anti-PD-1 ab therapy in the $BRAF^{V600E}PTEN^{-/-}$ melanoma model. Prior studies have shown TLR signaling to modulate Wnt5a expression in macrophages (20). Heat shock proteins (HSPs) are known to bind and induce the activation of toll-like receptor (TLR) signaling pathways (29). A review of the previous whole transcriptomic data analysis performed in the autochthonous $BRAF^{V600E}PTEN^{-/-}$ melanoma model showed anti-PD-1 ab therapy to result in increased expression of several genes associated with cellular stress, including a subset of HSPs (FIG. 3A) (30). To investigate this further, we analyzed the secretome of resected BRAFV600E PTEN−/− melanoma tissues following escape from anti-PD-1 Ab immunotherapy, using liquid chromatography-tandem mass spectrometry (LC-MS/MS) and the stable isotope labeling with amino acids in cell culture (SILAC) technique coupled with azidohomoalanine (AHA) labeling (31). This work showed further evidence of increased release of HSPs, including HSP70, in those tumors that had escaped anti-PD-1 Ab immunotherapy relative to IgG isotype Ab control-treated tumors (FIG. 3B). Consistent with these data, we also found that melanoma-bearing mice undergoing anti-PD-1 Ab treatment had increased circulating plasma HSP70 levels relative to levels in mice treated with an IgG isotype control Ab (FIG. 3C). A qRT-PCR-based screen identified elevated levels of Tlr2 and Tlr4 expression by BRAFV600E PTEN−/− melanoma cells relative to other TLRs, and an analysis of TCGA database also revealed a compelling relationship between Wnt5a and TLR2 and TLR4 expression in human melanoma (FIG. 3D and FIG. 11A). Consistent with this, we found that HSP70 stimulation of the BRAFV600E PTEN−/− melanoma cell line induced upregulation of Wnt5a expression in a dose-dependent manner, whereas pharmacologic inhibition of HSP70 suppressed autocrine stimulation of Wnt5a expression (FIGS. 3, E and F). Subsequent pharmacologic inhibitor and genetic silencing studies using a shRNA-expressing lentiviral vector revealed that HSP70 stimulation of melanoma Wnt5a expression was TLR4 dependent (FIG. 3G and FIGS. 11, B and C). Interestingly, these BRAFV600E PTEN−/− melanoma cells genetically silenced for Tlr4 did not generate tumors in vivo following their implantation. Even with modest Tlr4 silencing using siRNA oligonucleotides, these melanomas exhibited diminished tumor growth, reduced Wnt5a and CXCL5 expression based on whole-tissue Western blot analysis, and a lower level of tumor-infiltrating PMN-MDSCs along with enhanced numbers of CD8+ T cells compared with control BRAFV600E PTEN−/− melanomas (FIG. 3, H-J, and FIGS. 11, D and E). To verify that HSP70 induction of the Wnt5a/CXCL5 signaling axis is not a specific phenomenon related to melanoma, we also repeated these experiments in a murine lung epithelial cell line with similar results (FIG. 11F). In summary, these data suggest that tumor HSP70 release in response to anti-PD-1 Ab treatment induces Wnt5a-mediated upregulation of CXCR2-dependent chemokine expression in tumor tissues. CD8+ T Cells Drive the HSP70/TLR4/Wnt5a/CXCL5 Signaling Axis in Tumors.

Figures 4A, 4B, 4C, 4D, 4E, 4F, 4G, 4H:
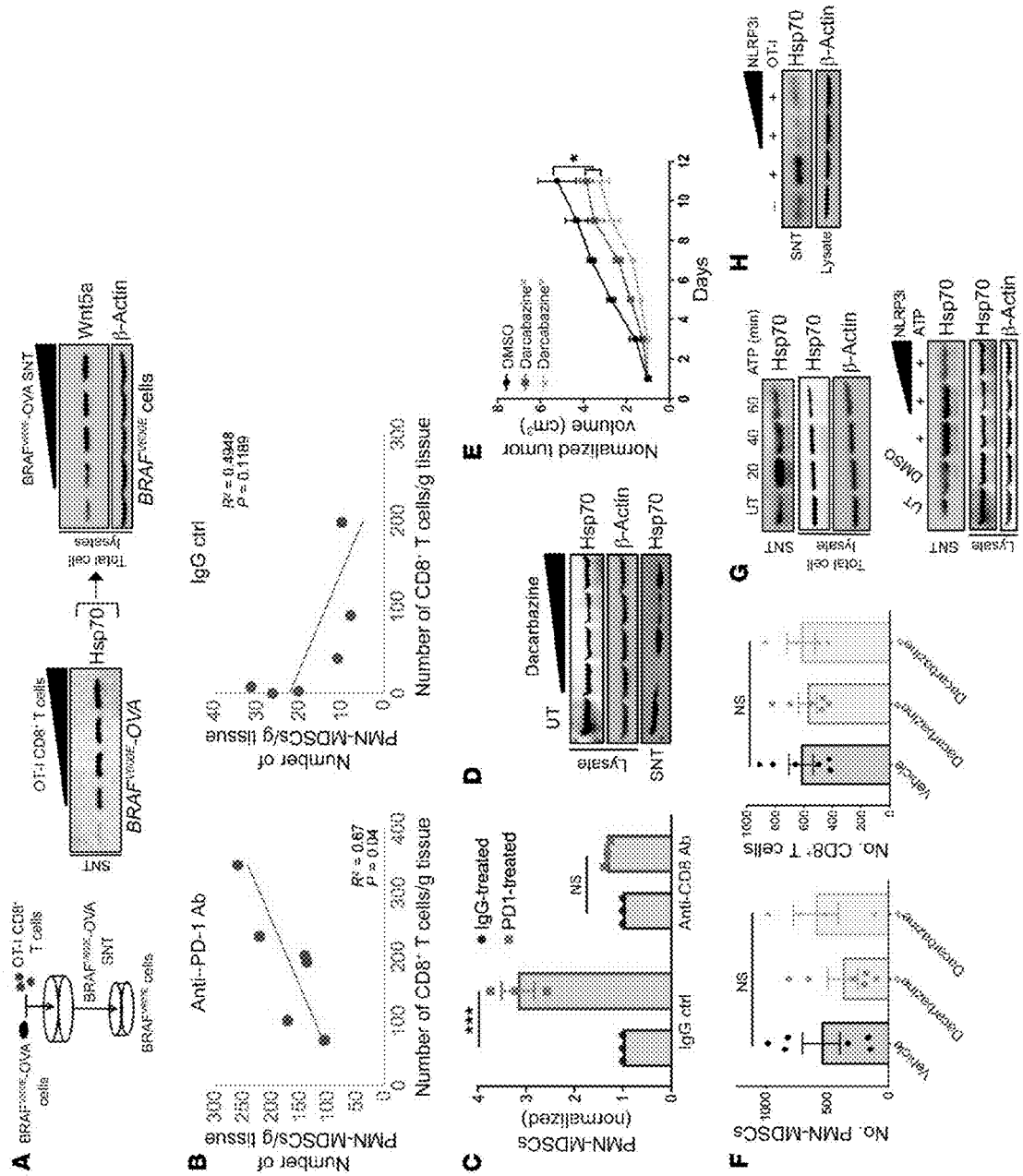
FIG. 4A-H. CD8+ T cells induce tumor HSP70 release in a NLRP3-dependent manner in response to anti-PD-1 Ab immunotherapy. (A) Schema illustrating coculture of OT-I CD8+ T cells with OVA-expressing BRAFV600E PTEN−/− melanoma cells followed by HSP70 Western blot analysis of isolated supernatant. Harvested supernatant was coincubated at increasing concentrations with WT BRAFV600E PTEN−/− melanoma cells followed by Wnt5a Western blot analysis. Blots are representative of 2 independent experiments. (B) Flow cytometric analysis of PMN-MDSCs and CD8+ T cells from resected autochthonous BRAFV600E PTEN−/− melanoma tissues following anti-PD-1 Ab or IgG isotype control therapy. Results are expressed per gram of tumor tissue (n=6). (C) Flow cytometric analysis of tumor-infiltrating PMN-MDSCs from autochthonous BRAFV600E PTEN−/− melanomas following anti-PD-1 Ab versus IgG isotype control therapy with or without anti-CD8 Ab. Data were normalized to IgG control-treated tumors (n=3). (D) HSP70 and β-actin Western blot analysis following treatment of BRAFV600E PTEN−/− melanoma cells with increasing concentrations of dacarbazine. Blots are representative of 3 independent experiments. (E) Tumor growth curve of syngeneic BRAFV600E PTEN−/− melanomas following vehicle control or low-dose (lo) (50 mg/kg i.p. q.o.d.) or high-dose (hi) (75 mg/kg i.p. q.o.d.) dacarbazine therapy (n=5). (F) Flow cytometric analysis of PMN-MDSCs from BRAFV600E PTEN−/− melanomas following vehicle control or dacarbazine therapy (n=5). Flow cytometric analysis of CD8+ T cells from BRAFV600E PTEN−/− melanomas following vehicle control or dacarbazine therapy (n=5). (G) HSP70 Western blot analysis of supernatant and tumor cell lysates following ATP stimulation of BRAFV600E PTEN−/− melanoma cells at different time points, with or without treatment with the NLRP3 inhibitor (NLRP3i) MCC950. Blots are representative of 3 independent experiments. (H) HSP70 Western blot following coincubation of OT-1 CD8+ T cells and OVA-expressing BRAFV600E PTEN−/− melanoma cells with or without increasing concentrations of NLRP3 inhibitor. Blots are representative of 3 independent experiments. Spearman's correlation calculation was performed in B. *P<0.05 and ***P<0.0005, by Student's t test (C), 1-way ANOVA with Sidak's post hoc multiple comparisons test (E and F). See also FIG. 12.
Figures 12A, 12B, 12C, 12D:
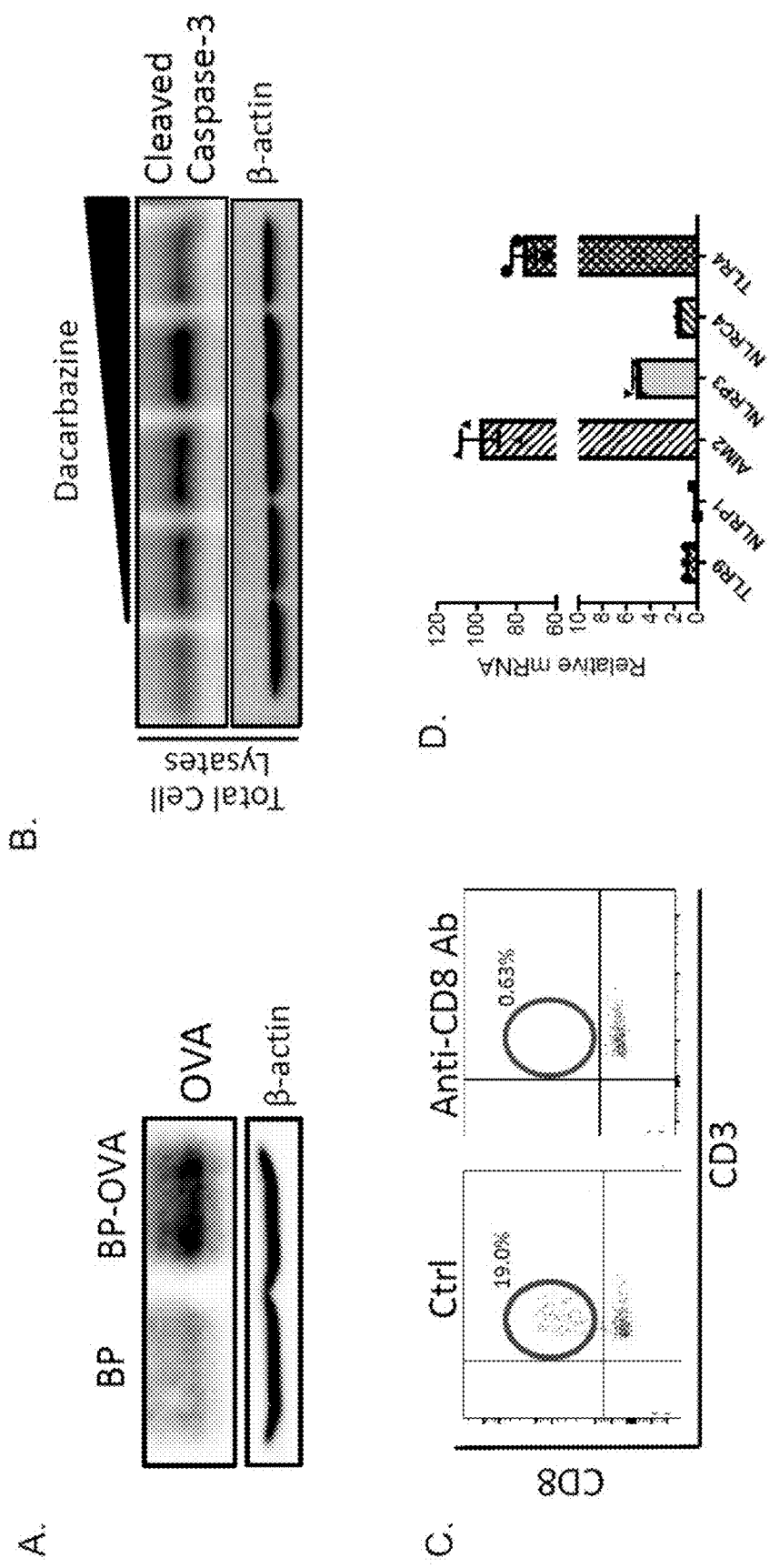

Since our data indicated that PMN-MDSC recruitment was induced by anti-PD-1 Ab therapy, we hypothesized that CD8+ T cells play an important role in triggering the HSP70/TLR4-Wnt5a/CXCL5 signaling cascade. We therefore cocultured increasing numbers of OT-1 Kb-SIINFEKL-specific CD8+ T cells with a BRAFV600E PTEN−/− melanoma cell line engineered to express the OVA xenoantigen (BRAFV600E OVA) and measured the soluble production of HSP70 (FIG. 12A). This approach showed a direct correlation between antigen-specific CD8+ T cells, tumor HSP70 secretion, and the induction of Wnt5a expression in vitro (FIG. 4A). Further flow cytometric analysis of resected BRAFV600E PTEN−/− melanoma tissues also revealed a linear relationship between the number of infiltrating CD8+ T cells and the number of PMN-MDSCs per gram of tissue following anti-PD-1 Ab therapy but not in response to IgG isotype control Ab therapy (FIG. 4B). In line with our previous results showing that the elimination of CD8+ T cells abolished the increase in tumor CXCL5 expression with anti-PD-1 Ab therapy (FIG. 1F), further in vivo experiments showed that Ab-mediated ablation of CD8+ T cells also diminished PMN-MDSC recruitment in response to anti-PD-1 Ab therapy (FIG. 4C and FIG. 12C). Together, these data suggest that CD8+ T cell activity contributes to the induction of PMN-MDSC recruitment and that this process involves tumor-dependent secretion of HSP70.

Since HSP release by tumors could be interpreted to be due simply to tumor cell death, we inquired whether cytotoxic chemotherapy could induce similar effects. Dacarbazine chemotherapy has historically been used for the management of metastatic melanoma. Although dacarbazine was capable of inducing BRAFV600E PTEN−/− melanoma cell death in vitro, this process was not associated with increased HSP70 release (FIG. 4D and FIG. 12B). Consistent with this effect, dacarbazine suppressed BRAFV600E PTEN−/− melanoma progression in vivo but did not influence the recruitment of PMN-MDSCs or the numbers of tumor-infiltrating CD8+ T cells (FIGS. 4, E and F).

In light of these findings, we investigated the mechanism regulating tumor HSP70 secretion in response to CD8+ T cell activity. Prior studies have implicated ATP as a stimulator of HSP70 release (32). Since ATP is also a classic activator of the NLRP3 inflammasome, we hypothesized that NLRP3 played a role in promoting the release of HSP70 using a similar mechanism responsible for its induction of IL-1β and IL-18 secretion (33). To address this question, we conducted in vitro experiments, which showed that a NLRP3 inhibitor could block both ATP stimulation and CD8+ T cell-mediated induction of HSP70 release from the BRAFV600E PTEN−/− melanoma cell line (FIGS. 4, G and H). These results support a potential role for the tumor NLRP3 inflammasome in CD8+ T cell-mediated HSP70 release and the observed stimulation of PMN-MDSC recruitment.

PD-L1 Triggers NLRP3 Activation and Downstream Activation of the HSP70/Wnt5a Signaling Axis in Tumors.

Figures 5A, 5B, 5C, 5D, 5E, 5F:
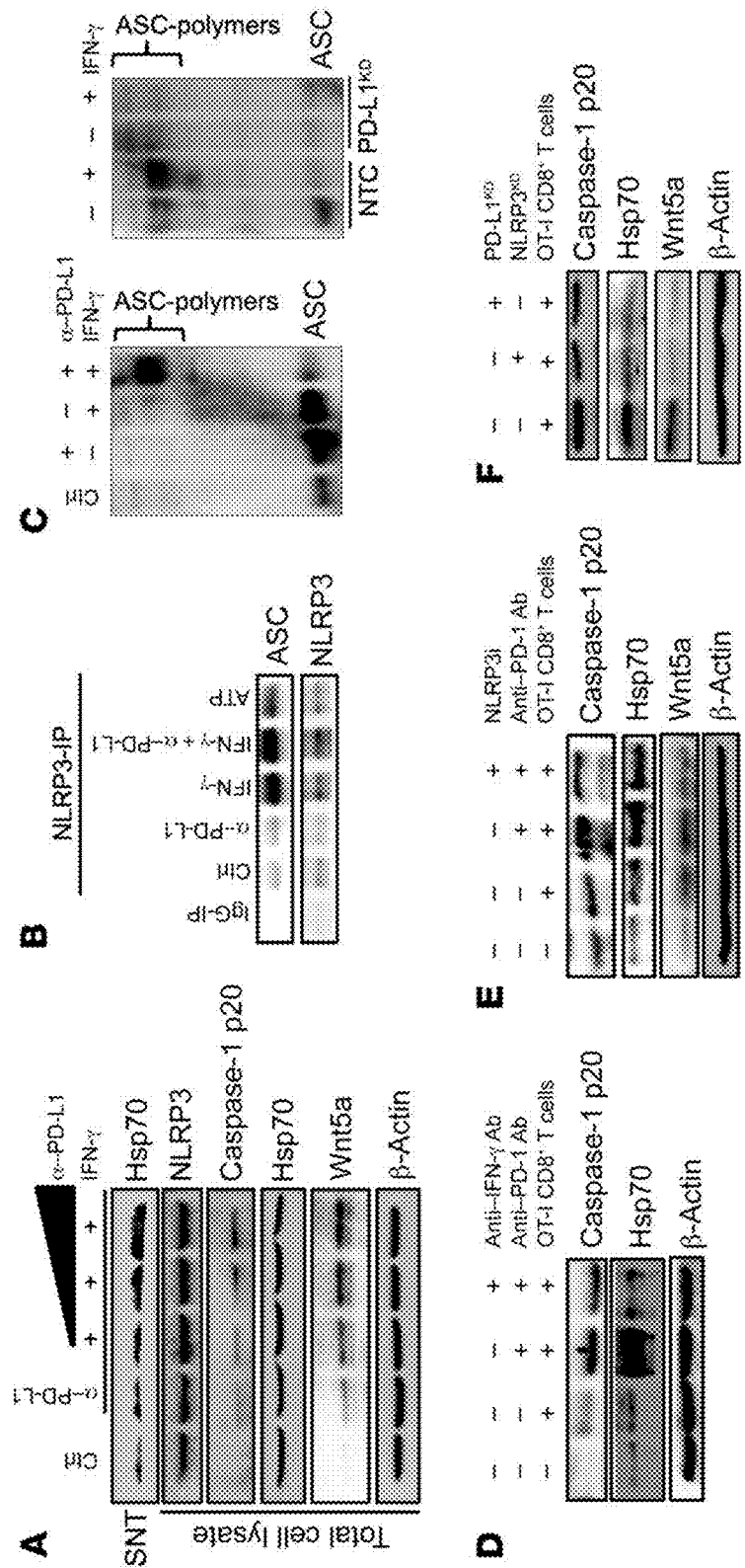
FIG. 5A-K CD8+ T cells trigger a PD-L1/NLRP3 signaling pathway to drive PMN-MDSC recruitment to the tumor. (A) Western blots for HSP70 supernatant, caspase-1 p20, and Wnt5a in BRAFV600E PTEN−/− melanoma cells treated with anti-PD-L1 Ab with or without IFN-7. (B) Immunoprecipitation (IP) of NLRP3 after treatment of BRAFV600E PTEN−/− melanoma cells with IFN-γ, anti-PD-L1, or both followed by Western blotting for ASC and NLRP3. IgG-IP, IP control; ATP, positive control. (C) Left: ASC polymerization assay following treatment of BRAFV600E PTEN−/− melanoma cells with IFN-γ, anti-PD-L1, or both. Right: ASC polymerization assay following treatment of Pdl1-silenced and NTC BRAFV600E PTEN−/− melanoma cells with IFN-7. (D) Coculture of OT-I CD8+ T cells with OVA-expressing BRAFV600E PTEN−/− melanoma cells, with or without anti-PD-1 Ab alone or anti-PD-1 Ab plus anti-IFN-γ-blocking Ab, was followed by Western blotting for HSP70 and caspase-1 p20. (E) Coculture of OT-I CD8+ T cells with BRAFV600E PTEN−/− OVA melanoma cells, with or without anti-PD-1 Ab alone or anti-PD-1 Ab plus NLRP3 inhibitor, was followed by Western blots for caspase-1 p20, HSP70, and Wnt5a. (F) Western blots for caspase-1 p20, HSP70, and Wnt5a Western blots in BRAFV600E PTEN−/− OVA melanoma cells following coculture with OT-I CD8+ T cells after genetic silencing of either Nlrp3 (NRLP3KD) or PdlI (PD-L1KD). (G) IP of NLRP3 after treatment of BRAFV600E PTEN−/− melanoma cells with IFN-γ, anti-PD-L1, or both, followed by Western blotting for PKR and NLRP3. (H) Western blots for p-PKR and total PKR in control and Pdl1-silenced BRAFV600E PTEN−/− melanoma cells. GAPDH was used as a cytoplasmic loading control and laminin B as a nuclear loading control. (I) Western blotting for STAT3, p-PKR, and total PKR in control and Pdl1-silenced BRAFV600E PTEN−/− melanoma cells. (J) Western blots for caspase-1 p20 and Wnt5a in WT and STAT3CA-expressing BRAFV600E PTEN−/− melanoma cells following treatment with IFN-γ, anti-PD-L1, or both. (K) Schematic diagram depicting the PD-L1/STAT3/PKR/NLRP3 signaling axis in tumor cells. cyt, cytoplasm. All Western blots are representative of 2-3 independent experiments. See also FIG. 13.
Figures 13A, 13B, 13C:
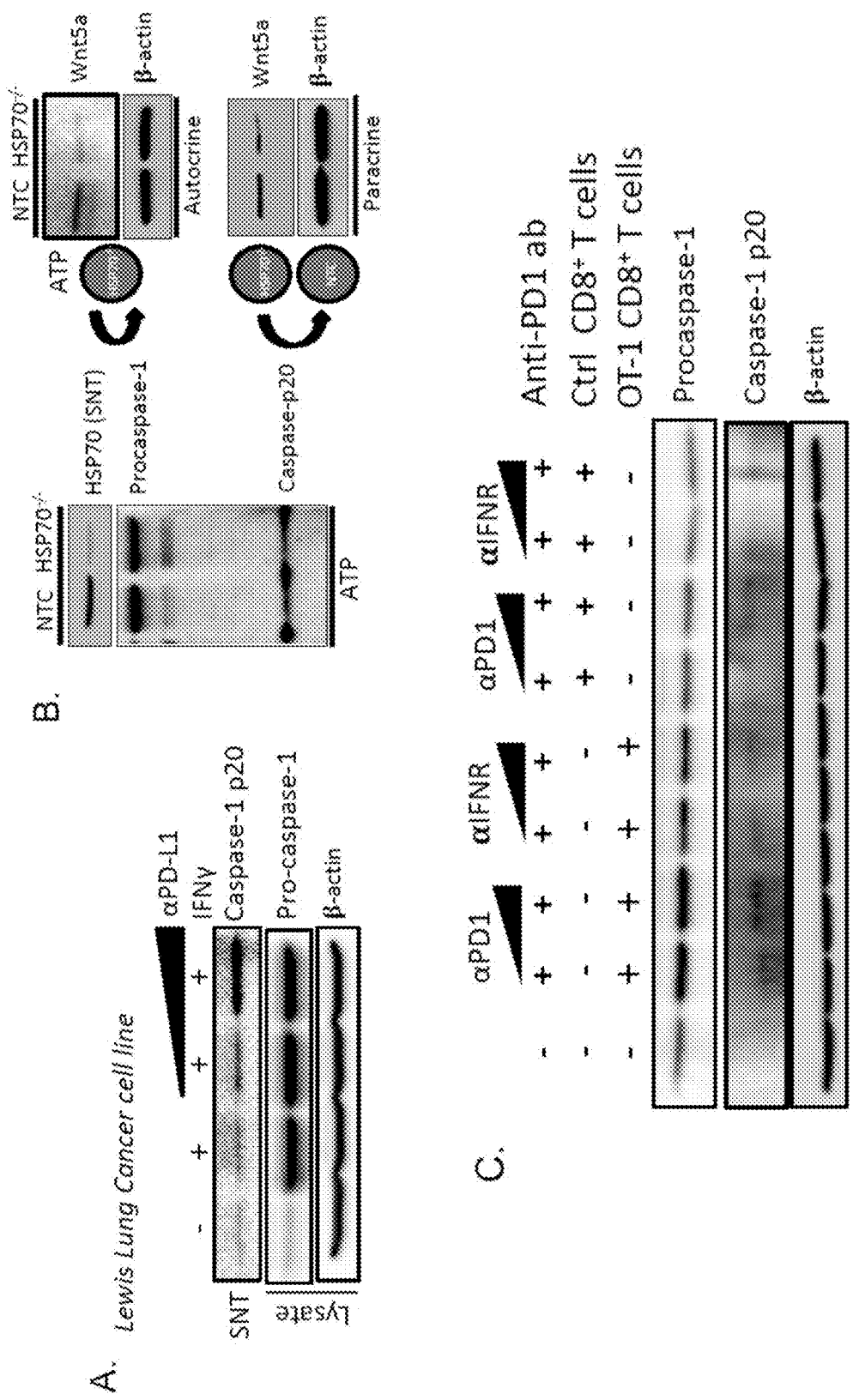
Figures 13D, 13E, 13F:
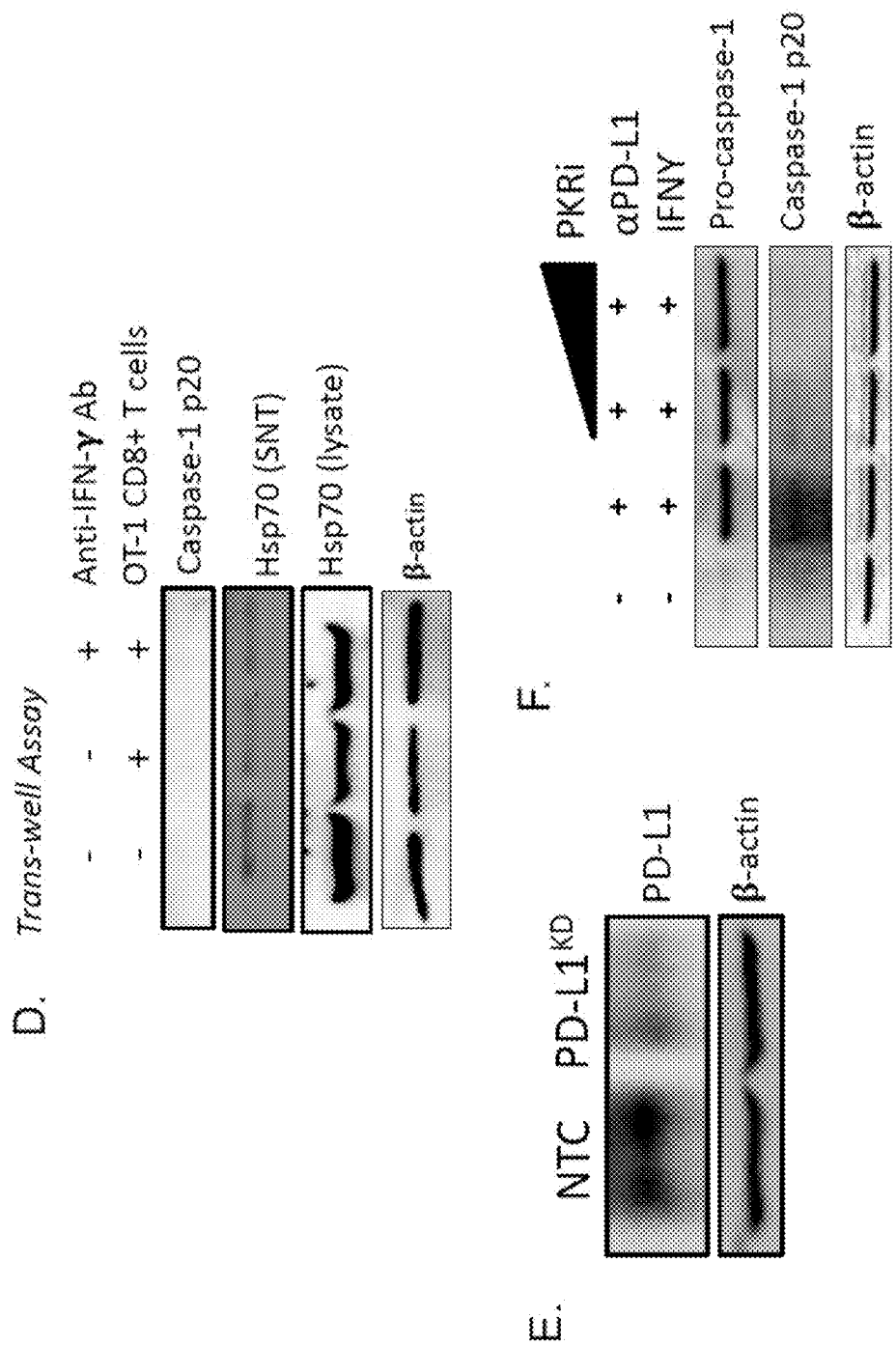

In view of the relationship between infiltrating T cells and the induction of PD-L1 in the tumor microenvironment via IFN signaling, we further conjectured that release of HSPs from tumors and stimulation of the NLRP3/HSP70 signaling axis are dependent on PD-L1 upregulation (15). To test this hypothesis, we coincubated BRAFV600E PTEN−/− melanoma cells with IFN-γ in the absence and presence of an agonistic anti-PD-L1 Ab and monitored for HSP70 release as well as for evidence of caspase-1 cleavage as a surrogate for NLRP3 activation. This study showed that anti-PD-L1 Ab plus IFN-γ treatment of BRAFV600E PTEN−/− melanoma cells indeed induced activation of the NLRP3 inflammasome, concurrent release of HSP70, and upregulation of Wnt5a (FIG. 5A). This effect was also observed in the LLC cell line, indicating that this phenomenon is not restricted to the BRAFV600E PTEN−/− melanoma model (FIG. 13A). To further confirm the sequence of this signaling pathway, we genetically silenced HSP70 using a CRISPR/Cas9 approach in the BRAFV600E PTEN−/− melanoma cell line and stimulated the upstream NLRP3 inflammasome in these BRAFV600E PTEN−/− HSP70−/− cells along with their nontarget control (NTC) cell line. These experiments showed that HSP70 ablation eliminated the ability of the NLRP3 inflammasome to stimulate the upregulation of Wnt5a in both an autocrine and paracrine manner (FIG. 13B). Further experiments demonstrated that tumor cell PD-L1 cross-linking induced NLRP3 binding to the apoptosis-associated speck-like protein containing a caspase recruitment domain (ASC) adaptor protein, while also promoting ASC polymerization, both of which were necessary to generate the inflammasome macromolecular complex (FIGS. 5, B and C). We then verified that PD-1 blockade promotes CD8+ T cell induction of NLRP3 activation and tumor HSP70 release in an IFN-γ-dependent manner in further OT-1 CD8+ T cell:BRAFV600E OVA melanoma coculture experiments (FIG. 5D). Notably, this induction of NLRP3 activation by CD8+ T cells was found to be antigen specific, as CD8+ T cells that recognize an irrelevant control peptide do not induce caspase-1 activation (FIG. 13C). Furthermore, this phenomenon required T cell-tumor cell contact or close proximity, as Transwell assays failed to induce caspase-1 cleavage and HSP70 release, consistent with an important role for physical PD-1-PD-L1 interactions (FIG. 13D). Importantly, both the pharmacologic inhibition and genetic silencing of Nlrp3 effectively suppressed HSP70 release and subsequent Wnt5a upregulation in response to anti-PD-1 Ab activation of tumor antigen-specific CD8+ T cells (FIGS. 5, E and F). We observed a similar effect with genetic silencing of Pdl1 in the BRAFV600E PTEN−/− melanoma cell line, which resulted in elimination of ASC polymerization, caspase-1 activation, HSP70 secretion, and Wnt5a upregulation (FIGS. 5, C and F, and FIG. 13E).

Figures 5G, 5H, 5I, 5J, 5K:
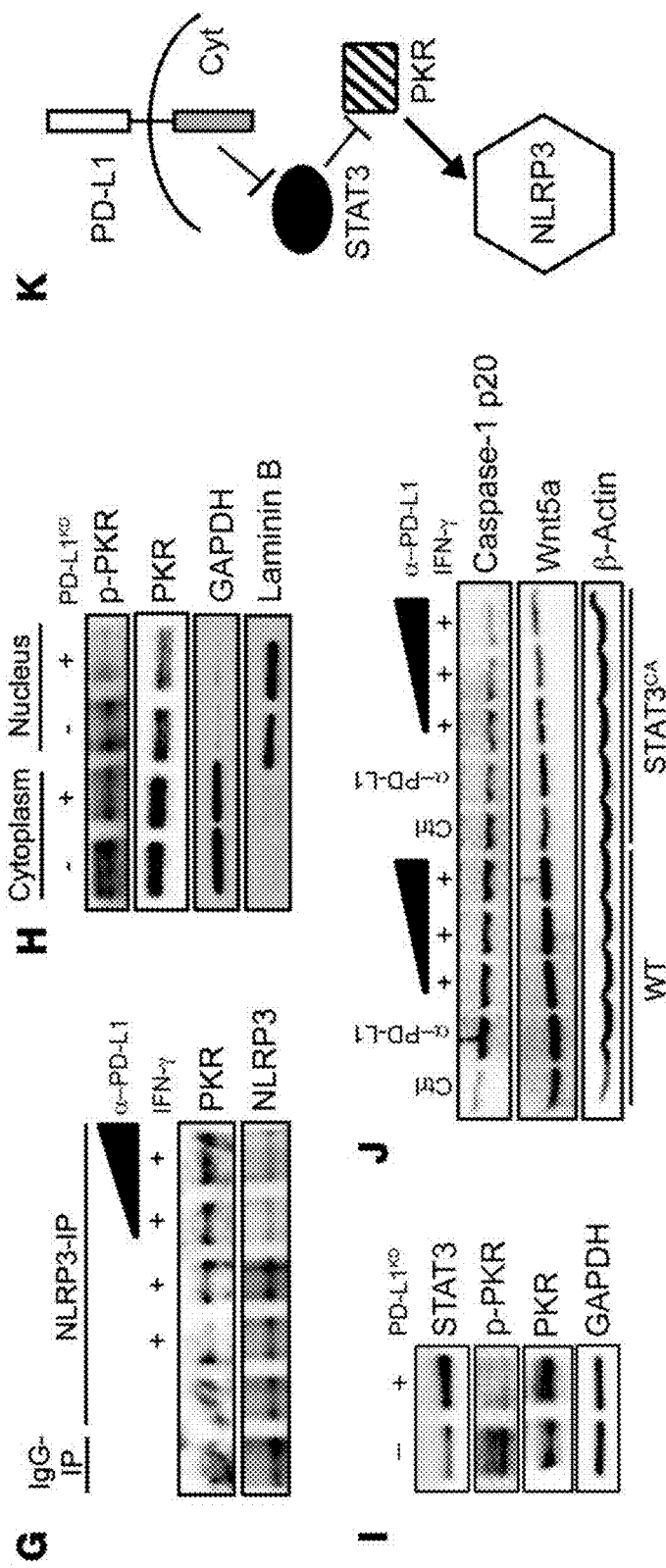

On the basis of these data, we examined the mechanism mediating PD-L1-dependent NLRP3 activation. dsRNA-dependent protein kinase R (PKR) is a known activator of all inflammasome proteins, including NLRP3, and has been shown to regulate certain inflammatory pathways (34). Indeed, PKR inhibition suppressed caspase-1 cleavage in the BRAFV600E PTEN−/− melanoma cell line in response to anti-PD-L1 Ab/IFN-γ stimulation (FIG. 13F). Consistent with these studies, further treatment of BRAFV600E PTEN−/− melanoma cells with anti-PD-L1 Ab and IFN-γ induced PKR-NLRP3 binding, whereas genetic silencing of Pdl1 also suppressed PKR phosphorylation (FIGS. 5, G and H). A recent report has shown that tumor-intrinsic PD-L1 signaling inhibits STAT3 activation (23). Previous work has also shown that cytosolic STAT3 inhibits PKR kinase activity and suppresses activation of the NLRP3 inflammasome (35, 36). We therefore hypothesized that tumor PD-L1 promotes PKR-NLRP3 activation by suppressing STAT3 levels. Indeed, we found that Pdl1 silencing upregulated total STAT3 levels concurrently with diminished PKR phosphorylation (FIG. 5I). Consistent with a suppressive role for STAT3 in this pathway, we found that constitutive activation of STAT3 (STAT3CA) suppressed NLRP3 activation, as indicated by the diminished caspase-1 cleavage and Wnt5a expression levels (FIG. 5J). These data indicate that PD-L1 triggers PKR-dependent activation of the NLRP3 inflammasome in tumors by repressing STAT3 (FIG. 5K). In summary, we have elucidated a mechanistic link between PD-L1 and the tumor-intrinsic NLRP3 inflammasome and showed that this pathway drives adaptive immune evasion by promoting the recruitment of PMN-MDSCs.

Genetic and Pharmacologic Inhibition of NLRP3 Blocks PMN-MDSC Recruitment and Enhances the Efficacy of Anti-PD-1 Antibody Immunotherapy.

Figures 6A, 6B, 6C, 6D, 6E:
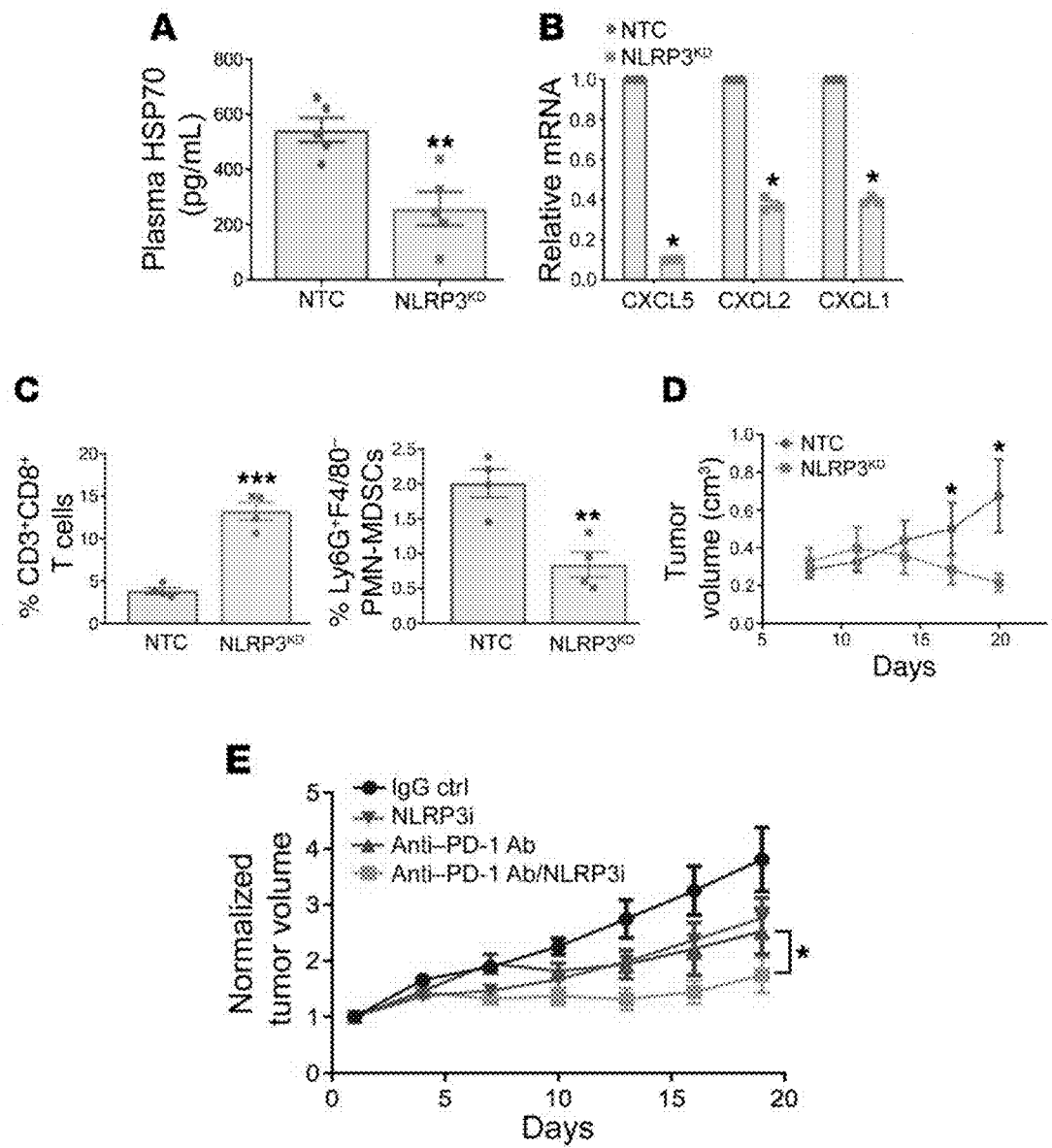
FIG. 6A-H. Genetic and pharmacologic inhibition of NLRP3 suppresses PMN-MDSC recruitment and enhances the efficacy of anti-PD-1 Ab immunotherapy. (A) Plasma HSP70 ELISA analysis following the growth of BRAFV600E PTEN−/− NTC or Nlrp3-silenced BRAFV600E PTEN−/− melanomas (n=5). (B) qRT-PCR analysis of CXCR2-dependent chemokine expression in BRAFV600E PTEN−/− NTC and BRAFV600E PTEN−/− NLRP3KD melanomas (n=3). (C) Flow cytometric analysis of CD8+ T cells in resected BRAFV600E PTEN−/− NTC and BRAFV600E PTEN−/− NLRP3KD melanomas (n=5).
Figures 6F, 6G, 6H:
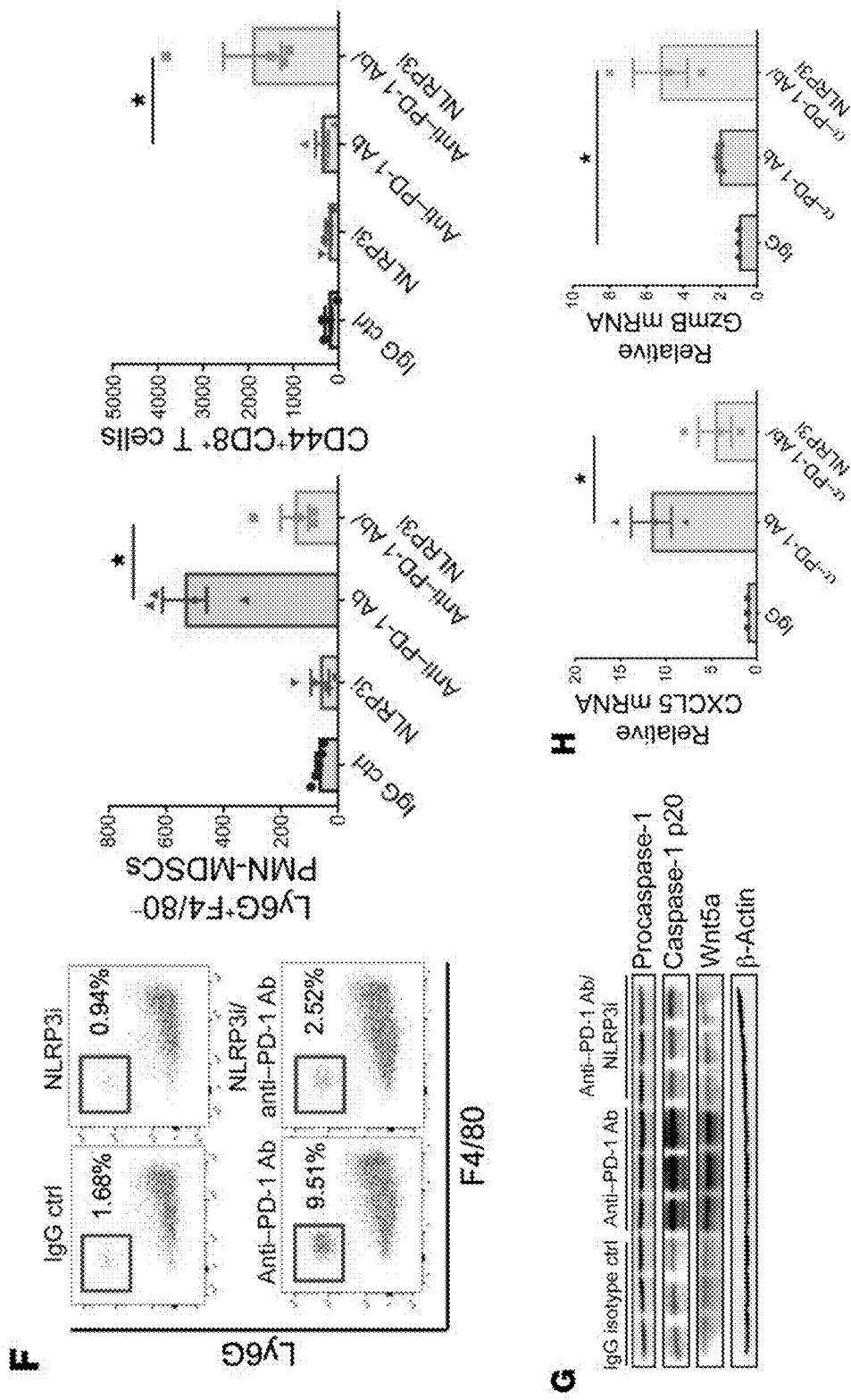
Figures 14A, 14B, 14C, 14D, 14E, 14F:
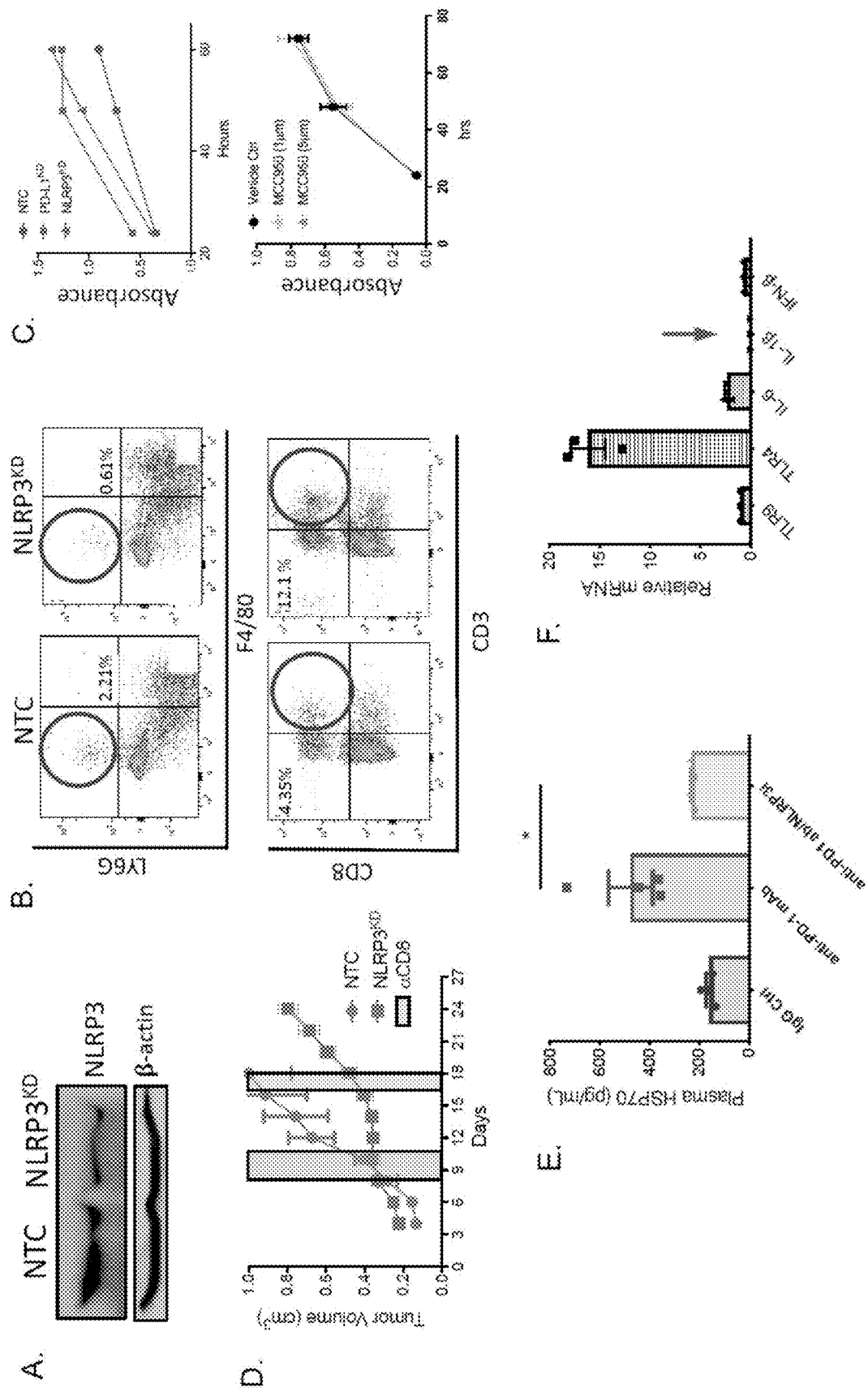
Figures 14G, 14H:
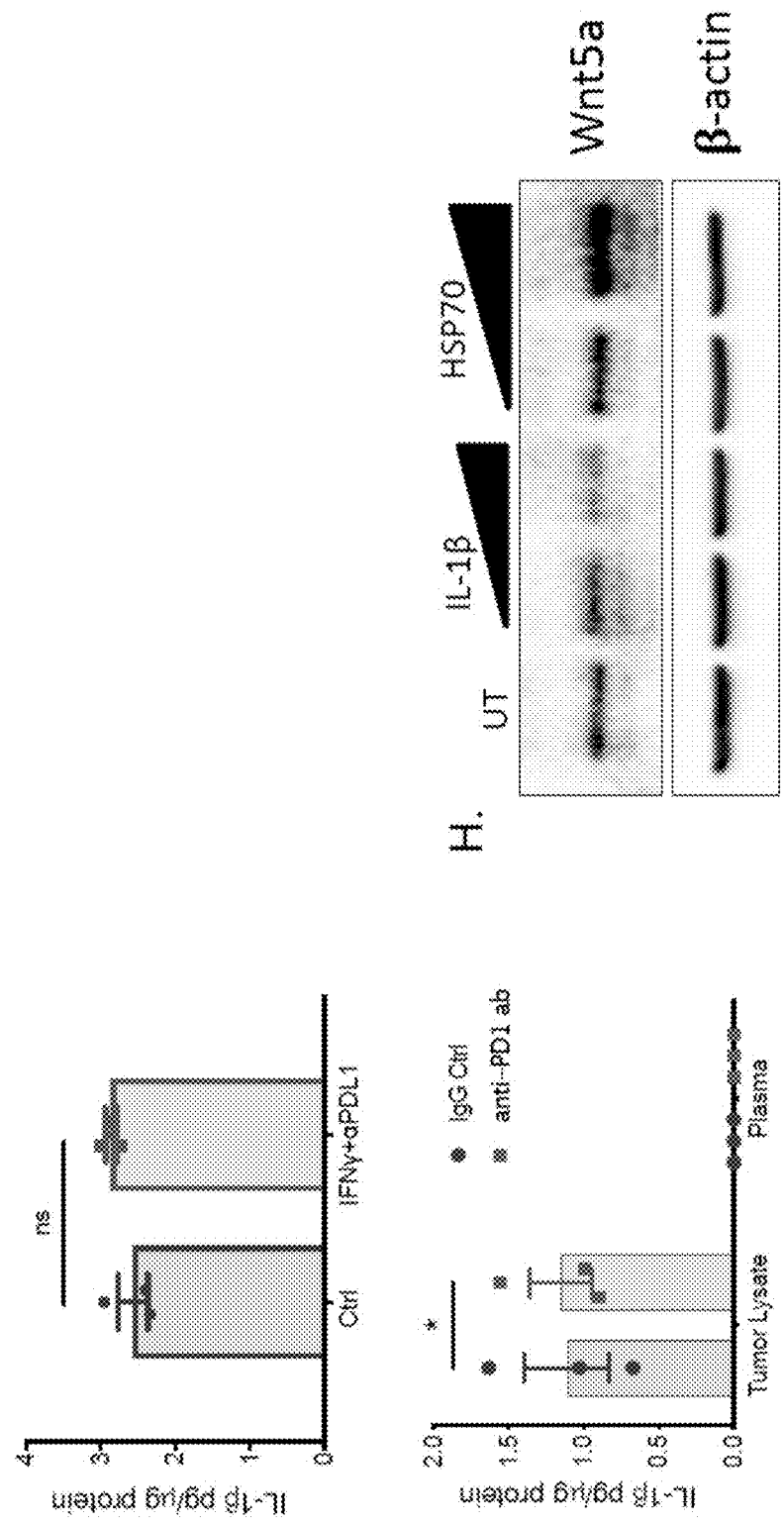

Given the central role of the NLRP3 inflammasome in mediating PMN-MDSC recruitment to the tumor bed in response to anti-PD-1 Ab therapy, we hypothesized that inhibiting NLRP3 activation would promote antitumor immunity and suppress tumor progression. Using a shRNA-expressing lentiviral vector, we silenced Nlrp3 in BRAFV600E PTEN−/− melanoma cells and transplanted this cell line into syngeneic hosts (FIG. 14A). After 20 days of tumor growth, Nlrp3-silenced BRAFV600E PTEN−/− melanomas were associated with reduced plasma HSP70 levels, decreased levels of CXCR2 ligand expression, and diminished PMN-MDSC infiltration relative to control BRAFV600E PTEN−/− melanomas (FIG. 6, A-C). Although Nlrp3 silencing did not influence tumor cell proliferation in vitro, it increased the levels of tumor-infiltrating CD8+ T cells and suppressed the growth of BRAFV600E PTEN−/− melanomas in vivo. (FIGS. 6, C and D, and FIGS. 14, B and C). NLRP3-dependent regulation of the antitumor immune response was further confirmed by additional in vivo tumor experiments, in which CD8+ T cell ablation reversed tumor growth suppression in Nlrp3-silenced BRAFV600E PTEN−/− melanomas (FIG. 14D).

We performed additional studies to determine whether systemic pharmacological inhibition of NLRP3 could also suppress tumor growth and augment anti-PD-1 Ab immunotherapy in the BRAFV600E PTEN−/− melanoma model.

Using the NLRP3 inhibitor MCC950, we also found that systemic NLRP3 inhibition diminished PMN-MDSC recruitment in response to anti-PD-1 Ab therapy, enhanced levels of tumor-infiltrating CD8+ T cells, and suppressed tumor progression in vivo beyond what was observed with anti-PD-1 Ab monotherapy (FIGS. 6, E and F) (37). Whole-tissue Western blot analysis, plasma ELISAs, and tumor qRT-PCR studies further showed that these effects correlated with suppressed caspase-1 cleavage, Wnt5a expression, Cxcl5 levels, and HSP70 release and enhanced expression of the cytolytic T cell marker Gzmb (FIGS. 6, G and H, and FIG. 14E). Notably, neither pharmacologic inhibition of NLRP3 nor genetic silencing of Nlrp3 had any impact on tumor cell proliferation in vitro (FIG. 14C). Altogether, these data are consistent with our previous studies supporting the critical role of the NLRP3 inflammasome in driving PMN-MDSC recruitment as an adaptive response to CD8+ T cell activation and suggest that NLRP3 is a viable pharmacologic target for enhancing the efficacy of anti-PD-1 Ab therapy.

PMN-MDSC Recruitment as a Mechanism of Adaptive Resistance to Anti-PD-1 Antibody Therapy in Human Melanoma.

Figures 7A, 7B, 7C, 7D:
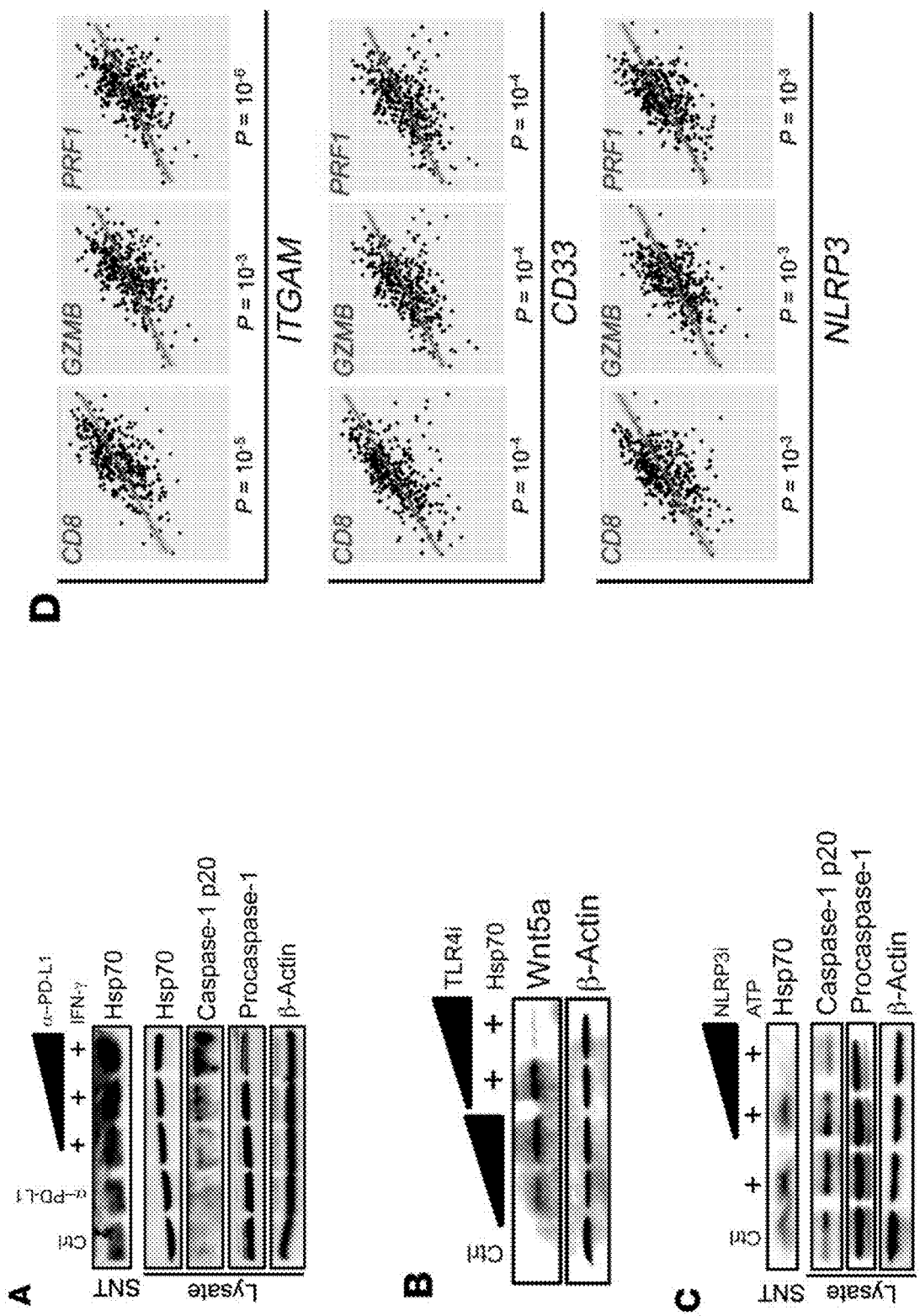
Figures 7E, 7F, 7G:
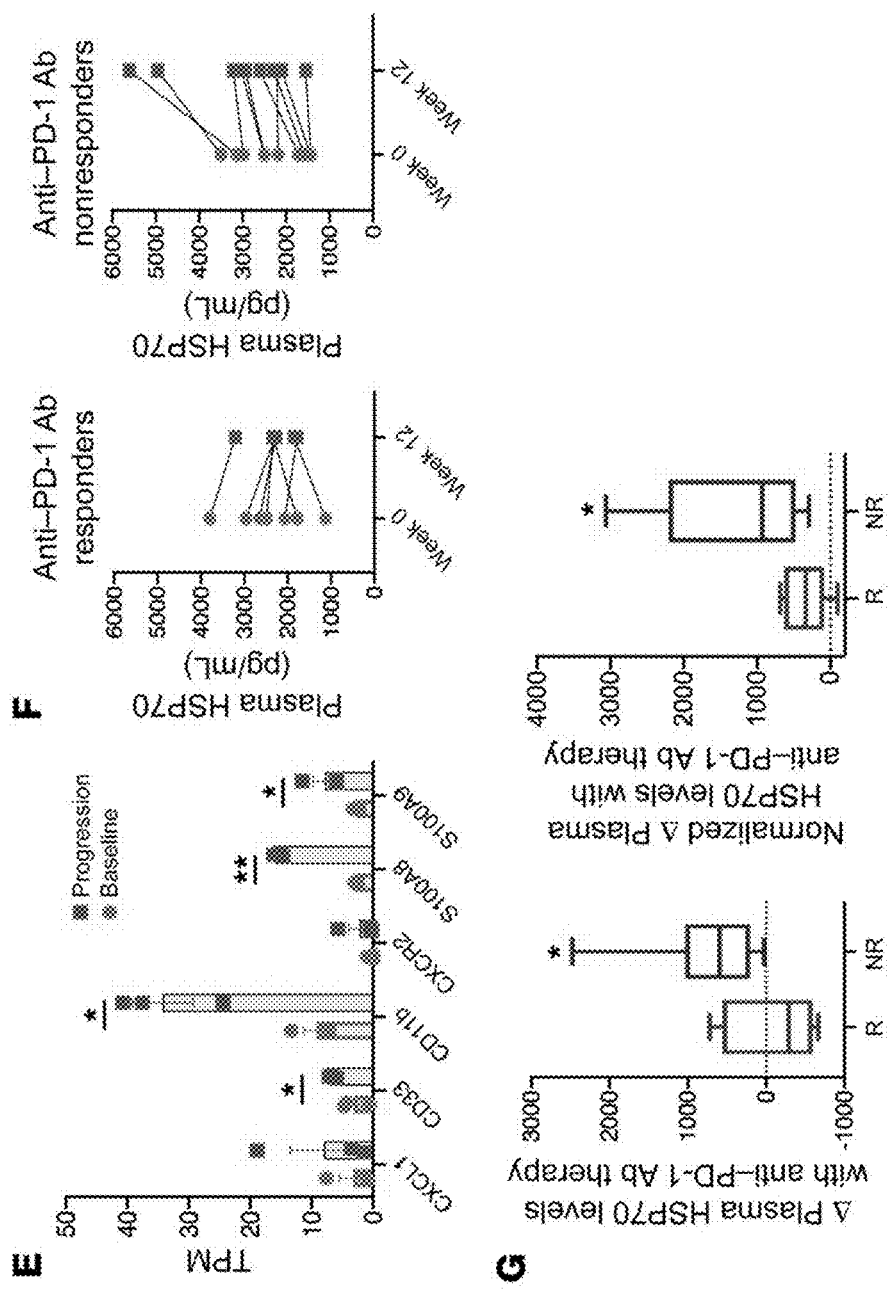

In order to determine whether PD-L1 can trigger NLRP3 activation and HSP70 release in human melanoma, we performed in vitro experiments using the WM266 human melanoma cell line. Similar to our previous observations, tumor PD-L1 cross-linking following IFN-γ stimulation induced caspase-1 cleavage and HSP70 release (FIG. 7A). Further studies using the WM266 human melanoma cell line also showed that HSP70 induced Wnt5a upregulation in a TLR4-dependent manner and that pharmacologic NLRP3 inhibition suppressed ATP-mediated HSP70 release (FIGS. 7, B and C). These data were consistent with a significant correlation between expression of the myeloid markers ITGAM and CD33 as well as NLRP3 and the cytolytic T cell markers CD8A, GZMB, and PRF in human metastatic melanoma specimens, based on RNA expression data in TCGA-SKCM database (FIG. 7D). These data are consistent with our previous observations in the autochthonous murine melanoma model and suggest that CD8+ T cell activation results in tumor release of HSP70, Wnt5a upregulation, and recruitment of infiltrating myeloid cells (FIG. 1A). To further study this mechanism, we harvested human melanoma tissue specimens at baseline and during disease progression following nivolumab anti-PD-1 Ab immunotherapy and performed RNASeq differential whole transcriptomic sequencing analysis. Consistent with our preclinical studies, these studies revealed elevated expression of several myeloid markers including CXCL1, CD33, ITGAM, CXCR2, S00A8, and S00A9 following disease progression through checkpoint inhibitor immunotherapy (FIG. 7E).

Our previous work showed that tumors release HSP70 in response to CD8+ T cell responses and that this increase in HSP70 levels can be measured in the plasma of mice undergoing anti-PD-1 Ab immunotherapy (FIG. 3C and FIG. 14E). On the basis of these data, we conducted a plasma-based ELISA to quantitate HSP70 levels at baseline and at week 12 of anti-PD-1 Ab immunotherapy in patients with advanced melanoma undergoing anti-PD-1 Ab immunotherapy. This study revealed that HSP70 levels increased in patients who progressed on anti-PD-1 Ab therapy, but these changes were seldom observed in responders (FIG. 7F). Indeed, mean changes in plasma HSP70 levels with anti-PD-1 Ab therapy were significantly greater in nonresponding melanoma patients relative to responders (FIG. 7G). This relationship was also observed after normalizing quantitative HSP70 levels to tumor burden based on CT imaging, indicating that this finding was not strictly due to disease progression. These observations suggest that the process leading to HSP70 release correlates with resistance to checkpoint inhibitor therapy, providing further support for the key role of the NLRP3 inflammasome in the evolution of adaptive resistance to anti-PD-1 Ab immunotherapy.

Discussion

Using several preclinical models in addition to clinical specimens, we have characterized a PD-L1-dependent, tumor-intrinsic signaling pathway that directly links CD8+ T cell activity with the recruitment of PMN-MDSCs to the tumor bed in response to anti-PD-1 Ab immunotherapy. We propose that this signaling cascade constitutes an adaptive resistance pathway that, when blocked, can enhance the efficacy of anti-PD-1 Ab checkpoint inhibitor immunotherapy. After recognizing a consistent increase in PMN-MDSCs in tumor tissues following anti-PD-1 Ab escape in several tumor models, we traced the underlying mechanism of this phenomenon to a process that involves PD-L1-dependent activation of the NLRP3 inflammasome in tumor tissues. Together, these data highlight several potential pharmacologic targets that may be capable of enhancing immunotherapy efficacy, as well as promising candidate biomarkers that may contribute to improved patient selection and management of patients with cancer undergoing immunotherapy.

Prior studies demonstrating that noncanonical Wnt ligands can induce the activation of YAP-dependent signaling pathways, coupled with data showing that YAP signaling can regulate the expression of several CXCR2-dependent chemokines, prompted us to explore a role for Wnt5a in mediating the observed influx of PMN-MDSCs in response to checkpoint inhibitor therapy (27, 28). These studies demonstrated that tumor Wnt5a expression was induced in response to anti-PD-1 Ab therapy and that the genetic silencing of tumor Wnt5a expression eliminated adaptive recruitment of PMN-MDSCs in response to checkpoint inhibitor immunotherapy. A recent RNA-Seq-based study found Wnt5a to be significantly upregulated in PD-1-refractory melanoma tissues, whereas other studies identified Wnt5a as a marker of dedifferentiation, disease aggressiveness, and therapeutic resistance (17, 18, 38, 39). However, a mechanistic description of how Wnt5a promotes immune tolerance and immunotherapy resistance remains incomplete. The present study indicates that autocrine Wnt5a signaling could promote PMN-MDSC recruitment to the tumor bed, which is consistent with our prior studies demonstrating a role for paracrine Wnt5a signaling in the induction of DC indoleamine 2,3-dioxgenase expression and enzymatic activity and the subsequent promotion of DC-mediated Treg differentiation (19, 40). Overall, these data provide further support for the idea that Wnt ligand-mediated signaling in the tumor microenvironment promotes immune evasion and that targeting Wnt ligand signaling is a promising option for modulating tumor immunity and responses to checkpoint inhibitor immunotherapy.

When evaluating the underlying mechanism driving Wnt5a upregulation in response to anti-PD-1 Ab therapy in these models, we noted evidence of a considerable level of HSP release by tumor cells, based on LC-MS/MS secretome analysis. Tumor release of HSP70 was further confirmed by Western blot analysis and ELISA in response to cytolytic CD8+ T cell activity in vitro and in vivo, respectively. This finding was of interest since previous studies have demonstrated that HSP70 can promote cancer progression and that TLRs both mediate HSP70 signaling and have been implicated in the regulation of Wnt5a expression in macrophages (20, 29, 41, 42). We subsequently demonstrated that HSP70 is capable of stimulating Wnt5a expression in various cell lines and that genetic silencing and pharmacologic inhibition of tumor TLR4 blocked tumor Wnt5a and CXCL5 expression, while also inhibiting PMN-MDSC recruitment to developing tumors. Notably, the release of HSP70 was not found to be due simply to a cell death-dependent mechanism, as dacarbazine chemotherapy readily induced tumor apoptosis in the BRAFV600E melanoma model but did not induce significant levels of HSP70 release. Although HSP70 has been identified within tumor-derived exosomes, prior studies have also suggested that soluble HSP70 may be released by tumor cells by an alternative, previously uncharacterized mechanism (43). Extracellular ATP has been implicated as a regulator of HSP70 release by tumor cells (32). Since ATP is a known modulator of the NLRP3 inflammasome, which in turn regulates the release of other inflammatory cytokines such as IL-1β and IL-18 that also lack leader peptide sequences, we initiated studies which confirmed that the NLRP3 inflammasome serves as an upstream regulator of HSP70 secretion by tumors (44). Indeed, these data demonstrate that both pharmacologic inhibition and genetic silencing of Nlrp3 effectively inhibited tumor release of HSP70 and ultimately eliminated the adaptive recruitment of PMNMDSCs in response to anti-PD-1 Ab therapy. It is important to note that we also conducted a series of experiments which showed no evidence that treatment with anti-PD-L1 Ab in vitro or anti-PD-1 Ab in vivo results in significant IL-1β expression or release in tumor cells or that IL-1β induces Wnt5a expression by tumor cells, as is observed with HSP70, thus suggesting that tumor-derived IL-1β does not contribute to MDSC recruitment in response to checkpoint inhibitor immunotherapy (FIG. 14, F-H) (45). This finding is also consistent with additional studies demonstrating that genetic knockout of HSP70 eliminated stimulation of Wnt5a in response to NLRP3 activation (FIG. 13B). Whether NLRP3-dependent IL-18 secretion contributes to the overall mechanism by promoting IFN-γ expression is unclear and is currently being explored.

Using in vitro coculture assays and in vivo ablation experiments, these studies identified CD8+ T cell activity as an important driver for this tumor-intrinsic signaling pathway. This finding further prompted experiments which showed that IFN-γ and its downstream modulation of PD-L1 were necessary for activation of the NLRP3 inflammasome. Although NF-κB-dependent priming signals are required for the induction of NLRP3 activation in certain cell types such as macrophages, it appears that this signal was not necessary in the tumor models used here (33). Whether IFN-γ stimulation also serves to facilitate NLRP3 priming by an alternative mechanism in tumor cells is currently being investigated. Interestingly, HSP70/TLR4 signaling, as described above, may also provide a positive feed-forward priming pathway capable of perpetuating NLRP3 activation in tumors (46). These studies reveal that NLRP3 inhibition phenocopied downstream TLR4 and CXCR2 inhibition, suppressing the recruitment of PMN-MDSCs as an adaptive resistance mechanism initiated by local CD8+ T cell activity. This finding is in line with a previous study showing that NLRP3 can mitigate against DC vaccine therapies by promoting the migration of MDSCs into tumors (47).

Given the role of PD-L1 in the induction of this pathway as well as reports describing downstream signaling effects of PD-L1, we also conducted studies to better understand the underlying mechanism of NLRP3 activation in tumor cells (48). The previously described role of PKR in the regulation of inflammasome activation and its modulation by STAT3 led to a series of experiments culminating in our finding that PD-L1 induced PKR-mediated NLRP3 activation by inhibiting STAT3 (34, 35). Interestingly, these findings were consistent with those of other investigators who recently reported that the cytoplasmic domain of PD-L1 negatively regulates STAT3 in tumor cells (23). However, to our knowledge, this study is the first to report a mechanistic link between tumor PD-L1 and activation of the NLRP3 inflammasome in response to checkpoint inhibitor immunotherapy.

The overall findings of this study support further interrogation of this pathway as a source of both pharmacologic targets to augment the efficacy of immunotherapy and biomarkers to predict clinical responses and outcomes following exposure to immunotherapy. It should be noted that the use of CXCR2 inhibitors as a strategy to enhance anti-PD-1 Ab immunotherapy is a concept that has been tested in preclinical tumor models and is currently being evaluated in early-phase clinical trials (Clinicaltrials.gov: NCT02583477, NCT03161431, NCT03473925) (8, 10). However, much like how PD-1/PD-L1 Ab antagonists offer a more tissue selective treatment approach over alternative immunotherapies, we conjecture that targeting the upstream NLRP3 inflammasome in this pathway will allow for more tumor-selective inhibition of CXCR2 chemokine-dependent recruitment of PMN-MDSCs, thus reducing the risk of systemic toxicity such as neutropenia. The NLRP3 target is also of particular interest in light of its described role in several inflammatory and autoimmune conditions, suggesting that the PD-L1/NLRP3 signaling axis may play an important role in driving some immune-related adverse events (irAEs) associated with checkpoint inhibitor immunotherapy (49, 50). These findings have prompted further study by our group to determine whether NLRP3 inhibition may mitigate against anti-PD-1 Ab-induced irAEs and whether any genetic alterations of NLRP3 or its regulators may predict for the development of specific irAEs. Finally, it is tempting to speculate that there may be a potential relationship between this IFN-γ-dependent resistance pathway and the role of chronic IFN signaling in immunotherapy resistance described in a recent report (51).

In summary, we present evidence of an adaptive resistance signaling pathway that is inexorably linked to tumor PD-L1 and drives the recruitment of PMN-MDSCs to the tumor bed in response to anti-PD-1 checkpoint inhibitor therapy. This process extinguishes local cytotoxic antitumor T cell activity and serves as a rheostat for modulating effector T cell responses, thus making this signaling axis a promising target for immunotherapeutic intervention.

Methods for Example 1

Clinical Samples

All plasma samples were collected from 17 advanced melanoma patients undergoing anti-PD-1 ab immunotherapy at week 0 and week 12 on an ongoing tissue acquisition protocol investigating checkpoint inhibitor resistance at Duke Cancer Institute (NCT02694965). Three paired tumor specimens obtained at week 0 and at the time of disease progression while undergoing anti-PD-1 ab immunotherapy were collected at Vanderbilt University Medical Center (Institutional Protocol #: 100178). Treatment responses were evaluated based on RECIST (Response Evaluation Criteria in Solid Tumors v1.1).

In Vivo Animal Studies

C57BL/6J (C57, H-$2^b$) (Stock number 000664), B6.CgBraf$^{tm1Mmcm}$Pten$^{tm1Hwu}$Tg(Tyr-cre/ERT2)13Bos/BosJ (Braf$^{V600E}$ Pten$^{-/-}$, H-$2^b$) (Stock number 012328) and C57BL/6Tg(TcraTcrb) 1100Mjb/J (OT-1, H-$2^b$) (Stock number 003831) mice were obtained from Jackson Labs. All experimental groups included randomly chosen littermates of both sexes, ages 6-8 weeks, and of the same strain. Experiments were performed based on a protocol approved by the Institutional Animal Care and Use Committee at Duke University Medical Center.

Cell Lines and Culture Conditions.

Braf$^{V600E}$Pten$^{-/-}$ (male, BPD6 (40)), Braf$^{V600E}$Pten$^{-/-}$-Wnt5a$^{KD}$ (40), Braf$^{V600E}$Pten$^{-/-}$-CXCL5$^{KD}$, Braf$^{V600E}$Pten$^{-/-}$-PDL1$^{KD}$, Braf$^{V600E}$Pten$^{-/-}$-NLRP3$^{KD}$, OVA-expressing Braf$^{V600E}$Pten$^{-/-}$, BRAF$^{V600E}$PTEN$^{-/-}$-STAT3$^{CA}$, and Braf$^{V600E}$Pten$^{-/-}$-NTC (40) cell lines were generated using shRNA-expressing lentiviral vectors and cultured as previously described (40): shNLRP3 (Sigma, SHCLN-NM_145827), shPDL1 (Sigma, SHCLND-NM_021893), shWnt5a (Sigma, SHCLND-NM_009524), shTLR4 (Sigma, SHCLNG-NM_025817, and pLKO.1-puro empty vector control (NTC) (Sigma, SHC001). Stable cell lines were selected by puromycin resistance (Sigma-Aldrich, P8833). Murine Lewis Lung Carcinoma (LLC) cell line is from ATCC (1704526). All cell lines were tested *Mycoplasma*-free by Duke University Cell Culture Facility shared services. All Braf$^{V600E}$Pten$^{-/-}$ cell lines and the LLC cell line were maintained at 37° C. in DMEM (Invitrogen) with 2 mM L-glutamine, supplemented with 10% fetal bovine serum, 100 units/ml penicillin. Depending on the experiment, cell lines were treated with Wnt5a (100-200 ng/ml, R&D Systems/Bio-techne, 645-WN-010), IFNγ (100 ng/ml, BioAbChem, 42-IFNg), anti-PD-L1 ab (1-2 µg/ml), Hsp70 (1 µM-10 µM, Enzo, ADI-ESP-502-D), Hsp70 inhibitor (ThermoFisher, VER155008), CLI-095 TLR4 inhibitor (3 µM-10 µM, Invivogen, tlrl-cli95), TLR2-IN-C29 TLR2 inhibitor (1 µM-10 µM, Glixx, GLXC-06203), MPLA TLR4 agonist (10 µM, Enzo, ALX-581-205-C100), LPS (Lipopolysaccharide) (10 ng, Sigma-Aldrich, L4391-1MG), ATP (1 mM-5 mM, Invivogen, tlrl-atpl), MCC950 NLRP3 inhibitor (2.5 µM-10 µM, Invivogen, inh-mcc), XAV939 β-catenin inhibitor (0.5-1.0 µM, Sigma-Aldrich, X3004-5MG), 2-Aminopurine PKR inhibitor (1 mM-5 mM, Invivogen, tlrl-apr), Verteporfin YAP inhibitor (0.1 µM-1 µM, R&D Systems/Bio-techne, 530510) or vehicle control either for 24 or 48 hrs prior to in vitro and in vivo experiments. Control siRNA (Santa Cruz, sc-37007). TLR4 siRNA (SantaCruz, sc-40261).

Autochthonous Tumor Studies.

B6.Cg-Braf$^{tm1Mmcm}$Pten$^{tm1Hwu}$ Tg(Tyr-cre/ERT2 H-$2^b$) 13Bos/BosJ transgenic mice were subdermally injected with 4-Hydroxytomoxifen (4-HT) (Sigma, H6278-50MG CCF, 38.75 µg/mouse) to induce primary melanoma development at the base of the tail. Mice were randomly assigned to treatment cohorts once tumor volumes reached 64 mm$^3$ (19, 30, 50). Depending on the experiment, mice were treated with the following agents: CXCR2 inhibitor (AZD5069, AstraZeneca) at 100 mg/kg per os (po) twice daily, NLRP3 inhibitor (MCC950) 10 mg/kg i.p every other day, anti-PD1 ab (BioXCell) or rat IgG2a isotype control (BioXCell) at 200 µg by i.p. injection every 3 days, Dacarbazine (50 mg/kg or 75 mg/kg, Sigma-Aldrich, D2390) by i.p. injection once every other day. Melanoma growth was monitored by orthogonal caliper measurements every 3 days.

Syngeneic Transplant Tumor Studies.

Braf$^{V600E}$Pten$^{-/-}$, Braf$^{V600E}$Pten$^{-/-}$-NTC, Braf$^{V600E}$Pten$^{-/-}$-Wnt5a$^{KD}$, Braf$^{V600E}$Pten$^{-/-}$-CXCL5$^{KD}$, Braf$^{V600E}$Pten$^{-/-}$-PDL1$^{KD}$, and Braf$^{V600E}$Pten$^{-/-}$-NLRP3$^{KD}$ cell lines (0.5×10$^5$-1×10$^5$ cells) were implanted by subcutaneous injection into the base of the tail of syngeneic C57BL/6 mice. Tumor growth was monitored by caliper measurement every 3 days and treatment was initiated when tumor volumes reached 64 mm$^3$. Tumor volume was calculated according to the formula: cm$^3$=[(length (cm)×(width (cm))$^2$]/2.

Murine Cell Isolation.

Tumors were resected and mechanically disaggregated by a gentleMACS dissociator (Miltenyi), filtered through 70-µm filters and digested with RPMI containing collagenase IV (1 mg/mL, Sigma-Aldrich), hyaluronidase (0.1 mg/mL, Sigma-Aldrich), and deoxyribonuclease (20 U/mL, Sigma-Aldrich) on a shaker at 250 rpm at 37° C. for 1 hour (23). Resected splenic and lymph node tissues were mechanically disaggregated using 1 cc syringe plunger and 40 µm filters followed by treatment with RBC lysis buffer (Sigma-Aldrich).

In Vivo CD8 Depletion

Hybridoma clone 53-6.7 was expanded at the Duke Cell Culture Facility in hollow fiber cartridges; 10 ml of serum free supernatant was harvested every 2 days. Anti-mouse CD8 antibody was purified using a Pierce Gentle Ag/Ab Binding and Elution Buffer Kit (ThermoFisher, 21030) according to the manufacturer's protocol (ThermoFisher). Antibody concentration was determined by BCA protein assay. Anti-CD8 ab or IgG isotype control ab was delivered daily for the first three days then every 7 days thereafter by intraperitoneal injection (500 µg/mouse/dose). CD8 depletion was verified by splenocyte flow cytometry analysis.

In Vitro Tumor Killing Assays

OT-1 CD8 cell activation was performed by incubating isolated splenocytes of OT-1 transgenic mice with IL-2 (100 U/ml) and SIINFEKL peptide (1 µg/ml, New England Peptide, BP10-915) for 3 days followed by magnetic bead CD8 purification according to the manufacturer's instructions (Miltenyi biotec, 130-104-075). Activated OT-1 CD8 cells were incubated with Braf$^{V600E}$Pten$^{-/-}$-OVA cells and treated with anti-PD1 ab (1 µg/ml) for 72 hrs at a tumor cell:CD8$^+$ T cell ratio of 1:5. In separate experiments, Braf$^{V600E}$Pten$^{-/-}$ cells were treated with increasing concentrations of Dacarbazine (10 µmol-400 µmol).

IHC and Immunofluorescence Analysis

Paraffin-embedded tissues were processed and stained following standard protocols and imaged with a Zeiss CLSM 700 confocal microscope. The following antibodies were used in immunohistochemistry and immunofluorescence experiments: anti-Wnt5a (1 µg/ml), anti-Ly6G (0.5 µg/ml), anti-CD8a (0.5 µg/ml) and anti-CXCL5 (1 µg/ml). Tissue was permeabilized by incubation in 0.4% Triton-X in TBS for 20 min. Goat anti-rabbit conjugated to Alexa Fluor 564 and goat anti-mouse Alexa 488 were used as secondary antibodies for the appropriate primary antibody. For immunohistochemistry, anti-rat polymers were used as secondary antibodies and Warp Red chromogen detection system (BioCare, WR806S) was used for antigen visualization.

Flow Cytometry Analysis

One million cells were stained with 1 µg per million cells of each fluorochrome conjugated antibodies or commercially available dyes according to the standard protocols and analyzed using a FACSCanto II or LSRII (Becton Dickinson). Cells were stained with Fc receptor blocking antibodies followed by a live/dead discriminator (CellTrace Violet, ThermoFisher, C34571), then by conjugated antibodies for 30 min at 4° C. Cell number was calculated by hemocytometer. Flow cytometry data was analyzed using Flowjo software v10.3.

Immunoblot, Immunoprecipitation, and ASC Polymerizations Studies

Tumor tissue or cells were homogenized in NP40 lysis buffer (Sigma-Aldrich) supplemented with complete protease inhibitor and phosphatase inhibitor (Roche). Cells were lysed in Laemmli sample buffer after treatment and subjected to SDS-polyacrylamide gel electrophoresis. After transferring onto PVDF membranes (Bio-Rad), monoclonal and polyclonal primary antibodies and appropriate HRP-conjugated secondary antibodies were utilized for blotting. For the immunoprecipitation assays, cells were lysed with TBS buffer (50 mM Tris-HCl (pH 7.4), 150 mM NaCl) containing 0.5% Triton X-100, EDTA-free protease inhibitor cocktail and phosphatase inhibitor cocktail, precleared with protein A/G beads, and then incubated with 1 µg of appropriate antibodies or isotype control IgG on a rotator overnight at 4° C. then incubated with protein A/G-agarose at 4° C. for 1 hour. After 5 washes with TBS buffer, immunoprecipitated complexes were eluted in sample buffer by boiling and subjected to immunoblot analysis. Immunoblots were visualized by chemiluminescence substrate (ThermoFisher) and imaged by a ChemiDoc XRSplus system (BioRad). For the ASC polymerization assay, cells were lysed with TBS buffer containing 0.5% Triton X-100, EDTA-free protease inhibitor cocktail and phosphatase inhibitor cocktail. The lysates were centrifuged at 4,000 g at 4° C. for 15 min. For the detection of ASC oligomerization, the Triton-insoluble pellets were washed twice with TBS buffer and then resuspended in 500 µl TBS buffer. The resuspended pellets were crosslinked for 30 min at room temperature with 2 mM Disuccinimidyl suberate (DSS) (Thermo Fisher Scientific, 21655) and then centrifuged for 15 min at 6,000 g. The pellets were dissolved in SDS sample buffer.

Antibodies

The following Abs were used: Anti-β-actin mouse monoclonal (Santa Cruz Biotechnology, sc-47778). Anti-NLRP3, Rabbit monoclonal (Cell Signaling, 15101S). Anti-ASC mouse monoclonal (Santa Cruz Biotechnology, sc-514414). Anti-Caspase-1-p20, mouse monoclonal (Adipogen, AG-20B-0042-C100). Anti-Caspase-3, rabbit polyclonal (Cell Signaling, 9662S). Anti-HSP70, mouse monoclonal (Santa Cruz Biotechnology, sc-66048). Anti-CXCL5, goat polyclonal (R&D systems, AF433). Anti-CXCL5, rabbit polyclonal (Lsbio, LS-c293780). Anti-YAP/TAZ, rabbit monoclonal (Cell Signaling, 8418S). Anti-Wnt5a, mouse monoclonal (Santa Cruz Biotechnology, sc-365370). Anti-GAPDH, mouse monoclonal (Santa Cruz Biotechnology, sc-32233). CD8a, rabbit monoclonal (Cell Signaling, 989415). InVivoMAB Anti-human PD-L1 (BioXCell, BE0285). InVivoMAB Anti-mouse PD-L1 (BioXCell, BE0101). InVivoMAB Anti-mouse PD-1 (BioXCell, BE0146). InVivoMAb rat IgG2a isotype control, clone: 2A3 (BioXCell, BE0089). Anti-mouse CD8 antibody from hybridoma, (Duke Cell Culture Facility, clone 53.6.7). Anti-ovalbumin (Santa Cruz, sc-65984). Anti-IL-1-β, mouse monoclonal (Cell signaling, 12242). Anti-LY6G-Gr1 (Abcam, ab25377). Goat Anti-Rat IgG H&L (EMD Millipore, AP136P). IFN-γ antibody, mouse monoclonal (Novus bio, MAB4851-SP). Anti-STAT3 antibody, mouse monoclonal (Santa Cruz Biotechnology, sc-8019). Anti-phospho-STAT3 antibody, mouse monoclonal (Cell Signaling, 9131). Anti-PKR antibody, mouse monoclonal (Santa Cruz Biotechnology, sc-6282). Anti-PKR (phosphor-T446) antibody, rabbit monoclonal (Abcam, ab32036). Anti-Vinculin antibody, rabbit monoclonal (Invitrogen/Pierce, 700062). Anti-Laminin b1 antibody, mouse monoclonal (Santa Cruz Biotechnology, Sc-374015). Anti-Mouse CD11c, FITC conjugated, clone: HL3 (BD Pharmingen, 553801). Anti-Mouse CD11b, PE conjugated, clone: MIHS (BD Pharmingen, 558091). Anti-Mouse CD8a, BV510 conjugated, clone: 53-6.7 (BD Pharmingen, 563068). Anti-Mouse CD3e, PerCP-Cy5.5 conjugated, clone: 145-2C11 (BD Pharmingen, 551163). Anti-Mouse Ly6G-GR1, FITC conjugated, clone: RB6-8C5 (BD Pharmingen, 5532127. Anti-mouse F4/80 Antibody, APC conjugated, clone: BM8 (BD Pharmingen, 560408). Anti-Mouse CD45, PerCP-Cy5.5 conjugated, clone: 145-2C11 (BD Pharmingen, 551163). Anti-Mouse Ly6C, PE-Cy7 conjugated, clone: AL-21 (BD Pharmingen, 560593). Anti-human HLA-DR, PerCP-Cy5.5 conjugated, clone: tu36 (BioLegend, 361607). Anti-human CD15, PE Cy7 conjugated, clone: h198 (BD Pharmingen, 560827). Anti-human CD33, Bv510 conjugated, clone: wm53 (BD Pharmingen, 563257). Anti-human CD11b, PE conjugated (BD Pharmingen, 557321). Anti-human CD14, FITC conjugated (BD Pharmingen, 557153).

RNA Isolation and RT-qPCR Analysis

Total RNA was isolated by RNeasy Plus Mini Kit (Qiagen, 74134). RNA (1000 ng) was used in cDNA Synthesis (iScript Reverse Transcription Supermix, BioRad, 1708841). Real-time PCR was performed using an ABI7500 Real-Time PCR system (Life Technologies) and the primers listed in Table 1. Data analysis utilized the PrimePCR Analysis Software (BioRad). Conventional qPCR was performed using validated primers and SsoAdvanced Universal SYBR Green Super mix (BioRad, 1725271) or SsoAdvance Universal Probes Supermix (BioRad, 1725281). All data were normalized to Actb expression, and relative gene expression was quantitated based on the 2_DDCt method.

TABLE 1

Primer Table for Described qrt-PCR Experiments.

| Name | Forward Primer: | Reverse Primer: |
|---|---|---|
| mACTB | GGCTGTATTCCCCTCCATCG (SEQ ID NO: 1) | CCAGTTGGTAACAATGCCA TGT (SEQ ID NO: 2) |
| mAIM2 | ACAAAGTGCGAGGAAGGAGA (SEQ ID NO: 3) | TTTGGCTTTGCAGCCTTAAT (SEQ ID NO: 4) |
| mArg | AACACTCCCCTGACAACCAG (SEQ ID NO: 5) | CCAGCAGGTAGCTGAAGGTC (SEQ ID NO: 6) |
| mCCR2 | TTTGTTTTTGCAGATGAT TCAA(SEQ ID NO: 7) | TGCCATCATAAAGGAGCCA (SEQ ID NO: 8) |
| mCXCL1 | TGAGCTGCGCTGTCAGTG CCT (SEQ ID NO: 9) | AGAAGCCGACGTTCACC CAGA (SEQ ID NO: 10) |
| mCXCL2 | GAGCTTGAGTGTGACGCCCC CAGG (SEQ ID NO: 11) | GTTAGCCTTGCCTTTGTTCA GTATC (SEQ ID NO: 12) |
| mCXCL5 | GCATTTCTGTTGCTGTTCAC GCTG (SEQ ID NO: 13) | CCTCCTTCTGGTTTTTCAGT TTAGC (SEQ ID NO: 14) |
| mCXCR2 | AGCAAACACCTCTACTACCCT CTA (SEQ ID NO: 15) | GGGCTGCATCAATTCAAA TACCA (SEQ ID NO: 16) |
| mGAPDH | GTCTACATGTTCCAGTATGA CTCC (SEQ ID NO: 17) | AGTGAGTTGTCATATTTCTC GTGGT (SEQ ID NO: 18) |
| mIDO | CAGGCCAGAGCAGCATCTTC (SEQ ID NO: 19) | GCCAGCCTCGTGTTTTAT TCC (SEQ ID NO: 20) |
| mIL-10 | GACCAGCTGGACAACATAC (SEQ ID NO: 21) | GACCAGCTGGACAACATAC (SEQ ID NO: 22) |

TABLE 1-continued

Primer Table for Described qrt-PCR Experiments.

| Name | Forward Primer: | Reverse Primer: |
|---|---|---|
| mNLRC4 | CTACATTGATGCTGCCTTGG (SEQ ID NO: 23) | ATCCGTCACTGCTCACACAG (SEQ ID NO: 24) |
| mNLRP1 | CACTGCCCAAGATTGCTACA (SEQ ID NO: 25) | CTTCACTCAGCACCAGACCA (SEQ ID NO: 26) |
| mNLRP3 | GTGGTGACCCTCTGTGAGGT (SEQ ID NO: 27) | TCTTCCTGGAGCGCTTCTAA (SEQ ID NO: 28) |
| mS100a9 | ATACTCTAGGAAGGAAGGACACC (SEQ ID NO: 29) | TCCATGATGTCATTTATGAGGGC (SEQ ID NO: 30) |
| mTLR1 | CAATGTGGAAACAACGTGGA (SEQ ID NO: 31) | TGTAACTTTGGGGGAAGCTG (SEQ ID NO: 32) |
| mTLR2 | AAGAGGAAGCCCAAGAAAGC (SEQ ID NO: 33) | CGATGGAATCGATGATGTTG (SEQ ID NO: 34) |
| mTLR3 | CACAGGCTGAGCAGTTTGAA (SEQ ID NO: 35) | TTTCGGCTTCTTTTGATGCT (SEQ ID NO: 36) |
| mTLR4 | GCCTCTTCTCATTCCTGCTTG (SEQ ID NO: 37) | CTGATGAGAGGGAGGCCATT (SEQ ID NO: 38) |
| mTLR5 | AAGTTCCGGGGAATCTGTTT (SEQ ID NO: 39) | GCATAGCCTGAGCCTGTTTC (SEQ ID NO: 40) |
| mTLR6 | TTCCCAATACCACCGTTCTC (SEQ ID NO: 41) | CTATGTGCTGGAGGGTCACA (SEQ ID NO: 42) |
| mTLR7 | AATCCACAGGCTCACCCATA (SEQ ID NO: 43) | CAGGTACCAAGGGATGTCCT (SEQ ID NO: 44) |
| mTLR8 | GACATGGCCCCTAATTTCCT (SEQ ID NO: 45) | GACCCAGAAGTCCTCATGGA (SEQ ID NO: 46) |
| mTLR9 | ACTGAGCACCCTGCTTCTA (SEQ ID NO: 47) | AGATTAGTCAGCGGCAGGAA (SEQ ID NO: 48) |
| mIL-1β | ATGGCAACTGTTCCTGAACTCAACT (SEQ ID NO: 49) | CAGGACAGGTATAGATTCTTTCCTTT (SEQ ID NO: 50) |
| mIL-18 | GACTCTTGCGTCAACTTCAAGG (SEQ ID NO: 51) | CAGGCTGTCTTTTGTCAACGA (SEQ ID NO: 52) |
| mTNF-α | GCCTCTTCTCATTCCTGCTTG (SEQ ID NO: 53) | CTGATGAGAGGGAGGCCATT (SEQ ID NO: 54) |
| mTGF-β | GCAACAACGCCATCTATGAG (SEQ ID NO: 55) | ATCTTTGCTGTCACAAGAGC (SEQ ID NO: 56) | m, murine.

RNA-seq Assays

RNA-seq was performed by Duke Sequencing and Genomic Technologies Shared Resources. A complementary DNA library was prepared via oligo-dT-directed reverse transcription (Ambion) and subjected to deep sequencing on IlluminaHiSeq4000 (50-bp single-read sequencing; Anti-PD-1 resistance Study RNA-seq, accession number: SAMN09878780). RNA-seq data generated here and publicly available RNA-seq data were processed by Duke Center for Genomic and Computational Biology using the TrimGaloretoolkit that uses Cutadapt to trim low-quality bases and Illumina sequencing adapters from the 3' end of the reads. Only reads that were of 20 nucleotides (nt) or longer after trimming were kept for further analysis. Reads were mapped to the GRCm38v68 version of the mouse genome and transcriptome using the STAR RNA-seq alignment tool. Reads were kept for subsequent analysis, if they mapped to a single genomic location. Gene counts were compiled using the HTSeq tool. Only genes that had at least 10 reads in any given library were used in subsequent analysis. Normalization and differential expression were carried out using the DESeq2 Bioconductor package with the R statistical programming environment. The false discovery rate was calculated to control for multiple hypothesis testing. Gene set enrichment analysis was performed to identify differentially regulated pathways and gene ontology terms for each of the comparisons performed. Human melanoma tissues obtained from Vanderbilt University (IRB: 10078).

ELISA

Levels of CXCL5 and HSP70 (R&D Systems, DYC1663-2) in mouse plasma were evaluated using ELISA kit as per manufacturers' instructions (R&D Systems, Inc.). IL-1β (BioLegend, 432601) level in cell lysate, tumor lysate, and supernatant were measured based on ELISA kit according to manufacturers' instructions (Biolegend).

Human Plasma ELISA

Human plasma HSP70 concentrations were measured using the human DuoSet assay (R&D Systems, Inc., Catalog number DY1663, MN, USA) according to manufacturer's protocol. Human melanoma plasma samples obtained from Duke Cancer Institute (IRB: Pro00059349, Clinical trial number: NCT02694965).

Secretome Assays

Single cell suspensions were prepared by enzymatic and mechanical digestion. $2 \times 10^6$ cells were plated in 2 ml of 1% dialyzed FBS containing Light or heavy amino acids without L-methionine in 6 well plates, then incubated in $CO_2$ for 30 min. L-methionine or azidohomoalanine (AHA), an azide-bearing analogue of methionine was added to the plates and incubated in 5% $CO_2$ at 37° C. overnight. Culture supernatants were collected for secretome assay. Cell supernatants were enriched for AHA labeled proteins by incubating with DBCO-agarose overnight. Resins were washed, followed by reduction and alkylation of cys residues, and peptides were recovered after overnight digestion with trypsin. Samples were analyzed by quantitative one-dimensional liquid chromatography, tandem mass spectrometry. Using Proteome Discoverer 2.3, the data was searched against SwissPro Mouse database with semitrypsin specificity, fixed modification on Cys, and variable modifications on Met (oxidation), Gln/Asn (deamidation), Pro (hydroxylation) and Arg/Lys (15N-13C).

TCGA Data Analysis

TCGA skin cancer melanoma (TCGASKCM) annotated RNA expression files were extracted from the GDC portal (https://portal.gdc.cancer.gov/) for 376 cases of metastatic melanoma. Data preprocessing was performed using HTSeq counts from TCGA, and raw counts were normalized using the relative log expression method implanted in R and its extension package DESeq2. Coexpression of genes of interest were tested using the $\chi^2$ statistic of sample quantile-based contingency (SQUAC) table, and scatter plots were generated using normalized counts and Bonferroni's corrections on the group P values to account for multiple testing.

Statistics

GraphPad Prism 8 for Windows (GraphPad Software) was used for all statistical analyses. An unpaired, 2-tailed Student's t test was used to compare mean differences between the control and treatment groups. Univariate 1-way ANOVA followed by Sidak's post hoc multiple comparisons test was performed to analyze data containing 3 or more groups. Data correlation analyses were conducted using either Kendall Tau or Spearman calculations. A P value of less than 0.05 was considered significant. All quantitative data are presented as the mean SEM.

Study Approval

Mouse tumor experiments were performed according to a protocol approved by the IACUC of Duke University Medical Center. All patients provided written informed consent under approval from the IRBs of Duke University (NCT02694965) and Vanderbilt University Medical Center (protocol 100178). Human melanoma tissues were obtained from Vanderbilt University with IRB approval (protocol 100178). Human melanoma plasma samples were obtained from the Duke Cancer Institute with IRB approval (protocol Pro00059349, Clinicaltrials.gov: NCT02694965).

REFERENCES FOR EXAMPLE 1

1. Zhao X, and Subramanian S. Intrinsic Resistance of Solid Tumors to Immune Checkpoint Blockade Therapy. *Cancer research.* 2017; 77(4):817-22.
2. Pitt J M, Vetizou M, Daillere R, Roberti M P, Yamazaki T, Routy B, et al. Resistance Mechanisms to Immune-Checkpoint Blockade in Cancer: Tumor-Intrinsic and -Extrinsic Factors. *Immunity.* 2016; 44(6):1255-69.
3. O'Donnell J S, Long G V, Scolyer R A, Teng M W, and Smyth M J. Resistance to PD1/PDL1 checkpoint inhibition. *Cancer Treat Rev.* 2017; 52:71-81.
4. Marigo I, Dolcetti L, Serafini P, Zanovello P, and Bronte V. Tumor-induced tolerance and immune suppression by myeloid derived suppressor cells. *Immunological reviews.* 2008; 222:162-79.
5. Marvel D, and Gabrilovich D I. Myeloid-derived suppressor cells in the tumor microenvironment: expect the unexpected. *J Clin Invest.* 2015; 125(9):3356-64.
6. Sade-Feldman M, Kanterman J, Klieger Y, Ish-Shalom E, Olga M, Saragovi A, et al. Clinical Significance of Circulating CD33+CD11b+HLA-DR-Myeloid Cells in Patients with Stage IV Melanoma Treated with Ipilimumab. *Clin Cancer Res.* 2016; 22(23):5661-72.
7. Weber J, Gibney G, Kudchadkar R, Yu B, Cheng P, Martinez A J, et al. Phase I/II Study of Metastatic Melanoma Patients Treated with Nivolumab Who Had Progressed after Ipilimumab. *Cancer immunology research.* 2016; 4(4):345-53.
8. Highfill S L, Cui Y, Giles A J, Smith J P, Zhang H, Morse E, et al. Disruption of CXCR2-mediated MDSC tumor trafficking enhances anti-PD1 efficacy. *Sci Transl Med.* 2014; 6(237):237ra67.
9. Chao T, Furth E E, and Vonderheide R H. CXCR2-Dependent Accumulation of Tumor-Associated Neutrophils Regulates T-cell Immunity in Pancreatic Ductal Adenocarcinoma. *Cancer Immunol Res.* 2016.
10. Steele C W, Karim S A, Leach J D, Bailey P, Upstill-Goddard R, Rishi L, et al. CXCR2 Inhibition Profoundly Suppresses Metastases and Augments Immunotherapy in Pancreatic Ductal Adenocarcinoma. *Cancer Cell.* 2016; 29(6):832-45.
11. Sharma P, Hu-Lieskovan S, Wargo J A, and Ribas A. Primary, Adaptive, and Acquired Resistance to Cancer Immunotherapy. *Cell.* 2017; 168(4):707-23.
12. Neubert N J, Schmittnaegel M, Bordry N, Nassiri S, Wald N, Martignier C, et al. T cell-induced CSF1 promotes melanoma resistance to PD1 blockade. *Science translational medicine.* 2018; 10(436).
13. Chen L, Diao L, Yang Y, Yi X, Rodriguez B L, Li Y, et al. CD38-Mediated Immunosuppression as a Mechanism of Tumor Cell Escape from PD-1/PD-L1 Blockade. *Cancer discovery.* 2018; 8(9):1156-75.
14. Munn D H, and Mellor A L. Indoleamine 2,3-dioxygenase and tumor-induced tolerance. *J Clin Invest.* 2007; 117(5):1147-54.
15. Spranger S, Spaapen R M, Zha Y, Williams J, Meng Y, Ha T T, et al. Up-regulation of PD-L1, IDO, and T(regs) in the melanoma tumor microenvironment is driven by CD8(+) T cells. *Sci Transl Med.* 2013; 5(200):200ra116.
16. Li J, Byrne K T, Yan F, Yamazoe T, Chen Z, Baslan T, et al. Tumor Cell-Intrinsic Factors Underlie Heterogeneity of Immune Cell Infiltration and Response to Immunotherapy. *Immunity.* 2018; 49(1):178-93 e7.
17. Anastas I N, Kulikauskas R M, Tamir T, Rizos H, Long G V, von Euw E M, et al. WNT5A enhances resistance of melanoma cells to targeted BRAF inhibitors. *J Clin Invest.* 2014; 124(7):2877-90.
18. Hugo W, Zaretsky J M, Sun L, Song C, Moreno B H, Hu-Lieskovan S, et al. Genomic and Transcriptomic Features of Response to Anti-PD-1 Therapy in Metastatic Melanoma. *Cell.* 2016; 165(1):35-44.
19. Zhao F, Xiao C, Evans K S, Theivanthiran T, DeVito N, Holtzhausen A, et al. Paracrine Wnt5a-beta-Catenin Signaling Triggers a Metabolic Program that Drives Dendritic Cell Tolerization. *Immunity.* 2018; 48(1):147-60 e7.
20. Blumenthal A, Ehlers S, Lauber J, Buer J, Lange C, Goldmann T, et al. The Wingless homolog WNT5A and its receptor Frizzled-5 regulate inflammatory responses of human mononuclear cells induced by microbial stimulation. *Blood.* 2006; 108(3):965-73.
21. Oblak A, and Jerala R. Toll-like receptor 4 activation in cancer progression and therapy. *Clin Dev Immunol.* 2011; 2011:609579.
22. Dong P, Xiong Y, Yue J, Hanley S I B, and Watari H. Tumor-Intrinsic PD-L1 Signaling in Cancer Initiation, Development and Treatment: Beyond Immune Evasion. *Front Oncol.* 2018; 8:386.
23. Gato-Canas M, Zuazo M, Arasanz H, Ibanez-Vea M, Lorenzo L, Fernandez-Hinojal G, et al. PDL1 Signals through Conserved Sequence Motifs to Overcome Interferon-Mediated Cytotoxicity. *Cell Rep.* 2017; 20(8):1818-29.
24. Escors D, Gato-Canas M, Zuazo M, Arasanz H, Garcia-Granda M J, Vera R, et al. The intracellular signalosome of PD-L1 in cancer cells. *Signal Transduct Target Ther.* 2018; 3:26.
25. Moossavi M, Parsamanesh N, Bahrami A, Atkin S L, and Sahebkar A. Role of the NLRP3 inflammasome in cancer. *Mol Cancer.* 2018; 17(1):158.
26. Soler-Cardona A, et al. CXCL5 facilitates melanoma cell-neutrophil interaction and lymph node metastasis. *J Invest ermatol.* 2018; 138(7):1627-1635.
27. Park H W, Kim Y C, Yu B, Moroishi T, Mo J S, Plouffe S W, et al. Alternative Wnt Signaling Activates YAP/TAZ. *Cell.* 2015; 162(4):780-94.
28. Wang G, Lu X, Dey P, Deng P, Wu C C, Jiang S, et al. Targeting YAP-Dependent MDSC Infiltration Impairs Tumor Progression. *Cancer Discov.* 2016; 6(1):80-95.
29. Asea A, Rehli M, Kabingu E, Boch J A, Bare O, Auron P E, et al. Novel signal transduction pathway utilized by extracellular HSP70: role of toll-like receptor (TLR) 2 and TLR4. *J Biol Chem.* 2002; 277(17):15028-34.
30. Zhao F, Evans K, Xiao C, DeVito N, Theivanthiran B, Holtzhausen A, et al. Stromal Fibroblasts Mediate Anti-PD-1 Antibody Resistance via MMP-9 and Dictate TGF-β Inhibitor Therapy Sequencing in Melanoma. *Cancer Immunology Research.* 2018; 6(12).

31. Eichelbaum K, Winter M, Berriel Diaz M, Herzig S, and Krijgsveld J. Selective enrichment of newly synthesized proteins for quantitative secretome analysis. *Nat Biotechnol.* 2012; 30(10):984-90.
32. Mambula S S, and Calderwood S K. Heat shock protein 70 is secreted from tumor cells by a nonclassical pathway involving lysosomal endosomes. *J Immunol.* 2006; 177 (11):7849-57.
33. Swanson K V, Deng M, and Ting J P. The NLRP3 inflammasome: molecular activation and regulation to therapeutics. *Nat Rev Immunol.* 2019.
34. Lu B, Nakamura T, Inouye K, Li J, Tang Y, Lundback P, et al. Novel role of PKR in inflammasome activation and HMGB1 release. *Nature.* 2012; 488(7413):670-4.
35. Shen S, Niso-Santano M, Adjemian S, Takehara T, Malik S A, Minoux H, et al. Cytoplasmic STAT3 represses autophagy by inhibiting PKR activity. *Mol Cell.* 2012; 48(5):667-80.
36. Bai H, Zhang Q F, Duan J J, Yu D J, and Liu U. Downregulation of signal transduction and STAT3 expression exacerbates oxidative stress mediated by NLRP3 inflammasome. *Neural Regen Res.* 2018; 13(12): 2147-55.
37. Coll R C, Robertson A A, Chae J J, Higgins S C, Munoz-Planillo R, Inserra M C, et al. A small-molecule inhibitor of the NLRP3 inflammasome for the treatment of inflammatory diseases. *Nat Med.* 2015; 21(3):248-55.
38. Ndoye A, Budina-Kolomets A, Kugel C H, 3rd, Webster M R, Kaur A, Behera R, et al. ATG5 Mediates a Positive Feedback Loop between Wnt Signaling and Autophagy in Melanoma. *Cancer Res.* 2017; 77(21):5873-85.
39. Da Forno P D, Pringle J H, Hutchinson P, Osborn J, Huang Q, Potter L, et al. WNT5A expression increases during melanoma progression and correlates with outcome. *Clin Cancer Res.* 2008; 14(18):5825-32.
40. Holtzhausen A, Zhao F, Evans K S, Tsutsui M, Orabona C, Tyler D S, et al. Melanoma-Derived Wnt5a Promotes Local Dendritic-Cell Expression of IDO and Immunotolerance: Opportunities for Pharmacologic Enhancement of Immunotherapy. *Cancer immunology research.* 2015; 3(9):1082-95.
41. Fang H, Wu Y, Huang X, Wang W, Ang B, Cao X, et al. Toll-like receptor 4 (TLR4) is essential for Hsp70-like protein 1 (HSP70L1) to activate dendritic cells and induce Th1 response. *J Biol Chem.* 2011; 286(35):30393-400.
42. Murphy M E. The HSP70 family and cancer. *Carcinogenesis.* 2013; 34(6):1181-8.
43. Radons J. The human HSP70 family of chaperones: where do we stand? *Cell Stress Chaperones.* 2016; 21(3): 379-404.
44. He Y, Hara H, and Nunez G. Mechanism and Regulation of NLRP3 Inflammasome Activation. *Trends Biochem Sci.* 2016; 41(12):1012-21.
45. Tu S, Bhagat G, Cui G, Takaishi S, Kurt-Jones E A, Rickman B, et al. Overexpression of interleukin-1beta induces gastric inflammation and cancer and mobilizes myeloid-derived suppressor cells in mice. *Cancer Cell.* 2008; 14(5):408-19.
46. Qu J, Tao X Y, Teng P, Zhang Y, Guo C L, Hu L, et al. Blocking ATP-sensitive potassium channel alleviates morphine tolerance by inhibiting HSP70-TLR4-NLRP3-mediated neuroinflammation. *J Neuroinflammation.* 2017; 14(1):228.
47. van Deventer H W, Burgents J E, Wu Q P, Woodford R M, Brickey W J, Allen I C, et al. The inflammasome component NLRP3 impairs antitumor vaccine by enhancing the accumulation of tumor-associated myeloid-derived suppressor cells. *Cancer Res.* 2010; 70(24):10161-9.
48. Lecis D, Sangaletti S, Colombo M P, Chiodoni C. Immune checkpoint ligand reverse signaling: looking back to go forward in cancer therapy. *Cancers (Basel).* 2019; 11(5):E624.
49. Cordero M D, Alcocer-Gomez E, Ryffel B. Gain of function mutation and inflammasome driven diseases in human and mouse models. *J Autoimmun.* 2018; 91:13-22.
50. Booshehri L M, Hoffman H M. CAPS and NLRP3. *J Clin Immunol.* 2019; 39(3):277-286.
51. Benci J L, et al. Tumor interferon signaling regulates a multigenic resistance program to immune checkpoint blockade. *Cell.* 2016; 167(6):1540-1554.e12.
52. Holtzhausen A, et al. Melanoma-derived Wnt5a promotes local dendritic-cell expression of IDO and immunotolerance: pportunities for pharmacologic enhancement of immunotherapy. *Cancer Immunol Res.* 2015; 3(9): 1082-1095.
53. Johnson D B, et al. Tumor-specific MHC-II expression drives a unique pattern of resistance to immunotherapy via LAG-3/FCRL6 engagement. *JCI Insight.* 2018; 3(24): e120360.

Example 2

As shown in FIGS. 15A and B, IFN-β/anti-PD-L1 Antibody Treatment of the AKP Organoid colorectal cancer (CRC) Model Induces NLRP3 Inflammasome Activation, HSP70 Release, and Wnt5a Upregulation in a TLR4-dependent Manner. As shown in FIG. 15B, KRas mutant CRC Exhibits Elevated Levels of NLRP3 Inflammasome Activation based on HSP70 Release.

The invention claimed is:

1. A method of treating a cancer in a subject in need thereof the method comprising administering to the subject a therapeutically effective amount of an NLRP3 inhibitor and at least one of an anti-PD-1 antibody and an anti-PD-L1 antibody such that the cancer is treated in the subject, wherein the NLRP3 inhibitor is at least one of MCC950, a miRNA, a siRNA, and an oligonucleotide, and wherein the cancer comprises lung cancer, breast cancer, pancreatic cancer, colorectal cancer or renal cancer.

2. The method according to claim 1 in which the NLRP3 inhibitor is MCC950.

3. The method according to claim 1 in which the anti-PD-1 or anti-PD-L1 antibody is selected from the group consisting of Nivolumab (anti-PD-1), Pembrolizumab (anti-PD-1), atezolizumab (anti-PD-L1), avelumab (anti-PD-L1), and durvalumab (anti-PD-L1), and combinations thereof.

4. The method of claim 1, wherein the at least one of the anti-PD-1 antibody and anti-PD-L1 antibody is administered prior to the NLRP3 inhibitor.

5. The method of claim 1, wherein the at least one of the anti-PD-1 antibody and anti-PD-L1 antibody is administered after the NLRP3 inhibitor is administered.

6. The method of claim 1, wherein the method further comprises administering another anti-cancer therapy.

7. The method of claim 1, wherein the cancer comprises a cancer resistant to immune checkpoint inhibitors.

8. A method of increasing the efficacy of anti-PD-1 antibody immunotherapy in a subject having cancer, the method comprising administering to the subject a therapeutically effective amount of an NLRP3 inhibitor and an anti-PD-1 or anti-PD-L1 antibody such that the cancer is treated in the subject, wherein the NLRP3 inhibitor is at least one of MCC950, a miRNA, a siRNA, and an oligonucleotide, and wherein the cancer comprises lung cancer, breast cancer, pancreatic cancer, colorectal cancer or renal cancer.

9. The method according to claim 8 in which the anti-PD-1 or anti-PD-L1 antibody is administered prior to the NLRP3 inhibitor.

10. The method according to claim 8 in which the anti-PD-1 or anti-PD-L1 antibody is administered after the NLRP3 inhibitor.

11. The method according to claim 8, wherein the NLRP3 inhibitor is MCC950.

12. The method of claim 8, wherein the PD-1 antibody is selected from the group consisting of Nivolumab (anti-PD-1), Pembrolizumab (anti-PD-1), and combinations thereof; or the anti-PD-L1 antibody is selected from the group consisting of atezolizumab (anti-PD-L1), avelumab (anti-PD-L1), and durvalumab (anti-PD-L1), and combinations thereof.

13. The method of claim 1, wherein the subject is refractory or not responding to an anti-PD-1 cancer treatment.

14. The method of claim 13, wherein the method comprises:
    selecting a subject that was previously treated with anti-PD-1 inhibitor and was resistant to treatment.

15. The method of claim 13, wherein the NLRP3 inhibitor is MCC950.

16. The method of claim 13, wherein the anti-PD-1 treatment is an anti-PD-1 antibody or anti-PD-L1 antibody selected from the group consisting of Nivolumab (anti-PD-1), Pembrolizumab (anti-PD-1), atezolizumab (anti-PD-L1), avelumab (anti-PD-L1), and durvalumab (anti-PD-L1), and combinations thereof.

17. The method of claim 13, wherein the method comprises administering the NLRP3 inhibitor prior to administering the anti-PD-1 antibody or anti-PD-L1 antibody.

* * * * *